US007056947B2

(12) United States Patent
Powers et al.

(10) Patent No.: US 7,056,947 B2
(45) Date of Patent: Jun. 6, 2006

(54) AZA-PEPTIDE EPOXIDES

(75) Inventors: James C. Powers, Atlanta, GA (US);
Juliana L. Asgian, Fullerton, CA (US);
Karen E. James, Cumming, GA (US);
Zhao-Zhao Li, Norcross, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 309 days.

(21) Appl. No.: 10/603,054

(22) Filed: Jun. 24, 2003

(65) Prior Publication Data

US 2004/0048327 A1    Mar. 11, 2004

Related U.S. Application Data

(60) Provisional application No. 60/394,221, filed on Jul. 5, 2002, provisional application No. 60/394,023, filed on Jul. 5, 2002, provisional application No. 60/394,024, filed on Jul. 5, 2002.

(51) Int. Cl.
*A61K 31/335* (2006.01)
*C07D 303/38* (2006.01)

(52) U.S. Cl. ...................... 514/475; 549/548

(58) Field of Classification Search ............... 549/548; 514/475
See application file for complete search history.

(56) References Cited

U.S. PATENT DOCUMENTS 5,770,732 A  *  6/1998  Hirschmann et al. ....... 544/141
5,998,470 A  * 12/1999  Halbert et al. ............ 514/482
6,331,542 B1 * 12/2001  Carr et al. .............. 514/237.8
6,376,468 B1    4/2002  Overkleeft et al.
6,387,908 B1    5/2002  Nomura et al.
6,462,078 B1 * 10/2002  Ono et al. ................ 514/475
6,479,676 B1   11/2002  Wolf
6,586,466 B1 *  7/2003  Yamashita ............... 514/483
6,689,765 B1 *  2/2004  Baroudy et al. ........... 514/63
6,831,099 B1 * 12/2004  Crews et al. ............. 514/475

OTHER PUBLICATIONS

Kidwai et al, CA 125: 33462, 1996.*

* cited by examiner

*Primary Examiner*—Deborah C. Lambkin
(74) *Attorney, Agent, or Firm*—Thomas, Kayden, Horstemeyer & Risley LLP; Todd Deveau

(57) ABSTRACT

The present invention provides compositions for inhibiting proteases, methods for synthesizing the compositions, and methods of using the disclosed protease inhibitors. Aspects of the invention include aza-peptide epoxide compositions that inhibit proteases, for example cysteine proteases, either in vivo or in vitro. The disclosed compounds, pharmaceutically acceptable salts, pharmaceutically acceptable derivatives, prodrugs, or combinations thereof can be used to treat disease or pathological conditions related to the activity of proteases associated with a specific disease or condition. Such treatable conditions include viral infections, stroke, neurodegenerative disease, and inflammatory disease, among others.

50 Claims, No Drawings

SEQUENCE LISTING

<160> NUMBER OF SEQ ID NOS: 4

<210> SEQ ID NO 1
<211> LENGTH: 5
<212> TYPE: PRT
<213> ORGANISM: Artificial
<220> FEATURE:
<223> OTHER INFORMATION: consenus active site motif for caspases
<220> FEATURE:
<221> NAME/KEY: MISC_FEATURE
<222> LOCATION: (4)..(4)
<223> OTHER INFORMATION: X = R, Q, OR G

<400> SEQUENCE: 1

Gln Ala Cys Xaa Gly
1               5

<210> SEQ ID NO 2
<211> LENGTH: 4
<212> TYPE: PRT
<213> ORGANISM: artificial
<220> FEATURE:
<223> OTHER INFORMATION: caspase recognition sequence

<400> SEQUENCE: 2

Trp Glu His Asp
1

<210> SEQ ID NO 3
<211> LENGTH: 4
<212> TYPE: PRT
<213> ORGANISM: artificial
<220> FEATURE:
<223> OTHER INFORMATION: caspase group II recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 3

Asp Glu Xaa Asp
1

<210> SEQ ID NO 4
<211> LENGTH: 4
<212> TYPE: PRT
<213> ORGANISM: artificial
<220> FEATURE:
<223> OTHER INFORMATION: caspase group III recognition sequence
<220> FEATURE:
<221> NAME/KEY: MISC_FEATURE
<222> LOCATION: (1)..(1)
<223> OTHER INFORMATION: X = V OR L
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Xaa Glu Xaa Asp
1

AZA-PEPTIDE EPOXIDES

CROSS-REFERENCED TO RELATED APPLICATIONS

This application claims benefit of U.S. Provisional Patent Application No. 60/394,221 filed on Jul. 5, 2002, U.S. Provisional Patent Application No. 60/394,023, filed on Jul. 5, 2002, and U.S. Provisional Patent Application No. 60/394,024 filed on Jul. 5, 2002, all of which are incorporated by reference in their entirety.

BACKGROUND OF THE INVENTION

1. Field of the Invention

This invention relates generally to protease inhibitors and applications thereof, more specifically to peptide inhibitors of cysteine proteases, even more specifically to aza-peptide epoxides, methods of their use, and methods of their production.

2. Related Art

Protease inhibitors are important therapeutics in the treatment of a variety of disease conditions including viral infections such as HIV infection. Proteases are enzymes that cleave proteins or peptides and are classified into several groups. For example, cysteine proteases form a group of enzymes involved in numerous disease states, and inhibitors of these enzymes can be used therapeutically for the treatment of diseases involving cysteine proteases.

To date, a structurally diverse variety of cysteine protease inhibitors have been identified. Palmer, (1995) J. Med. Chem., 38, 3193, discloses certain vinyl sulfones which act as cysteine protease inhibitors for cathepsins B, L, S, O2 and cruzain. Other classes of compounds, such as aldehydes, nitriles, α-ketocarbonyl compounds, halomethyl ketones, diazomethyl ketones, (acyloxy)methyl ketones, ketomethylsulfonium salts and epoxy succinyl compounds have also been reported to inhibit cysteine proteases. See Palmer, id, and references cited therein. Many irreversible cysteine protease inhibitors have been described in the review by Powers, Asgian, Ekici, and James (2002) Chemical Reviews, 102, 4639. See Powers, id, and references cited therein. However, most of these known inhibitors are not considered suitable for use as therapeutic agents in animals, especially humans, because they suffer from various shortcomings. These shortcomings include lack of selectivity, cytotoxicity, poor solubility, and overly rapid plasma clearance.

In addition, epoxides also have been shown to inhibit cysteine proteases. The first epoxysuccinyl peptide discovered was E-64, a natural inhibitor, which was initially isolated from *Aspergillus japonicus* by Hanada et al. in 1978. The chemical structure was determined by optical rotation, NMR, IR, MS, elemental analysis, and amino acid analysis to be N-(N-(L-3-trans-carboxyoxiran-2-carbonyl)-L-leucyl)agmatine. Hanada and his coworkers showed that E-64 would inactivate the plant cysteine proteases papain, ficin, and bromelain.

E-64

Once the E-64 structure was elucidated, the research groups of Katunuma, Barrett, and others discovered E-64's inhibitory potency toward a large number of other cysteine proteases. E-64 inhibits papain, ficin, bromelain, cathepsin B, H, F, K, L, O, S, V, X, calpain, calpain II, cruzain, and other cysteine proteases. Cathepsin J and streptococcal cysteine protease are slowly inhibited by E-64.

Unlike many other microbial inhibitors, E-64 is a potent and specific irreversible inhibitor of cysteine proteases, and is used as a diagnostic reagent for identification of cysteine proteases. The compound E-64 does not inhibit serine proteases, aspartic proteases, or metalloproteases. However, not all cysteine proteases are inhibited by E-64. Examples of non-inhibited cysteine proteases are legumain and caspases. Caspases and legumain are members of the CD clan of cysteine proteases, while papain, cathepsins, and calpains are members of clan CA. The following table lists those enzymes which are inactivated by E-64 and those which are not inactivated.

Enzymes Inactivated or Not Inactivated by E-64

| enzymes inactivated | rate ($M^{-1} s^{-1}$) | enzymes not inactivated |
|---|---|---|
| ficin | 0.084 ($ID_{50}$) | trypsin |
| fruit bromelain | 0.110 ($ID_{50}$) | α-chymotrypsin |
| stem bromelain | 0.025 ($ID_{50}$) | kallikrein |
| papain | 0.104 ($ID_{50}$) | pepsin |
| cathepsin B | 89,400 | plasmin |
| cathepsin H | 4,000 | elastase |
| cathepsin L | 96,250 | mold acid protease |
| cathepsin K | 1.8 nM ($K_i$) | LDH |
| cathepsin S | 99,000 | thermolysin |
| cathepsin X | 775 | collagenase |
| cathepsin O | >100 μM ($IC_{50}$) | clostripain |
| cathepsin F |  | caspase 1 (ICE) |
| cathepsin V | >0.1 μM ($IC_{50}$) | legumain |
| cathepsin J |  |  |
| DPPI | 100 |  |
| streptococcal proteinase | 624 |  |
| papaya proteinase IV | 58,000 |  |
| calpain II | 7,500 |  |
| bleomycin hydrolase | >160 μM ($IC_{50}$) |  |
| cruzain | 70,600 |  |
| vignain | 32,500 |  |

Therefore, because of the aforementioned deficiencies in the art, there is a need for new compounds and methods for inhibiting proteases, in particular cysteine proteases.

SUMMARY OF THE INVENTION

Aspects of the present invention provide compositions for inhibiting proteases, methods for synthesizing the compositions, and methods of using the disclosed protease inhibitors. The compositions described herein can inhibit proteases, for example cysteine proteases, either in vivo or in vitro, by contacting a cysteine protease with an aza-peptide epoxide. The disclosed compounds, pharmaceutically acceptable salts, pharmaceutically acceptable derivatives, prodrugs, or combinations thereof can be used to treat disease or pathological conditions related to the activity of proteases associated with a specific disease or condition. Such treatable conditions include viral infections, stroke, neurodegenerative disease, and inflammatory disease, among others. Methods disclosed herein for treating diseases include administering an effective amount of an aza-peptide epoxide to a host in need thereof to inhibit or reduce protease activity in the host, particularly cysteine protease activity, more particularly activity of caspases, calpains, cathepins, papain, gingipain, clostripain, separin, or legumain. One or more aza-peptide epoxides of the present invention can also be used alone or in combination with each other, other protease inhibitors, or another therapeutic agent including anti-viral compounds such as anti-viral nucleosides including nucleoside analogs.

One aspect of the invention provides aza-peptide epoxide compositions, for example a compound or pharmaceutically acceptable salt or pharmaceutically acceptable derivative thereof according to Formula I below. In some aspects of the present invention, aza-peptide epoxide inhibitors are specific for cysteine proteases and do not inhibit serine proteases or aspartyl proteases. In another aspect of the present invention, these aza-peptide epoxide compounds potently and specifically inhibit clan CD of cysteine proteases and are also inhibitors of clan CA. Exemplary differences between aza-peptide epoxides disclosed herein and other cysteine proteases inhibitors include different mechanisms of inhibition of the cysteine residue and the binding modes.

Some aza-peptide epoxides of the present invention can be constructed to selectively inhibit individual cysteine proteases or groups of cysteine proteases. These aza-peptide epoxides can, for example, contain acidic aza-amino acid residues in the P1 site. Such aza-peptide epoxides are potent inhibitors of caspases. Aza-peptide epoxide caspase inhibitors are useful for the treatment of stroke and inflammatory diseases, and as inhibitors of apoptosis. Thus, another aspect provides a method of treating stroke, inflammatory disease, or inhibiting apoptosis including administering an effective amount of a aza-peptide epoxide to a patient in need thereof. Such patients can include any mammal, for example a mammal exhibiting symptoms characteristic protease related pathology or disease condition such as stroke, inflammatory disease, or pathology related to apoptosis.

Another aspect of the present invention provides an aza-peptide epoxide composition containing an aza-asparagine residue at the P1 position. Aza-peptide epoxides having an aza-asparagine residue at the P1 position inhibit legumain and can, therefore, modulate the immune system through such inhibition. Cleavage of antigens by proteases such as legumain and related proteases is a step in antigen presentation including the display of MHC class II peptides. Thus, another aspect of the invention provides a method of modulating the immune system of a patient by administering to a host an effective amount of an aza-peptide epoxide composition. The aza-peptide epoxide can modulate the immune system by inhibiting the cleavage of antigens in the patient and thereby reducing the display of antigen peptides on cell surfaces.

Yet another aspect of the invention provides a method of treating autoimmune disease by administering an effective amount of an aza-peptide epoxide to a host in need thereof. The host can be any mammal, including primates, which demonstrate symptoms associated with any number of autoimmune diseases including but not limited to lupus, for example lupus erythematosus, and cancers.

Another aspect of the invention provides aza-peptide epoxides containing basic residues at the P1 position. Such aza-peptide epoxides inhibit proteases such as gingipain, separin, and clostripain. Aza-peptide epoxide inhibitors of gingipain can be used for treatment of periodontal diseases. Aza-peptide epoxide inhibitors of separin are useful for stopping, modulating, or interfering with cell division.

Yet another aspect of the invention provides aza-peptide epoxide protease inhibitors with hydrophobic amino acid residues in the P2 site. These aza-peptide epoxide protease inhibitors inhibit proteases such as cathepsins, including cathepsin B, and papain. Aza-peptide epoxide inhibitors of cathepsin B are useful for treating hyperproliferative conditions including cancer.

Another aspect provides aza-peptide epoxides having small hydrophobic alkyl amino acid residues at P2 are good inhibitors of calpain I and II. These inhibitors are useful as neuroprotectants and can be used as therapeutics for the treatment or prevention of neurodegeneration and stroke. Exemplary neuodegenerative disorders that can be treated with the disclosed aza-peptide epoxides include but are not limited to stroke, Alzheimer's disease, Parkinson's disease, multiple sclerosis, neuropathies, Huntington's disease, and myotrophic lateral sclerosis (ALS).

In another aspect, this invention provides a method to identify proteolytic enzymes and a method to prevent proteolysis.

DETAILED DESCRIPTION OF THE INVENTION

The present invention may be understood more readily by reference to the following detailed description of the invention and the Examples included therein.

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

Cysteine Proteases. The aza-peptide epoxide compositions provided herein inhibit enzymatic cleavage of proteins or peptides, or a combination thereof. Exemplary enzymes inhibited by aza-peptide epoxides include cysteine proteases, for example, calpain. Calpain uses a cysteine residue in the catalytic mechanism in contrast to serine proteases which utilize a serine residue. Exemplary cysteine proteases include papain, cathepsin B, calpains, caspases, gingipain, clostripain, legumain, and several viral enzymes.

Caspases are a recently discovered family of cysteine endoproteases, which are highly selective for Asp at the P1 residue. As a result, this newly emerging family of proteases has been called caspases (cysteinyl aspartate-specific protease). All caspases contain the conserved pentapeptide active site motif Gln-Ala-Cys-X-Gly (QACXG)(SEQ.ID NO.1), where X=Arg, Gln, Gly (R, Q, G), and are synthesized as inactive proenzymes. The only other mammalian protease with specificity for Asp is the lymphocyte serine protease, granzyme B. Many of the proteolytic cleavages that are observed during apoptosis and cytokine maturation are due to the action of various caspases. Indeed, many of the procaspases are activated by other caspases, which selectively cleave at P1 Asp residues in their recognition sites.

At present, there are 14 homologous members of the caspase family in humans. Some caspases are important mediators of inflammation, where they are involved in the production of inflammatory cytokines, and others are involved in apoptosis, where they participate in signaling and effector pathways. Group I (1, 4, 5, 11, 12, 13, and 14) caspases are primarily mediators of inflammation and are involved in proteolytic activation of proinflammatory cytokines. Caspase-1 is also involved in the Fas and TNFR apoptotic pathway. Group II (2, 3, and 7) caspases are late phase effectors of apoptosis and are involved in the cleavage of key structural and homeostatic proteins. Caspase-3, also known as CPP32 (cysteine protease protein 32-kDa), Yama or apopain, is believed to be one of the major effectors in apoptosis. This enzyme is a key executioner because it is responsible either partially or totally for proteolytic cleavage of key apoptotic proteins. It functions to decrease or destroy essential homeostatic pathways during the effector phase of apoptosis. Caspase-3 cleaves or activates nuclear enzymes, such as poly(ADP-ribose) polymerase (PARP), the 70 kDa subunit of the U1 small ribonucleoprotein, the catalytic subunit of DNA-dependent protein kinase, and protein kinase Cδ. Group III (6, 8, 9, 10) caspases are involved in the upstream early activation of effector caspases. Studies have shown that caspase-8 and 10 can cleave radiolabeled precursors for caspase-3. Caspase-6 is the only known caspase that cleaves the lamins, the major structural proteins in the nuclear envelope. Proteolysis of lamins is observed in cells undergoing apoptosis. Caspase-8 (MACH/FLICE), which can cleave all other known caspases, is suggested to lie in the pinnacle of the apoptotic cascade, at least when apoptosis is initiated by some stimuli such as Fas-L and TNF. Accordingly, the present invention encompasses compositions and methods of altering, inhibiting, or reducing the formation of enzymatic reaction products involving cysteine proteases. Inhibiting the formation of cysteine protease reaction products in vivo can provide therapeutic effects to patients suffering from unregulated or Caspases have a specificity for at least the four amino acids to the left of the cleavage site (P side). The S4 subsite is the single most important determinant of specificity among caspases after the P1 Asp. The optimal sequences of the caspases were obtained using a positional-scanning combinatorial substrate library (PS-CSL). The optimal recognition sequences for these enzymes are closely related to the sequences found in known macromolecular substrates. Group I caspases' optimal sequence is Trp-Glu-His-Asp (WEHD) (SEQ.ID NO.2) with S4 favoring hydrophobic amino acids. Group II caspases' optimal sequence is Asp-Glu-X-Asp (DEXD) (SEQ. ID NO.3) with a requirement for Asp in S4. Group III caspases' optimal sequence is N-Glu-X-Asp where N=Val or Leu and X can be any amino acid ((V,L)EXD) (SEQ. ID NO.4) with a preference for branched, aliphatic side chains in S4. The S3 subsite prefers glutamic acid (E) in most of the caspases which could be explained by the salt link between Arg-341 (involved in stabilization of the P1 aspartic acid) and the glutamic acid in P3.

Neural tissues, including brain, are known to possess a large variety of proteases, including at least two calcium stimulated proteases termed calpains. Calpains are present in many tissues in addition to the brain. Calpain I is activated by micromolar concentrations of calcium while calpain II is activated by millimolar concentrations. In the brain, calpain II is the predominant form, but calpain I is found at synaptic endings and is thought to be the form involved in long term potentiation, synaptic plasticity, and cell death. Other $Ca^{2+}$ activated cysteine proteases may exist, and the term "calpain" is used to refer to all $Ca^{2+}$ activated cysteine proteases, including calpain I and calpain II. The terms "calpain I" and "calpain II" are used herein to refer to the micromolar and millimolar activated calpains, respectively, as described above. While calpains degrade a wide variety of protein substrates, cytoskeletal proteins seem to be particularly susceptible to attack. In some cases, the products of the proteolytic digestion of these proteins by calpain are distinctive and persistent over time. Since cytoskeletal proteins are major components of certain types of cells, this provides a simple method of detecting calpain activity in cells and tissues. Activation of calpains and/or accumulation of breakdown products of cytoskeletal elements have been observed in neural tissues of mammals exposed to a wide variety of neurodegenerative diseases and conditions. For example, these phenomena have been observed following ischemia in gerbils and rats, following stroke in humans, following administration of the toxins kainate, trimethyltin, or colchicine in rats, and in human Alzheimer's disease.

Cathepsin B is involved in muscular dystrophy, myocardial tissue damage, tumor metastasis, and bone resorption. In addition, a number of viral processing enzymes, which are essential for viral infection, are cysteine proteases. Inhibitors of cysteine proteases would have multiple therapeutic uses.

Other important cysteine proteases are the bacterial enzymes clostripain and gingipain. Gingipain causes tissue destruction during periodontal diseases. Legumain is a related cysteine proteases which is involved in inflammatory diseases. Separin is involved in separation of sister chromatids during cell division.

The present invention includes all hydrates, solvates, complexes and prodrugs of the compounds of this invention. The term prodrug refers to a pharmacologically inactive compound that is converted to an active drug by a metabolic biotransformation. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula I. Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

The subject invention also includes isotopically-labelled compounds, and the pharmaceutically acceptable salts thereof, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine.

Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. An enantiomerically enriched mixture means a mixture having greater than about 50% of a single enantiomer. In cases in which compounds have unsaturated carbon-carbon double bonds, both the cis (Z) and trans (E) isomers are within the scope of this invention. The compositions of the present invention can be substantially optically pure. Substantially optically pure means a composition having greater than 90%, preferably greater than 95%, most preferably greater than 98% of a single optical isomer.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more stitch carriers, and the like.

In discussing the interactions of peptides with cysteine proteases, we have utilized the nomenclature of Schechter and Berger [*Biochem. Biophys. Res. Commun.* 27, 157–162 (1967); incorporated herein by reference]. The individual amino acid residues of a substrate or inhibitor are designated P1, P2, etc. and the corresponding subsites of the enzyme are designated S1, S2, etc. The scissile bond of the substrate is S1–1'. The most important recognition subsites of cysteine proteases are S1 and S2.

Amino acid residues and blocking groups are designated using standard abbreviations [see J. Biol. Chem. 260, 14–42 (1985) for nomenclature rules; incorporated herein by reference]. An amino acid residue (AA) in a peptide or inhibitor structure refers to the part structure —NH—CHR$_1$—CO—, where R$_1$ is the side chain of the amino acid residue AA. It will be appreciated that at least one of the amino acid residues of the aza-peptide epoxides of the invention may be substituted by one of the well known non-naturally occurring amino acid residues. Alterations such as these may serve to increase the stability, bioavailability and/or inhibitory action of the peptides of the invention. Moreover, any of the aza-peptide epoxides described herein may, additionally, have a non-peptide macromolecular carrier group covalently attached to their amino and/or carboxy termini. Such macromolecular carrier groups may include, for example, lipid-fatty acid conjugates, polyethylene glycol, or carbohydrates.

The following figure shows the structure of an aza-peptide epoxide. An aza-amino acid residue is an alpha-amino acid residue where the alpha-carbon has been replaced by a nitrogen atom. It will be abbreviated as the three letter code for the amino acid preceded by an "A". Therefore, aza-alanine will be abbreviated as AAla and aza-aspartic acid as AAsp. The epoxide will be abbreviated as EP for the $C_2H_2O$ residue.

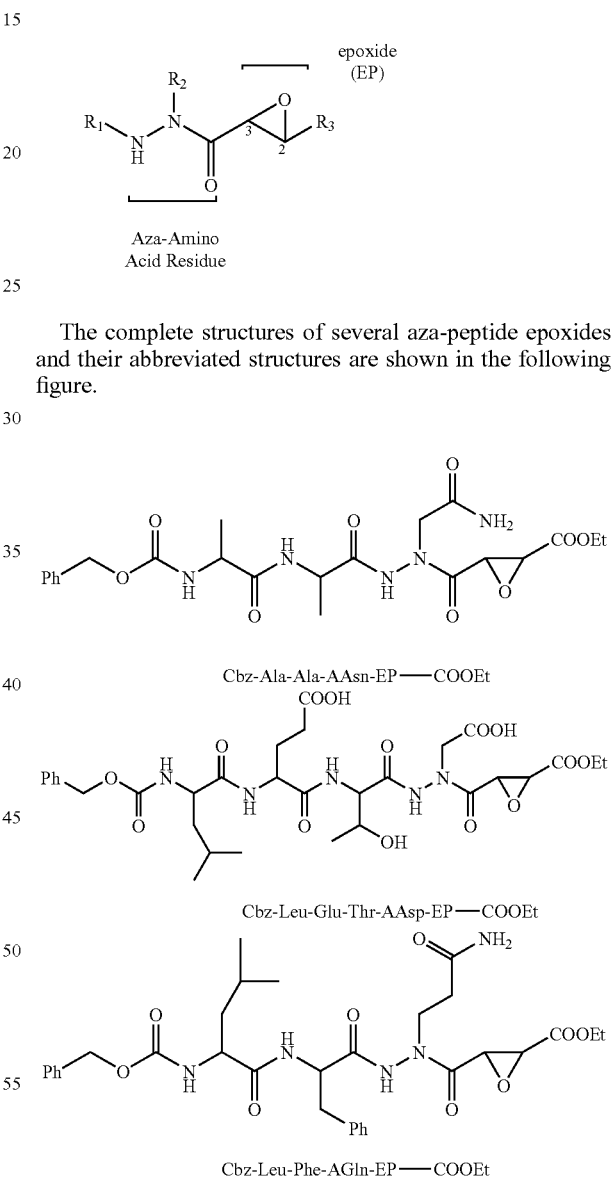

Aza-Amino Acid Residue

The complete structures of several aza-peptide epoxides and their abbreviated structures are shown in the following figure.

Cbz-Ala-Ala-AAsn-EP—COOEt

Cbz-Leu-Glu-Thr-AAsp-EP—COOEt

Cbz-Leu-Phe-AGln-EP—COOEt

The R$_3$ group would be abbreviated as CO$_2$H, CO$_2$Et, CO$_2$R, CONHR, CONRR', or CO-AA-T if the aza-peptide epoxide has an epoxysuccinate moiety in its structure. Otherwise, the structure of the R$_3$ group would be drawn or abbreviated.

There are four structural isomers at the epoxide moiety, two trans isomers (2S,3S and 2R,3R) and two cis isomers (2R,3S and 2S,3R). The numbering of the carbons of the epoxide is shown above. The epoxide ring is also known as an oxirane ring.

The term "amino," as used herein, refers to —$NH_2$ or derivatives thereof formed by independent replacement of one or both hydrogen atoms thereon with a substituent or substituents independently selected from alkyl, alkanoyl, aryl, arylalkyl, cycloalkyl, cycloalkylalkyl, heteroaryl, heteroarylalkyl, and an amino protecting group.

The term "$C_{1-10}$ acyl," as used herein, refers to a $C_{1-10}$ alkyl group, as defined herein, having an attached carbonyl group.

The term "$C_{1-10}$ alkoxy," as used herein, refers to a $C_{1-10}$ alkyl group, as defined herein, attached to the parent molecular group through an oxygen atom.

The term "$C_{1-10}$ alkyl" as used herein refers to a branched or unbranched hydrocarbon group of carbon atoms, such as methyl, ethyl, n-propyl, isopropyl, n-butyl, isobutyl, 1-butyl, and the like or branched or unbranched hydrocarbon groups of carbon atoms that either contain double or triple carbon bonds.

The term "$C_{1-10}$ alkylamino," as used herein, refers to a $C_{1-10}$ alkyl group, as defined herein, to which is attached at least one amino substituent.

The term "$C_{3-15}$ cycloalkyl" as applied herein is meant to include cyclic hydrocarbon chains. Examples of these cyclic hydrocarbon chains include cyclopropane, cyclobutane, cyclopentane, cyclohexane, cycloheptane, cyclooctane, cyclononane, cyclodecane, cycloundecane, etc.

The term "$C_{2-12}$ dialkylamino," as used herein, refers to two $C_{1-10}$ alkyl groups, as defined herein, that are attached to an amino substituent.

The term "$C_{1-10}$ fluoroalkyl," as used herein, refers to a $C_{1-10}$ alkyl group, as defined herein, to which is attached at least one fluorine substituent.

The term "$C_{1-10}$ perfluoroalkyl," as used herein, refers to a $C_{1-10}$ alkyl group in which all of the hydrogen atoms have been replaced with fluorine atoms.

The term biotinyl, as use herein, refers to biotin without the biotin carboxyl hydroxyl group.

By the term "effective amount" of a compound as provided herein is meant a nontoxic but sufficient amount of the compound to provide the desired utility. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

The term "pharmaceutically acceptable salt(s)", as used herein, unless otherwise indicated, includes salts of acidic or basic groups which may be present in the compounds of Formula I. The compounds of Formula I that are basic in nature are capable of forming a wide variety of salts with various inorganic and organic acids. The acids that may be used to prepare pharmaceutically acceptable acid addition salts of such basic compounds of Formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, TFA, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Those compounds of the Formula I that are acidic in nature, are capable of forming base salts with various pharmacologically acceptable cations. Examples of such salts include the alkali metal or alkaline earth metal salts and particularly, the sodium and potassium salts.

The term "pharmaceutically acceptable derivative" refers to any homolog, analog, or fragment corresponding to the aza-peptide epoxides of the present invention provided herein which inhibits protease activity and is relatively non-toxic to the subject or host.

The term "pharmaceutically acceptable" means a material that is not biologically or otherwise undesirable, i.e., the material may be administered to an individual along with the selected bicyclic compound without causing any undesirable biological effects or interacting in a deleterious manner with any of the other components of the pharmaceutical composition in which it is contained.

As used herein, and without limitation, the term "derivative" is used to refer to any compound which has a structure derived from the structure of the compounds of the present invention and whose structure is sufficiently similar to those disclosed herein and based upon that similarity, would be expected, by one skilled in the art, to exhibit the same or similar activities and utilities as the claimed compounds.

The following abbreviations have also been used: AFC, 7-amino-4-trifluoromethylcoumarin; AAsp, aza-aspartic acid residue; AAsn, aza-asparagine; ALeu, aza-leucine; ALys, aza-lysine residue; AHph, aza-homophenylalanine residue; AOrn, aza-ornithine; AMC, 7-amino-4-methylcoumarin; Cbz, Ph-$CH_2$OCO—; DCC, 1,3-dicyclohexylcarbodiimide; DMAP, 4-dimethylaminopyridine; DMF, N,N-dimethylformamide; EDC, 1-(3-dimethylaminopropyl)-3-ethylcarbodiimide hydrochloride; EtOAc, ethyl acetate; HOBt, 1-hydroxybenzotriazole; HRMS, high resolution mass spectrometry; IBCF, isobutyl chloroformate; NMM, 4-methylmorpholine; Np2,2-naphthyl-alanyl; PhPr, Phenylpropyl; TFA, trifluoroacetic acid; THF, tetrahydrofuran; TLC, thin layer chromatography.

One embodiment of the present invention provides aza-peptide epoxides having the following structural Formula I:

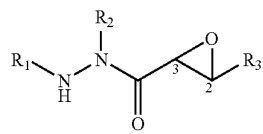

wherein, $R_1$ is selected from the group consisting of $M_1$, $M_2$-$AA_1$, $M_2$-$AA_2$-$AA_1$, and $M_2$-$AA_3$-$AA_2$-$AA_1$;

$M_1$ is selected from the group consisting of $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, X—CO—, X—CS—, Y—$SO_2$—, Y—O—CO—, Y—O—CS—, phenyl substituted with K, phenyl disubstituted with K, and morpholine-CO—;

$M_2$ is selected from the group consisting of H, $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, X—CO—, X—CS—, Y—$SO_2$—, Y—O—CO—, Y—O—CS—, phenyl, phenyl substituted with K, phenyl disubstituted with K, and morpholine-CO—;

X is selected from the group-consisting of H, $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, biotinyl, and $C_{1-10}$ alkyl with an attached phenoxy group substituted with K on the phenoxy group;

Y is selected from the group consisting of $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, biotinyl, and $C_{1-10}$ alkyl with an attached phenoxy group substituted with K on the phenoxy group;

J is selected from the group consisting of halogen, $CO_2H$, OH, CN, $NO_2$, $NH_2$, $C_{1-10}$ alkoxy, $C_{1-10}$ alkylamino, $C_{2-12}$ dialkylamino, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, phenoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—$CO_2H$, alpha-aminoheptanoic acid, $NH_2$—CH($CH_2$-1-naphthyl)-$CO_2H$, $NH_2$—CH($CH_2$-2-naphthyl)-$CO_2H$, $NH_2$—CH($CH_2$-cyclohexyl)-$CO_2H$, $NH_2$—CH($CH_2$-cyclopentyl)-$CO_2H$, $NH_2$—CH($CH_2$-cyclobutyl)-$CO_2H$, $NH_2$—CH($CH_2$-cyclopropyl)-$CO_2H$, trifluoroleucine, 4-fluorophenylalanine, lysine substituted on the epsilon nitrogen with a biotinyl group, and hexafluoroleucine;

$R_2$ is selected from the group consisting of $C_{1-10}$ alkyl, $C_{1-10}$ alkyl substituted with Q, $C_{1-10}$ alkyl substituted with phenyl, $C_{1-10}$ alkyl with an attached phenyl substituted with K, $C_{1-10}$ alkyl substituted with naphthyl, $C_{1-10}$ alkyl with an attached phenyl substituted with K, phenyl, phenyl substituted with K, naphthyl, naphthyl substituted with K, $C_{1-10}$ alkyl substituted with $CONH_2$, $C_{1-10}$ alkyl substituted with $CONHR_4$, $C_{1-10}$ alkyl substituted with $CO_2H$, $C_{1-10}$ alkyl substituted with $CO_2R_4$, $CH_2CH_2SCH_3$, $CH_2$-3-indolyl, $CH_2$-2-thienyl, $CH_2$-2-furyl, $CH_2$-3-furyl, $CH_2$-2-imidazyl, $C_{1-10}$ alkyl substituted with G, $C_{1-10}$ alkyl with an attached phenyl substituted with G, $C_{1-10}$ alkyl with an attached naphthyl substituted with G, phenyl substituted with G, and naphthyl substituted with G;

$R_4$ is selected from the group consisting of $C_{1-10}$ alkyl and $C_{1-10}$ alkyl substituted with phenyl;

Q is selected independently from the group consisting of $C_{1-10}$ alkoxy, $C_{1-10}$ alkyl-S—, $C_{1-10}$ alkoxy substituted with phenyl, and $C_{1-10}$ alkyl-S— substituted with phenyl;

G is selected independently from the group consisting of amidino (—C(=NH)$NH_2$), guanidino (—NHC(=NH)$NH_2$), isothiureido (—S—C(=NH)$NH_2$), amino, $C_{1-6}$ alkylamino, $C_{2-12}$ dialkylamino, and imidazyl;

$R_3$ is selected independently from the group consisting of $R_5$, $CO_2H$, $CO_2R_5$, $CONHR_6$, $CONR_6R_7$, CO-$AA_4$-T,

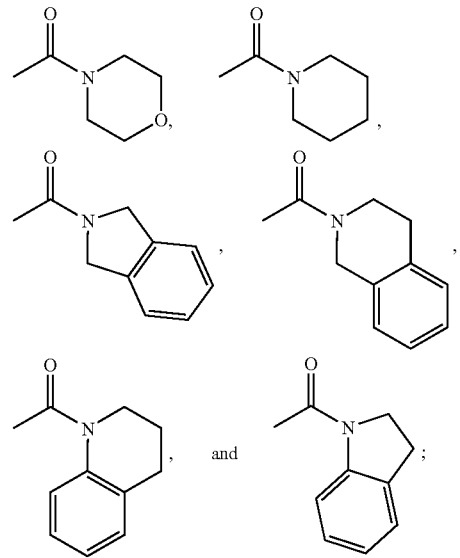

$R_5$ is selected independently from the group consisting of $C_{1-10}$ alkyl, $C_{3-15}$ cyclized alkyl, $C_{1-10}$ alkyl with a phenyl group attached to the $C_{1-10}$ alkyl, $C_{3-15}$ cyclized alkyl with an attached phenyl group, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{3-15}$ cyclized alkyl with an attached phenyl group substituted with K, $C_{1-10}$ alkyl with a naphthyl group attached to the $C_{1-10}$ alkyl, $C_{3-15}$ cyclized alkyl with an attached naphthyl group, $C_{1-10}$ alkyl with an attached naphthyl group substituted with K, $C_{1-10}$ alkyl with an attached naphthyl group disubstituted with K, $C_{1-10}$ alkyl with an attached naphthyl group trisubstituted with K, and $C_{3-15}$ cyclized alkyl with an attached naphthyl group substituted with K;

T is selected independently from the group consisting of OH, $OR_8$, $NHR_9$, and $NR_8R_9$;

$AA_4$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—$CO_2H$, alpha-aminoheptanoic acid, $NH_2$—CH($CH_2$-1-naphthyl)—$CO_2H$, $NH_2$—CH($CH_2$-2-naphthyl)-$CO_2H$, $NH_2$—CH($CH_2$-cyclohexyl)-$CO_2H$, $NH_2$—CH($CH_2$-cyclopentyl)-$CO_2H$, $NH_2$—CH($CH_2$-cyclobutyl)-$CO_2H$, $NH_2$—CH($CH_2$-cyclopropyl)-$CO_2H$, trifluoroleucine, 4-fluorophenylalanine, lysine substituted on the epsilon nitrogen with a biotinyl group, and hexafluoroleucine;

$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-10}$ alkyl with a morpholine [—$N(CH_2CH_2)O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2CH_2OCH_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, —NH—$CH_2CH_2$-(4-hydroxyphenyl), —NH—$CH_2CH_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl;

$R_8$ and $R_9$ are selected independently from the group consisting of H, $C_{1-10}$ alkyl, phenyl, nitrophenyl, and $C_{1-10}$ alkyl substituted with phenyl;

the stereochemistry at the epoxide carbons 2 and 3 is selected from the group consisting of cis, trans, R,R, S,S, R,S, and S,R.

The following compounds are representatives of the invention:

APhe-(trans)-EP-COOEt,
Cbz-APhe-(trans)-EP-COOEt,
Cbz-APhe-(trans)-EP-CH$_2$CH$_2$Ph,
Cbz-ALeu-(trans)-EP-COOEt,
Cbz-AHph-(trans)-EP-COOEt,
Ac-AHph-(trans)-EP-COOEt,
Boc-Nva-AHph-(trans)-EP-COOEt,
Boc-Nle-AHph-(trans)-EP-COOEt,
Boc-Nle-AHph-(trans)-EP-CH$_2$CH$_2$Ph,
Boc-Nva-AHph-(trans)-EP-CH$_2$CH$_2$Ph,
Boc-Abu-AHph-(trans)-EP-CH$_2$CH$_2$Ph,
Boc-Ala-AHph-(trans)-EP-CH$_2$CH$_2$Ph,
Boc-Np2-ALeu-(trans)-EP-COOEt,
Suc-Np2-ALeu-(trans)-EP-COOEt,
Ac-Leu-ALeu-(trans)-EP-COOEt,
Ac-Leu-AHph-(trans)-EP-COOEt,
Nva-AHph-(trans)-EP-CH$_2$CH$_2$Ph.TFA,
Nle-AHph-(trans)-EP-COOEt.TFA,
Ala-AHph-(trans)-EP-CH$_2$CH$_2$Ph.TFA,
Cbz-Leu-ALeu-(2S,3S)-EP-COOEt,
Cbz-Leu-ALeu-(2R,3R)-EP-COOEt,
Cbz-Leu-ALeu-(trans)-EP-COOEt,
Cbz-Leu-ALeu-(cis)-EP-COOEt,
Cbz-Phe-ALeu-(trans)-EP-COOEt,
Cbz-Phe-ALeu-(trans)-EP-CH$_2$CH$_2$Ph,
Cbz-Phe-APhe-(trans)-EP-CH$_2$CH$_2$Ph,
Cbz-Leu-AAbu-(trans)-EP-COOEt,
Cbz-Leu-AAbu-(trans)-EP-COOH,
Cbz-Leu-AHph-(cis)-EP-COOEt,
Cbz-Leu-AHph-(2S,3S)-EP-COOEt,
Cbz-Leu-AHph-(2R,3R)-EP-COOEt,
Cbz-Leu-AHph-(2S,3S)-EP-COOH,
Cbz-Leu-Leu-ALeu-(trans)-EP-COOEt,
Cbz-Leu-Leu-ALeu-(2S,3S)-EP-COOEt,
Cbz-Leu-Leu-ALeu-(2R,3R)-EP-COOEt,
Cbz-Leu-Leu-ALeu-(2S,3S)-EP-COOH,
Cbz-Leu-Phe-AGln-(2S,3S)-EP-COOEt,
Cbz-Leu-Phe-AGln-(2R,3R)-EP-COOEt,
Cbz-Leu-Phe-AGln-(trans)-EP-COOEt,
Cbz-Ala-Ala-AAsn-(trans)-EP-COOEt,
Cbz-Ala-Ala-AAsn-(2S,3S)-EP-COOEt,
Cbz-Ala-Ala-AAsn-(2R,3R)-EP-COOEt,
Cbz-Ala-Ala-AAsn-(cis)-EP-COOEt,
Cbz-Ala-Ala-AAsn-(trans)-EP-COOCH$_2$Ph,
Cbz-Ala-Ala-AAsn-(S,S)-EP-COOCH$_2$Ph,
Cbz-Ala-Ala-AAsn-(S,S)-EP-COOCH$_2$CH$_2$Ph,
Cbz-Ala-Ala-AAsn-(S,S)-EP-CONHCH$_2$Ph,
Cbz-Ala-Ala-AAsn-(S,S)-EP-CONHCH$_2$CH$_2$Ph,
Cbz-Ala-Ala-AAsn-(R,R)-EP-CO-Ala-NH-Bzl,
Cbz-Ala-Ala-AAsn-(S,S)-EP-CON(nBu)$_2$,
Cbz-Ala-Ala-AAsn-(S,S)-EP-CON(CH$_3$)CH$_2$Ph,
Cbz-Ala-Ala-AAsn-(trans)-EP-CH$_2$CH$_2$Ph,
Cbz-Ala-Ala-AAsn-(trans)-EP-Ph-4-Cl,
Cbz-Ala-Ala-NHN(CH$_2$COOEt)-(trans)-EP-COOEt,
PhPr-Val-Ala-AAsp-(2R,3R)-EP-COOCH$_2$Ph,
PhPr-Val-Ala-AAsp-(2S,3S)-EP-COOCH$_2$Ph,
PhPr-Val-Ala-AAsp-(trans)-EP-COOCH$_2$Ph,
PhPr Val-Ala-AAsp-(trans)-EP-CH$_2$CH$_2$Ph,
Cbz-Ile-Glu-Thr-AAsp-(2S,3S)-EP-COOEt,
Cbz-Ile-Glu-Thr-AAsp-(2R,3R)-EP-COOEt,
Cbz-Leu-Glu-Thr-AAsp-(2S,3S)-EP-COOEt,
Cbz-Leu-Glu-Thr-AAsp-(2R,3R)-EP-COOEt,
Cbz-Asp-Glu-Val-AAsp-(2S,3S)-EP-COOEt,
Cbz-Asp-Glu-Val-AAsp-(2R,3R)-EP-COOEt,
Cbz-Glu-Val-AAsp-(2S,3S)-EP-COOEt,
PhPr-Val-Ala-AAsp-(2S,3S)-EP-CON(CH$_2$CH$_2$CH$_2$CH$_3$)$_2$,
PhPr-Val-Ala-AAsp-(2S,3S)-EP-CON(CH$_2$Ph)$_2$,
Cbz-Leu-Glu-Thr-AAsp-(2S,3S)-EP-CON(CH$_2$Ph)$_2$,
Cbz-Ile-Glu-Thr-AAsp-(2S,3S)-EP-CON(CH$_2$Ph)$_2$,
Cbz-Leu-Glu-Thr-AAsp-(2S,3S)-EP-CON(CH$_3$)CH$_2$Ph,
PhPr-Val-Ala-AAsp-(2S,3S)-EP-CON(CH$_3$)CH$_2$Ph,
Cbz-Ile-Glu-Thr-AAsp-(2S,3S)-EP-CON(CH$_3$)CH$_2$Ph,
PhPr-Leu-ALys-(2S,3S)-EP-CO$_2$Et,
PhPr-Leu-AOrn-(2S,3S)-EP-CO$_2$Et,
Cbz-Val-AAsp-(S,S)-EP-COOEt,
Cbz-Val-AAsp-(S,S)-EP-COOH,
Cbz-Val-AAsp-(trans)-EP-CH$_2$CH$_2$Ph,
Cbz-Val-AAsp-(trans)-EP-Ph-4-Cl,
PhPr-Val-Ala-AAsp-(S,S)-EP-COOEt,
PhPr-Val-Ala-AAsp-(R,R)-EP-COOEt,
PhPr-Val-Ala-AAsp-(S,S)-EP-COOCH$_2$CH$_2$Ph,
PhPr-Val-Ala-AAsp-(S,S)-EP-CONHCH$_2$CH$_3$,
PhPr-Val-Ala-AAsp-(S,S)-EP-CONHCH$_2$Ph,
PhPr-Val-Ala-AAsp-(R,R)-EP-CONHCH$_2$Ph,
PhPr-Val-Ala-AAsp-(S,S)-EP-CONHCH$_2$CH$_2$Ph, PhPr-Val-Ala-AAsp-(R,R)-EP-CONHCH$_2$CH$_2$Ph,
PhPr-Val-Ala-AAsp-(S,S)-EP-CONHCH$_2$CH(OH)Ph,
PhPr-Val-Ala-AAsp-(R,R)-EP-CONHCH$_2$CH(OH)Ph,
PhPr-Val-Ala-AAsp-(S,S)-EP-CO-Ala-NHCH$_2$Ph,
PhPr-Val-Ala-AAsp-(R,R)-EP-CO-Ala-NHCH$_2$Ph,
PhPr-Val-Ala-AAsp-(S,S)-EP-CO-Leu-NH$_2$,
PhPr-Val-Ala-AAsp-(R,R)-EP-CO-Leu-NH$_2$,
PhPr-Val-Ala-AAsp-(S,S)-EP-CO-Phe-NH$_2$,
PhPr-Val-Ala-AAsp-(R,R)-EP-CO-Phe-NH$_2$,
PhPr-Val-Ala-AAsp-(S,S)-EP-CO-Tyr-NH$_2$,
Cbz-Glu-Val-AAsp-(R,R)-EP-CO-Phe-NH$_2$,
Cbz-Glu-Val-AAsp-(S,S)-EP-CONHCH$_2$CH$_2$Ph,
Cbz-Asp-Glu-Val-AAsp-(S,S)-EP-CO-Phe-NH$_2$,
Cbz-Asp-Glu-Val-AAsp-(S,S)-EP-CONHCH$_2$Ph,
Cbz-Asp-Glu-Val-AAsp-(S,S)-EP-COOCH$_2$Ph,
Cbz-Leu-Glu-Thr-AAsp-(S,S)-EP-CONHCH$_2$CH$_2$Ph,
Cbz-Leu-Glu-Thr-AAsp-(S,S)-EP-CO-Ala-NHCH$_2$Ph,
Cbz-Ile-Glu-Thr-AAsp-(S,S)-EP-CO-Ala-NHCH$_2$Ph,

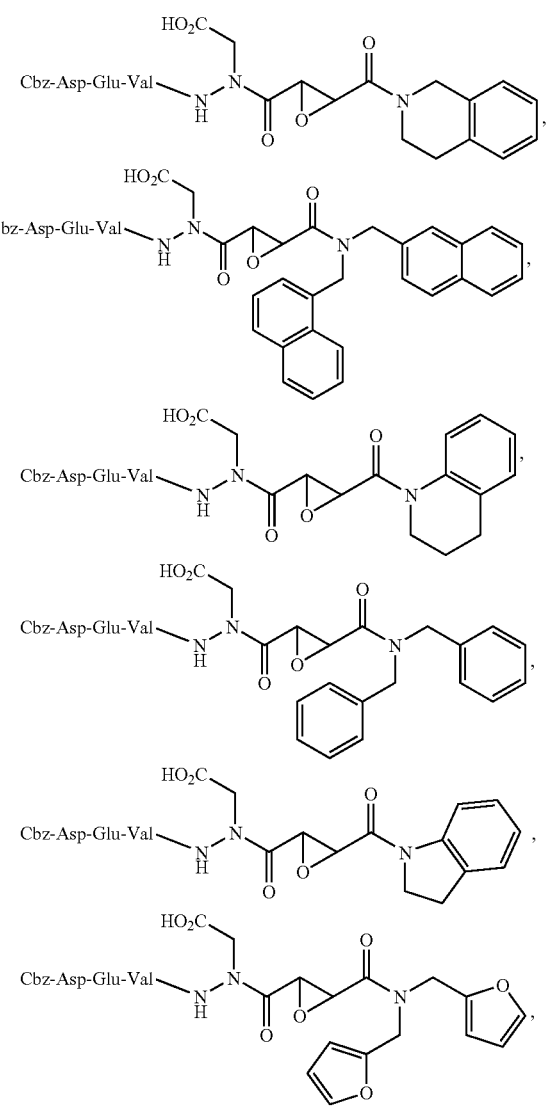

Cbz-Leu-Glu-Thr-AAsp-(S,S)-EP-COOCH$_2$Ph,
Cbz-Ile-Glu-Thr-AAsp-(S,S)-EP-COOCH$_2$Ph,
Cbz-Ile-Glu-Thr-AAsp-(R,R)-EP-COOCH$_2$Ph,
Cbz-Ile-Glu-Thr-AAsp-(R,R)-EP-CONHCH$_2$Ph.

EXEMPLARY METHODS OF PREPARATION

A. Preparation of the Epoxide Portion

A variety of epoxides can be synthesized by following the schemes shown below. Any aldehyde can be reacted with malonic acid to form the α,β-unsaturated acid, which can be further transformed into an ethyl ester. The double bond is epoxidized using t-butyl peroxide and t-butyl lithium, followed by the deblocking of the ethyl ester to yield the substituted epoxide. This epoxide can then be coupled to the respective substituted hydrazide to yield an aza-peptide epoxide using peptide coupling procedures.

The diethyl ester epoxysuccinate can also be deblocked to yield the diacid, which can be selectively coupled to different alcohols to yield a variety of epoxide monoesters. Hydrolysis of diethyl epoxysuccinate also yields the monoethyl ester, which can be coupled with a variety of monosubstituted and disubstituted amines to form amide derivatives of ethyl epoxysuccinate. The ethyl ester can then be hydrolyzed to the acid. These epoxides can then be coupled to substituted hydrazides to yield aza-peptide epoxides. These processes are illustrated below.

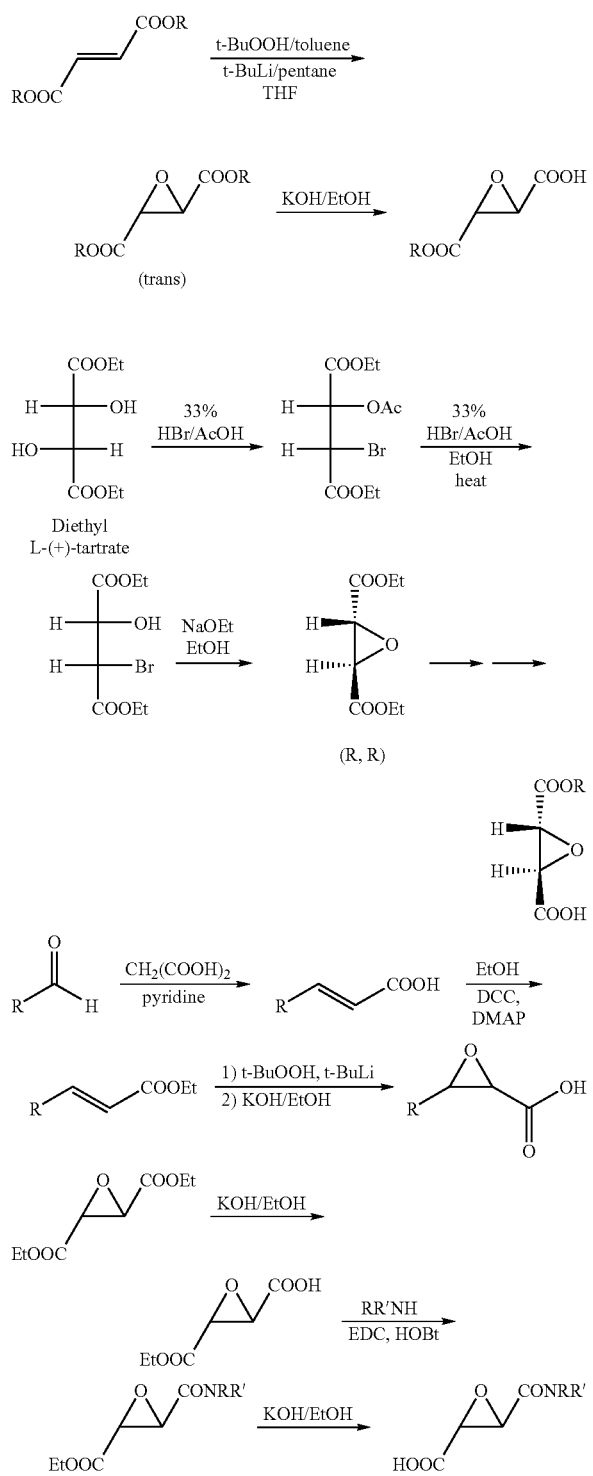

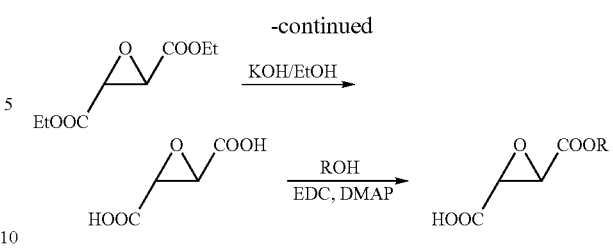

B. Preparation of the Peptide Portion

The peptide portion of the aza-peptide epoxide inhibitor can be prepared using standard peptide chemistry which is well described in publications such as *The Peptides, Analysis, Synthesis, Biology*, Vol. 1–9, published in 1979–1987 by Academic Press; Houben-Weyl Methoden der Organischen Chemie, Vol. 15, Parts 1 and 2, *Synthese von Peptiden*, published by Georg Thieme Verlag, Stuttgart in 1974; and Houben-Weyl Methods of Organic Chemistry, Vol. E22, Parts a, b, c, and d, *Synthesis of Peptides and Peptidomimetics* published by Georg Thieme Verlag, Stuttgart 2000–2003 (references incorporated herein by reference).

The $M_1$ group can be introduced using a number of different reaction schemes. First, it could be introduced directly on an amino acid as shown in the following scheme (top), or the $M_1$ group could be introduced by reaction with an amino acid ester, followed by removal of the ester group to give the same product (bottom).

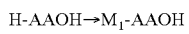

The techniques for introduction of the $M_1$ group are well documented in The Peptides, Houben-Weyel, and many other textbooks on organic synthesis. For example reaction with cyanate or p-nitrophenyl cyanate would introduce a carbamyl group ($M_1$=$NH_2CO$—). Reaction with $Me_2NCOCl$ would introduce the $Me_2NCO$— group. Reaction with p-nitrophenyl thiocarbamate would introduce a thio carbamyl group ($M_1$=$NH_2CS$—). Reaction with $NH_2SO_2Cl$ would introduce the $NH_2SO_2$— group. Reaction with $Me_2NSO_2Cl$ would introduce the $Me_2NSO_2$— group. Reaction with a substituted alkyl or aryl isocyanate would introduce the X—NH—CO— group where X is a substituted alkyl or aryl group. Reaction with a substituted alkyl or aryl isothiocyanate would introduce the X—NH—CS— group where X is a substituted alkyl or aryl group. Reaction with X—$SO_2$—Cl would introduce the X—$SO_2$— group. Reaction with a substituted alkyl or aryl acid chloride would introduce an acyl group (M=X—CO—). For example, reaction with MeO—CO—$CH_2CH_2$—CO—Cl would give the X—CO— group where X is a $C_2$ alkyl substituted with a $C_1$ alkyl-OCO— group. Reaction with a substituted alkyl or aryl thioacid chloride would introduce a thioacyl group (M=X—CS—). Reaction with a substituted alkyl or aryl sulfonyl chloride would introduce the X—$SO_2$— group. For example, reaction with dansyl chloride would give the X—$SO_2$— derivative where X was a naphthyl group mono substituted with a dimethylamino group. Reaction with a substituted alkyl or aryl chloroformate would introduce the X—O—CO— group. Reaction with a substituted alkyl or aryl chlorothioformate would introduce the X—O—CS—.

There are many alternate reaction schemes which could be used to introduce all of the above $M_1$ groups to give either $M_1$-AA-OH or $M_1$-AA-OR'.

The $M_1$-AA-OH derivatives could then be used directly in the preparation of peptide hydrazides or could be converted into the dipeptides, tripeptides, and tetrapeptides $M_1$-AA-AA-OH, $M_1$-AA-AA-AA-OH, or $M_1$-AA-AA-AA-AA-OH which could then be converted to peptide hydrazides. The substituted peptides $M_1$-AA-AA-OH, $M_1$-AA-AA-AA-OH, or $M_1$-AA-AA-AA-AA-OH could also be prepared directly from H-AA-AA-OH, H-AA-AA-AA-OH, or H-AA-AA-AA-AA-OH using the reactions described above for introduction of the $M_1$ group. Alternatively, the $M_1$ group could be introduced by reaction with carboxyl blocked peptides to give $M_1$-AA-AA-OR', $M_1$-AA-AA-AA-OR', or $M_1$-AA-AA-AA-AA-OR', followed by the removal of the blocking group R'.

C. Peparation of Peptide Hydrazides

Usually, peptide hydrazides are synthesized by reaction of an amino acid or peptide ester with hydrazine or by direct coupling of an amino acid or peptide acid with hydrazine as shown in the following two figures. They can also be synthesized directly by reaction of an amino acid or peptide ester with hydrazine.

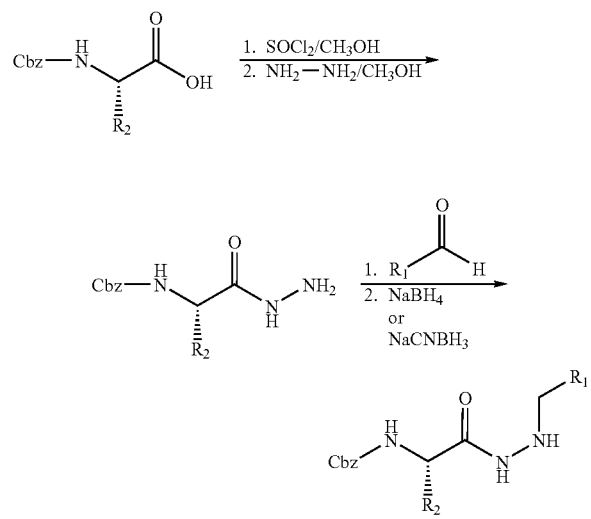

The side chain of the aza-amino acid residue can be introduced by reductive amination as shown specifically in the previous figure or by other methods known by those skilled in the art or by alkylation as shown in the following figure.

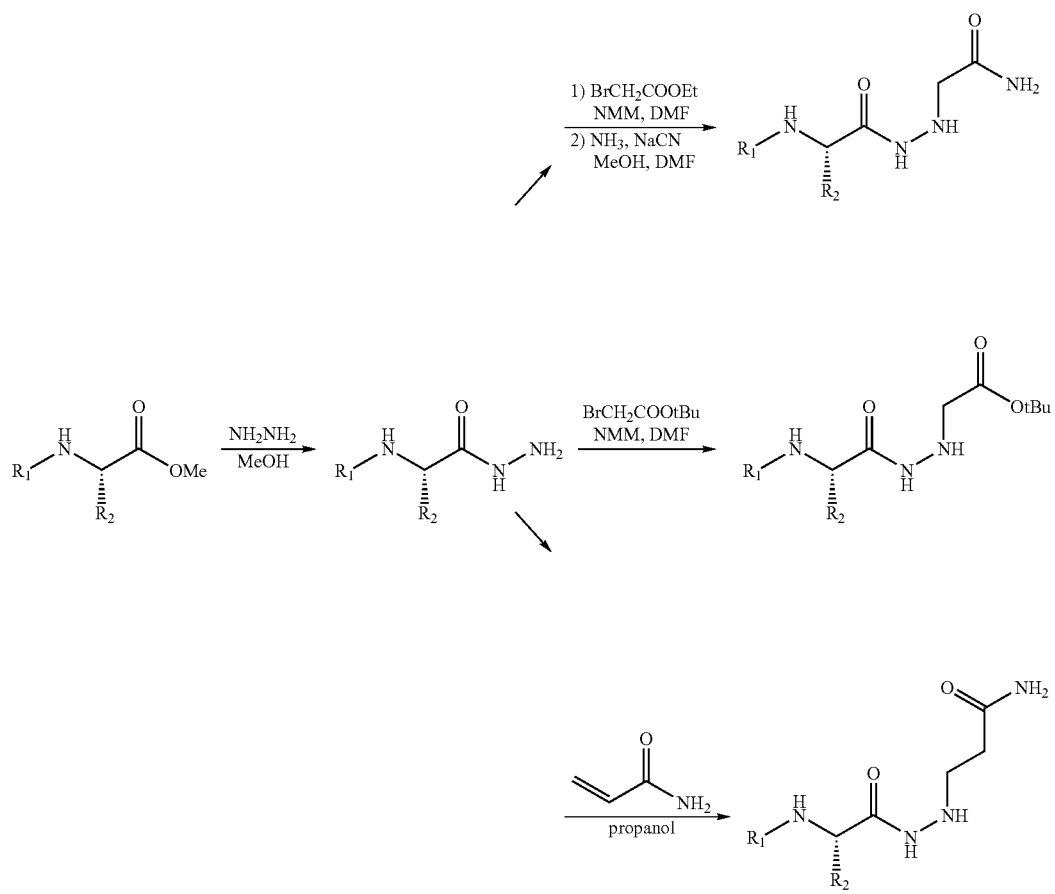

The precursors for basic side chain aza-peptide epoxides were prepared as shown in the following figure.

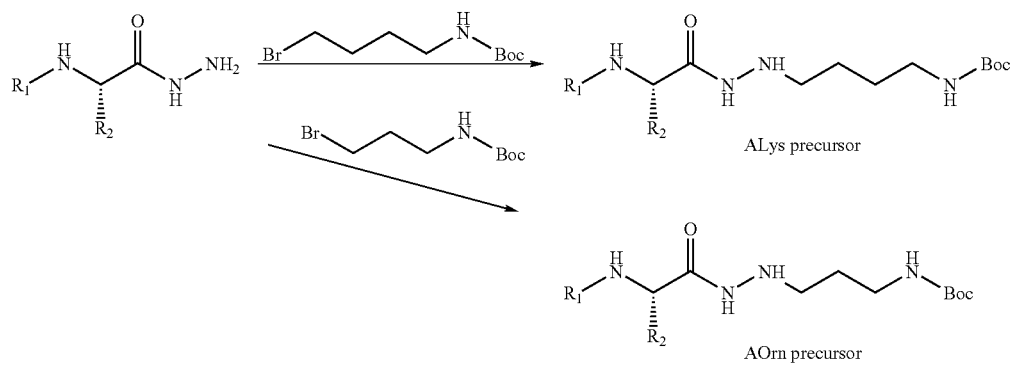

ALys precursor

AOrn precursor

D. Preparation of the Aza-peptide Epoxide 1. EDC/HOBt Coupling Method

The epoxide portion of the aza-peptide epoxide is coupled to the substituted hydrazide by reacting the epoxide portion, the substituted hydrazide, EDC, and HOBt in DMF to form the aza-peptide epoxide (see the following figure).

-continued

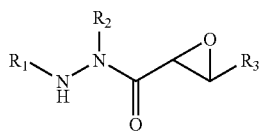

The following figure shows how these methods are used to build the AAsp and AAsn derivatives.

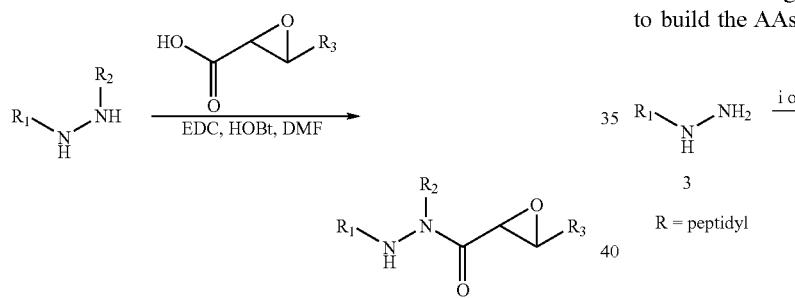

a X = OEt; b X = NH₂;
c X = Ot-Bu; d X = OH

Methods for the protection and deprotection and replacement of an amino protecting group with another moiety are well known. Deprotection of other side chain protecting groups were carried out by standard methods.

2. The Mixed Anhydride Method

Another coupling method is the mixed anhydride method. In this method, the epoxide portion of the aza-peptide epoxide is coupled to the substituted hydrazide by reacting the epoxide portion (carboxylic acid) with NMM in DMF and IBCF followed by the substituted hydrazide to form the aza-peptide epoxide (see the following figure). Methods for the protection and deprotection of side chain protecting groups are well known.

6 Y = COOEt
7 Y = COOBzl
8 Y = CH₂CH₂Ph

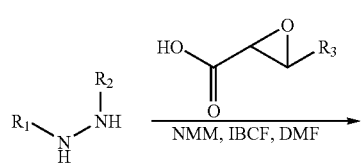

Reagents: (i) BrCH₂COOEt, NMM, DMF; NH₃/MeOH, 0.1 eq NaCN, DMF. (ii) BrCH₂COO-tBu, NMM DMF. (iii) 3, EDC, HOBt, DMF or NMM, IBCF, DMF. (iv) TFA (can be used to deblock the t-Butyl Group in certain peptides where X=O-tBu).

Examples of the preceding methods are exhibited below and in the examples:

E. Synthetic Procedures and Examples.

1. Material and Methods. Mono and dipeptidyl methyl esters were purchased from Bachem Bioscience Inc., King of Prussia, Pa. Tripeptides were synthesized using standard coupling procedures such as the mixed anhydride method. The $^1$H NMR spectra were obtained using a Varian Mercury 300 MHz spectrometer. Electrospray ionization (ESI), fast-atom-bombardment (FAB) and high-resolution mass spectrometry were performed using Micromass Quattro LC and VG Analytical 70-SE instruments. Elemental analysis was performed by Atlantic Microlab Inc., Norcross, Ga.

2. Preparation of Peptidyl Hydrazides (3). Anhydrous hydrazine (10 eq) was added to a solution of the peptidyl methyl ester (1 eq) in MeOH at room temperature, and the resulting mixture was then stirred for 16 hours. As with most hydrazides, excess hydrazine and solvent were removed by evaporation. The resulting residue was washed with ethanol and ether to give the desired peptidyl hydrazide (3) as a white solid. MS and $^1$H NMR (CDCl$_3$ or DMSO-d$_6$) were consistent with the proposed structures.

PhPr-Val-Ala-NH—NH$_2$, white solid, yield 75%.

Cbz-Asp(O-tBu)-Glu(O-tBu)-Val-NH—NH$_2$ was purified by chromatography on a silica gel column using 1:9 MeOH:CH$_2$Cl$_2$ as the eluent; white solid, yield 56%.

Cbz-Leu-Glu(O-tBu)-Thr-NH—NH$_2$, white solid, yield 97%.

N-Benzyloxycarbonylalanylalanyl Hydrazide (Cbz-Ala-Ala-NH—NH$_2$) was synthesized from Cbz-Ala-Ala-OMe by hydrazinolysis; white solid (57% yield). $^1$H NMR (DMSO-d$_6$): 1.1–1.3 (d, CH$_3$), 4.0–4.1 (m, 1H, α-H), 4.1–4.3 (m, 2H, α-H and NH), 5.05 (s, 2H, Cbz), 7.3–7.4 (m, 5H, Ph), 7.5 (d, 1H, NH), 7.9 (d, 1H, NH), 9.05 (s, 1H, NH).

Cbz-Leu-Leu-NH—NH$_2$, white solid, yield 98%.

Cbz-Val-NH—NH$_2$, white solid, yield 92%.

Cbz-Glu(O-tBu)-Val-NH—NH$_2$ was purified by chromatography on a silica gel column using 1:9 MeOH:CH$_2$Cl$_2$ as the eluent; white solid, yield 47–53%.

Cbz-Ile-Glu(O-tBu)-Thr-NH—NH$_2$, white solid, yield 91%.

3. Preparation of Cbz-Ala-Ala-NH—NH—CH$_2$COOEt (4a). Ethyl bromoacetate (1.1 eq) was added dropwise to a stirred solution of Cbz-Ala-Ala-NH—NH$_2$ (1 eq) and NMM (1.1 eq) in DMF that was cooled to −10° C. The resulting solution was stirred for 30 min at −10° C., after which the mixture was allowed to react at room temperature for 36 hours. The DMF was evaporated, and the residue was purified on a silica gel column using 1:9 MeOH:CH$_2$Cl$_2$ as the eluting solvent system to afford 4a as a white solid (yield=36%). $^1$H NMR (DMSO-d$_6$): 1.18 (t, 9H, CH$_3$), 3.5 (d, 2H, NCH$_2$COOEt), 4.0–4.15 (m, 3H, α-H and OCH$_2$CH$_3$), 4.2 (m, 1H, α-H), 5.03 (m, 2H, Cbz), 5.18 (m, 1H, NH), 7.22–7.40 (m, 5H, Ph), 7.4–7.5 (d, 1H, NH), 7.9 (m, 1H, NH), 9.35 (m, 1H, NH). MS (FAB) m/z 395 [(M+1)$^+$].

4. Preparation of N$^1$-N-Benzyloxycarbonylalanylalanyl-N$^2$-carbamoylmethylhydrazine (Cbz-Ala-Ala-NH—NH—CH$_2$CO—NH$_2$, 4b). The ethyl ester (4a) was converted to the amide (4b) by the method described by Hogberg et al. The ethyl ester Cbz-Ala-Ala-NH—NH—CH$_2$COOEt (4a, 1 eq) was dissolved in a 9 M solution of NH$_3$ in methanol and a small amount of DMF, and allowed to stir on an ice bath. To this solution was added NaCN (0.1 eq). The flask was closed with a rubber septum and allowed to stir at 0° C. for three days. The solvent was evaporated and the product was precipitated with 1:9 MeOH:CH$_2$Cl$_2$ and methanol to yield a white solid (68% yield). $^1$H NMR (DMSO-d$_6$): 1.18 (d, 6H, CH$_3$), 3.2 (d, 2H, NCH$_2$CONH$_2$), 4.0–4.12 (m, 1H, α-H), 4.2 (m, 1H, α-H), 5.03 (m, 2H, Cbz), 5.22 (m, 1H, NH), 7.18 (d, 1H, NH), 7.3–7.5 (m, 6H, Ph and NH), 8.0 (m, 1H, NH), 9.38 (m, 1H, NH). MS (FAB) m/z 366 [(M+1)$^+$]. HRMS (FAB) Calcd. For C$_{16}$H$_{24}$N$_5$O$_5$: 366.17774. Observed m/z 366.17665.

5. Preparation of Peptidyl-AA$_2$—NH—NH—CH$_2$COO-tBu (4c). Neat t-butyl bromoacetate (1 eq) was added to a stirred solution of the peptide hydrazide (3) and NMM (1 eq) in DMF pre-cooled at −10° C. The resulting solution was stirred for 30 min at −10° C., after which the mixture was allowed to react at room temperature for 20 hours. The DMF was removed by evaporation, and the resulting residue was washed with water, filtered, and dried in vacuo. Purification on a silica gel column using the appropriate solvent gave 4c (yields=48–65%). MS and $^1$H NMR (DMSO-d$_6$ or CDCl$_3$) were consistent with the proposed structure.

PhPr-Val-Ala-NH—NH—CH$_2$COO-tBu was purified by chromatography on silica gel column using 1:7 MeOH:CH$_2$Cl$_2$ as the eluent; white solid, yield 56%.

Cbz-Val-NH—NH—CH$_2$COO-tBu was purified by column chromatography on silica gel using 1:20:4.2 MeOH:CH$_2$Cl$_2$:EtOAc as the eluent; white solid, yield 64%.

$^1$H NMR (DMSO-d$_6$): 0.90 (t, 6H, Val), 1.40 (s, 9H, tBu), 1.86 (m, 1H, Val), 3.37 (d, 2H, NHCH$_2$COOH), 3.72 (t, 1H, α-H), 4.99 (s, 2H, Cbz), 5.13 (d, 1H, NH), 7.30 (s, 5H, Ph), 9.38 (d, 1H, NH).

Cbz-Asp(O-tBu)-Glu(O-tBu)-Val-NH—NH—CH$_2$COO-tBu was purified by column chromatography on silica gel using 2:18:5 MeOH:CH$_2$Cl$_2$:EtOAc as the eluent; white solid, yield 65%. MS (ESI) m/z 736.6 [(M+1)$^+$]. $^1$H NMR (DMSO-d$_6$): 0.90 (d, 6H, Val), 1.49 (s, 27H, tBu), 1.85–2.20 (m, 3H, Val and Glu), 2.21 (m, 2H, Glu), 2.40–2.70 (m, 2H, Asp CH$_2$), 3.30 and 3.38 (m, 3H, NHCH$_2$ and NHCH$_2$), 4.05–4.30 (m, 3H, α-H), 5.05 (m, 2H, Cbz), 7.20–7.40 (m, 5H, Ph), 7.60–7.95 (m, 3H, NH), 9.2 (m, 1H, NH).

Cbz-Glu(O-tBu)-Val-NH—NH—CH$_2$COO-tBu was purified by column chromatography on silica gel using 2:18:5 MeOH:CH$_2$Cl$_2$:EtOAc as the eluent; white solid, yield 78%. MS (ESI) m/z 565.3 [(M+1)$^+$]. $^1$H NMR (CDCl$_3$): 0.95 (t, 6H, Val), 1.49 (s, 18H, tBu), 1.85–2.20 (m, 3H, Val and Glu), 2.21 (m, 2H, Glu), 3.45–3.70 (m, 3H, NHCH$_2$ and NHCH$_2$), 4.25–4.30 (m, 2H, α-H), 5.05 (m, 2H, Cbz), 5.85 (d, 1H, NH), 7.05 (d, 1H, NH), 7.20–7.40 (m, 5H, Ph), 8.00 (m, 1H, NH).

Cbz-Leu-Glu(O-tBu)-Thr-NH—NH—CH$_2$COO-tBu was purified by column chromatography on silica gel using 1:9 MeOH:CH$_2$Cl$_2$ as the eluent; white solid, yield 34%. MS (ESI) m/z 680 [(M+1)$^+$]. $^1$H NMR (DMSO-d$_6$): 0.7–0.9 (t, 6H, Leu CH$_3$), 1.0 (d, 3H, Thr CH$_3$), 1–1.3 (m, 2H, Leu CH$_2$), 1.3–1.5 (m, 18H, tBu), 1.5–1.8 (m, 2H, Leu CH and Glu CH$_2$), 1.8–1.95 (m, 1H, Glu CH$_2$), 2.1–2.3 (m, 2H, Glu CH$_2$), 3.4 (d, 2H, NCH$_2$), 3.9 (m, 1H, α-H), 4.1 (m, 1H, α-H and Thr CH—OH), 4.3 (m, 1H, α-H), 4.9 (d, 1H, NH), 5.03 (m, 2H, Cbz), 7.3–7.4 (m, 5H, phenyl), 7.5 (d, 1H, NH), 7.6 (d, 1H, NH), 8.05 (d, 1H, NH), 9.2 (d, 1H, NH).

Cbz-Ile-Glu(O-tBu)-Thr-NH—NH—CH$_2$COO-tBu was purified by column chromatography on silica gel using 1:9 MeOH:CH$_2$Cl$_2$ as the eluent; white solid, yield 26%. MS (ESI) m/z 680 [(M+1)$^+$]. $^1$H NMR (DMSO-d$_6$): 0.7–0.9 (t, 6H, Ile CH$_3$), 0.9–1.0 (d, 3H, Thr CH$_3$), 1–1.2 (m, 2H, Ile CH$_2$), 1.3–1.5 (s, 18H, tBu), 1.6–1.8 (m, 2H, Ile CH and Glu CH$_2$), 1.8–1.9 (m, 1H, Glu CH$_2$), 2.1–2.3 (m, 2H, Glu CH$_2$), 3.4 (d, 2H, NCH$_2$), 3.9 (m, 2H, α-H), 4.1 (m, 1H, α-H), 4.35 (m, 1H, Thr CH—OH), 4.8 (d, 1H, NH), 5.03 (s, 2H, Cbz), 5.05 (d, 1H, NH), 7.3–7.4 (m, 5H, phenyl), 7.7 (d, 1H, NH), 8.05 (d, 1H, NH), 9.2 (s, 1H, NH).

6. Preparation of Cbz-Leu-Leu-NH—NH—$CH_2$—CH—$(CH_3)_2$— Reductive Amination Procedure. Isobutyraldehyde (1.1 eq) in THF was added dropwise to a solution of the peptidyl hydrazide Cbz-Leu-Leu-$NHNH_2$ (1 eq) in THF. The reaction mixture was stirred at room temperature for 16 hours, and monitored by TLC. The solvent was evaporated, and the resulting hydrazone was purified by column chromatography on silica gel using 1:9 MeOH:$CH_2Cl_2$ as the solvent system. The hydrazone (1 eq) in THF was reduced by the addition of $NaBH_4$ (5 eq) in a small amount of MeOH, and the mixture was monitored by TLC. The solvent was removed by evaporation and the residue was dissolved in $CH_2Cl_2$. Successive washings with saturated $NH_4Cl$ removed the excess $NaBH_4$. The organic layer was washed with saturated NaCl and dried over $MgSO_4$. The product Cbz-Leu-Leu-NH—NH—$CH_2$—CH—$(CH_3)_2$ was purified by chromatography on a silica gel column using 1:1 EtOAc:$CH_2Cl_2$ as the eluent, followed by recrystallization from MeOH/$CH_2Cl_2$/hexane to give a white solid (yield 78%). MS and $^1H$ NMR (DMSO-$d_6$ or $CDCl_3$) were consistent with the proposed structure.

7. Preparation of (2S,3S) and (2R,3R)-Oxirane-2,3-dicarboxylic Acid Monoethyl Esters (or Monoethyl Epoxysuccinates, 5, Y=COOEt). Enantiomerically pure diethyl epoxysuccinate esters (2S,3S) and (2R,3R) were synthesized from diethyl D-(−) and L-(+)-tartrate, respectively, following the general method developed by Mori and Iwasawa. This procedure involved three steps including bromination, elimination, and cyclizations. The selective hydrolysis of one ester to yield monoethyl epoxysuccinates was performed by a method similar to that described previously by Rich and Schaschke.

8. Preparation of trans-Oxirane-2,3-dicarboxylic Acid Diethyl Ester (or Diethyl Epoxysuccinate). The trans-oxirane-2,3-dicarboxylic acid diethyl ester was synthesized using a general procedure for the stereocontrolled epoxidation of α,β-unsaturated carbonyl compounds, which was similar to the method previously described by Meth-Cohn. An anhydrous solution of t-butyl hydroperoxide in toluene (3.3 M solution, 46 mL, 1.5 eq), was added to freshly distilled THF (240 mL) at −78° C. under argon. This was followed by the addition of a solution of butyl lithium in pentane (1.7 M solution, 65 mL, 1.1 eq). The mixture was stirred at −78° C. for 5 min, then a solution of diethyl fumarate (17.2 g, 0.1 M, 1 eq) in THF (50 mL) was added. The reaction mixture was stirred at room temperature for 2 hours (monitored by TLC). Sodium sulfite (10 g) was added and the mixture was stirred for 20 min. The mixture was concentrated to ca. 100 mL, diluted with ether (100 mL), filtered through yiatomaceous earth (celite), and evaporated. To the residue was added 1 M HCl (100 mL). The product trans-oxirane-2,3-dicarboxylic acid diethyl ester was extracted with EtOAc (3×100 mL), and the organic layer was washed with saturated NaCl (3×50 mL), dried over $MgSO_4$, and the solvent evaporated. Chromatography on a silica gel column with 2:3 EtOAc:hexane afforded the product trans-oxirane-2,3-dicarboxylic acid diethyl ester (yield=52%).

9. Preparation of trans-Oxirane-2,3-dicarboxylic Acid. A solution of 1 M NaOH (98 mL, 1.9 eq) was added to trans-oxirane-2,3-dicarboxylic acid diethyl ester (9.8 g, 52 mM) in MeOH (30 mL) at 0° C. The resulting solution was stirred for 1 h at 0° C., then for 30 min at room temperature, after which the solution was acidified to pH 3. Water and MeOH were evaporated. The residue was treated with EtOH (150 mL), filtered and the solvent evaporated, to give trans-oxirane-2,3-dicarboxylic acid as a colorless semisolid (yield=97%).

10. Preparation of trans-Oxirane-2,3-dicarboxylic Acid Monobenzyl Ester (5, Y=COOBzl). The reagent EDC (2.32 g, 11 mM) was added to a stirred solution of trans-oxirane-2,3-dicarboxylic acid (1.32 g, 10 mM), benzyl alcohol (1.08 g, 10 mM), and DMAP (122 mg, 1 mM) in DMF (100 mL), which has been cooled to 0° C. The resulting solution was stirred for 15 h at room temperature. After removal of DMF, the residue was purified by chromatography on two successive columns using 1:9 MeOH:$CH_2Cl_2$ as the eluent, followed by column chromatography using 1:4 MeOH:$CH_2Cl_2$ as the eluent to give 5 (Y=COOBzl), as a dark yellow oil (yield=66%). $^1H$ NMR: 3.60 (d, 1H, epoxy), 3.75 (d, 1H, epoxy), 5.18 (s, 2H, $PhCH_2O$), 7.38 (d, 5H, Ph).

11. Preparation of trans-3-Phenethyloxirane-2-carboxylic Acid (5, Y=$CH_2CH_2Ph$). A stirred solution of 3-phenylpropionaldehyde (6.7 g, 50 mM) and malonic acid (5.2 g, 50 mM) in pyridine (4 mL) was heated at 100–105° C. for 6 hours. The reaction mixture was poured onto ice/HCl. The solid precipitate was washed with water sufficiently to give 5-phenylpent-2-enoic acid (6.2 g, 35 mM, yield=70%).

The reagents DCC (33 mM) and DMAP (30 mM) were added to a solution of 5-phenylpent-2-enoic acid (5.3 g, 30 mM) in EtOH (50 mL) and THF (20 mL), which was cooled to 0° C. The resulting mixture was stirred for 30 min at 0° C., then allowed to react for 15 h at room temperature. The suspension was filtered, and the filtrate was concentrated. The residue was dissolved in EtOAc and washed with 1 M HCl (3×30 mL), $H_2O$ (10 mL), saturated $NaHCO_3$ (3×30 mL), $H_2O$ (10 mL), saturated NaCl (20 mL), dried over $MgSO_4$, and concentrated. Chromatography on a silica gel column using 1:2 EtOAc:hexane as the eluent afforded 5-phenyl-pent-2-enoic acid ethyl ester (3.75 g, yield=61%).

This compound was epoxidized using the procedure described above in the synthesis of trans-oxirane-2,3-dicarboxylic acid diethyl ester and purified on a silica gel column with 1:1 EtOAc:hexanes as the eluent to afford trans-3-phenethyloxirane-2-carboxylic acid ethyl ester as a light yellow oil (yield=46%). $^1H$ NMR: 1.25 (t, 3H, Oet); 1.90 (t, 2H, $PhCH_2CH_2$), 2.80 (t, 2H, $PhCH_2$), 3.2 (s, 2H, epoxy), 4.2 (q, 2H, Oet), 7.3 (m, 5Hb, Ph).

A solution of 1 M NaOH (1.1 eq, 5.5 mL) was added to a stirred solution of trans-3-phenethyloxirane-2-carboxylic acid ethyl ester (1.1 g, 5 mM) in MeOH (10 mL) at room temperature. After stirring for 1 h at room temperature, the solution was acidified to pH 3, and extracted with EtOAc (2×30 mL). The organic layer was washed with water (2×30 mL), saturated NaCl (20 mL), dried over $MgSO_4$, and concentrated to give trans-3-phenylethyloxirane-2-carboxylic acid (5, Y=$CH_2CH_2Ph$) as a light yellow oil (yield=72%). $^1H$ NMR: 1.90 (t, 2H, $PhCH_2CH_2$), 2.80 (t, 2H, $PhCH_2$), 3.30 (s, 2H, epoxy), 7.30 (m, 5H, Ph). HRMS (FAB) Calcd. For $C_{12}H_{12}O_5$: 237. Observed m/z 236.9.

12. General Procedure for Coupling Oxirane Dicarboxylic Acid Monoethyl Esters to Amines. The procedure used to synthesize amide derivatives of epoxysuccinate monoethyl esters was similar to that of Therrien et al (Biochemistry 2001 40 p 2702). To a solution of epoxysuccinate monoethyl ester (1 g, 6.25 mM), amine/amino acid (1.2 eq) and HOBt (1 eq) in $CHCl_3$ (30 mL) at 0° C. was added EDC (1.1 eq) slowly in 5 portions. The reaction was stirred for one hour at 0° C. and then subsequently at room temperature for 16 hours. The solvent was evaporated and the residue was partitioned between EtOAc (50 mL) and $dH_2O$ (5 mL). The organic layer was washed with 0.5 M HCl (2×10 mL), sat NaHCO$_3$ (2×50 mL), dried over MgSO$_4$ and concentrated. In general, the oxirane-2,3-dicarboxylic acid monoamides were obtained in 43–74% yield. The crude product was purified by chromatography on a silica gel column using 1:1 EtOAc:hexanes as the eluent to yield a white solid. Hydrolysis of the ester by KOH (1.2 eq) gave the desired amides (yields=65–95%).

13. (2S,3S)-3-(Dibutylcarbamoyl)oxirane-2-carboxylic Acid (HOOC-EP-CON(CH$_2$CH$_2$CH$_2$CH$_3$)$_2$). This compound was synthesized using the above procedure with dibutylamine as the starting material. $^1$H NMR (CDCl$_3$): 0.93 (t, 6H, CH$_3$), 1.32 (m, 4H, CH$_2$), 1.54 (m, 4H, CH$_2$), 3.35 (m, 4H, CH$_2$), 3.67 and 3.88 (d, 2H, epoxy).

14. (2S,3S)-3-(N-Methyl-N-benzylcarbamoyl)oxirane-2-carboxylic Acid (HOOC-EP-CON(CH$_3$)CH$_2$Ph). This compound was synthesized using the above procedure with NH(CH$_3$)CH$_2$Ph as the starting material. $^1$H NMR (CDCl$_3$): 2.94 and 3.02 (d, 3H, CH$_3$N), 3.72 and 3.96 (d, 2H, epoxy), 4.78 (d, 2H, CH$_2$Ph), 7.18–7.32 (m, 5H, Ph).

15. (2S,3S)-3-(Dibenzylcarbamoyl)oxirane-2-carboxylic Acid (HOOC-EP-CON(CH$_2$Ph)$_2$). This compound was synthesized using the above procedure with dibenzylamine as the starting material. $^1$H NMR (CDCl$_3$): 3.77 and 3.93 (d, 2H, epoxy), 4.58 (m, 4H, CH$_2$Ph), 7.14–7.36 (m, 10H, Ph).

16. Preparation of trans-3-(4-Chlorophenyl)oxirane-2-carboxylic Acid (HOOC-EP-Ph-4-Cl). The starting material, 4-chloro-trans-cinnamic acid (1 eq), was cooled to −20° C. in dry methanol. Thionyl chloride (3 eq) was added dropwise to the cooled solution over one hour. The mixture was stirred at −15° C. for an additional 30 minutes and subsequently stirred at room temperature for 24 hours. Evaporation of the volatiles yielded the methyl ester MeOOC—CH=CH-Ph-4-Cl as a white solid (yield=89%). Without further purification the methyl ester was epoxidized. An anhydrous solution of t-butyl hydroperoxide in toluene (3.3 M, 1.5 eq) was added to freshly distilled THF at −78° C. under argon. A solution of butyllithium in pentane (1.7 M, 1.1 eq) was added dropwise. The mixture was stirred at −78° C. for 5 minutes and then a solution of MeOOC—CH=CH-Ph-Cl (1 eq) in toluene was added dropwise. The reaction was stirred at −78° C. for 30 minutes then at room temperature for 16 hours. Solid sodium sulfite was added and the mixture was allowed to stir for 20 minutes, then diluted with ether and filtered over celite. The solvent was evaporated, and the crude product was purified by column chromatography on silica gel using 3:1 hexane/EtOAc as the eluent. $^1$H NMR (CDCl$_3$): 3.47 (d, 1H, epoxy), 3.83 (s, 3H, CH$_3$), 4.08 (d, 1H, epoxy), 7.21 (d, 2H, Ph), 7.33 (d, 2H, Ph). Standard deblocking of the methyl ester with sodium hydroxide (1 N) followed by acidic workup (1 N HCl) produced the 3-(4-chlorophenyl) glycidic acid. $^1$H NMR (DMSO-d$_6$): 3.65 (s, 1H, epoxy), 4.14 (s, 1H, epoxy), 7.37 (d, 2H, Ph), 7.43 (d, 2H, Ph).

17. (2S,3S)-3-(3-Methoxypropylcarbamoyl)oxirane-2-carboxylic Acid Ethyl Ester (EtOOC-EP-CONHCH$_2$CH$_2$CH$_2$OCH$_3$) was synthesized using the epoxide and amine coupling method with methoxypropylamine as the starting material. The crude product was purified by column chromatography with 1:5 MeOH:CH$_2$Cl$_2$ as the eluent. MS (ESI) m/z 232 [(M+1)$^+$].

18. (2S,3S)-3-(3-(4-Morpholinyl)propylcarbamoyl)oxirane-2-carboxylic Acid Ethyl Ester (EtOOC-EP-CONHCH$_2$CH$_2$CH$_2$morpholinyl) was synthesized using the epoxide and amine coupling method with 4-(3-aminopropyl) morpholine as the starting material. The crude product was purified by column chromatography using 1:5 MeOH:CH$_2$Cl$_2$ as the eluent (7% yield). MS (ESI) m/z 287 [(M+1)$^+$]. $^1$H NMR (CDCl$_3$): 1.2–1.4 (m, 3H, OCH$_2$CH$_3$), 2.4–2.6 (m, 6H, NCH$_2$ morph), 3.2–3.4 (m, 2H, CONHCH$_2$), 3.45 and 3.65 (m, epoxy), 3.6–3.8 (m, 4H, OCH$_2$ morph), 4.25 (m, 2H, OCH$_2$CH$_3$), 7.85 (m, 1H, NH).

19. (2S,3S)-Oxirane-2,3-dicarboxylic Acid Monobenzyl Ester (HOOC-EP-COOCH$_2$Ph). $^1$H NMR (CDCl$_3$): 3.70 (d, 2H, epoxy), 5.22 (d, 2H, CH$_2$Ph), 7.35 (m, 5H, Ph).

20. (2R,3R)-Oxirane-2,3-dicarboxylic Acid Monobenzyl Ester (HOOC-EP-COOCH$_2$Ph). $^1$H NMR (CDCl$_3$): 3.65 (d, 2H, epoxy), 5.17 (d, 2H, CH$_2$Ph), 7.32 (m, 5H, Ph).

21. (2S,3S)-Oxirane-2,3-dicarboxylic Acid Monophenethyl Ester (HOOC-EP-COOCH$_2$CH$_2$Ph). This epoxide was synthesized using the above procedure for trans-oxirane-2,3-dicarboxylic acid monobenzyl ester by using (2S,3S)-oxirane-2,3-dicarboxylic acid and phenethyl alcohol as the starting materials. $^1$H NMR (CDCl$_3$): 2.98 (t, 2H, CH$_2$), 3.65 (d, 2H, epoxy), 4.41 (m, 2H, OCH$_2$), 7.25 (m, 5H, Ph).

22. (2R,3R)-3-(2-Phenethylcarbamoyl)oxirane-2-carboxylic Acid (HOOC-(2R,3R)-EP-CONHCH$_2$CH$_2$Ph). $^1$H NMR (CDCl$_3$): 2.82 (t, 2H, CH$_2$Ph), 3.35 and 3.69 (d, 2H, epoxy), 3.54 (m, 2H, NCH$_2$), 6.20 (b, 1H, NH), 7.15–7.33 (m, 5H, Ph).

23. (2S,3S)-3-(3-Benzylcarbamoyl)oxirane-2-carboxylic Acid (HOOC-(2S,3S)-EP-CONHCH$_2$Ph). This compound was synthesized using PhCH$_2$NH$_2$ as the starting material. $^1$H NMR (CDCl$_3$): 3.53 and 3.78 (d, 2H, epoxy), 4.45 (d, 2H, CH$_2$Ph), 6.40 (b, 1H, NH), 7.25–7.33 (m, 5H, Ph).

24. (2R,3R)-3-(3-Benzylcarbamoyl)oxirane-2-carboxylic Acid (HOOC-(2R,3R)-EP-CONHCH$_2$Ph). This compound was synthesized using PhCH$_2$NH$_2$ as the starting material. $^1$H NMR (DMSO-d$_6$): 3.50 and 3.60 (d, 2H, epoxy), 4.29 (d, 2H, CH$_2$Ph), 7.23–7.33 (m, 5H, Ph), 8.89 (b, 1H, NH).

25. (2S,3S)-3-(3-Ethylcarbamoyl)oxirane-2-carboxylic Acid (HOOC-(2S,3S)-EP-CONHCH$_2$CH$_3$). This compound was synthesized using CH$_3$CH$_2$NH$_2$ as the starting material. $^1$H NMR (CDCl$_3$): 1.16 (t, 3H, CH$_3$), 3.29 (q, 2H, CH$_2$), 3.46 and 3.65 (d, 2H, epoxy), 6.10 (b, 1H, NH).

26. (2S,3S)-3-(2-Hydroxy-2-phenylethylcarbamoyl)oxirane-2-carboxylic Acid (PhCH(OH)CH$_2$NHCO-(2S,3S)-EP-COOH). This compound was synthesized using PhCH(OH)CH$_2$NH$_2$ as the starting material. $^1$H NMR (CDCl$_3$): 3.35 (m, 1H, NCH$_2$), 3.54 (m, 2H, epoxy and NCH$_2$), 3.63 (s, 1H, epoxy), 4.80 (m, 1H, OCH$_2$), 7.20 (t, 1H, NH), 7.33–7.41 (m, 5H, Ph and NH).

27. (2R,3R)-3-(2-Hydroxy-2-phenylethylcarbamoyl)oxirane-2-carboxylic Acid (PhCH(OH)CH$_2$NHCO-(2R,3R)-EP-COOH). This compound was synthesized using PhCH(OH)CH$_2$NH$_2$ as the starting material. $^1$H NMR (CDCl$_3$): 3.37 (m, 1H, NCH$_2$), 3.54 (m, 2H, epoxy and NCH$_2$), 3.63 (s, 1H, epoxy), 4.80 (m, 1H, NCH$_2$), 7.20 (t, 1H, NH), 7.33–7.41 (m, 5H, Ph and NH).

28. (2S,3S)-3-(1-Benzylcarbamoylethylcarbamoyl)oxirane-2-carboxylic Acid (HOOC-(2S,3S)-EP-CO-Ala-NH-Bzl). This compound was synthesized using NH$_2$CH(CH$_3$)CONHBzl as the starting material. $^1$H NMR (DMSO-d$_6$): 1.26 (d, 3H, Ala), 3.45 and 3.65 (d, 2H, epoxy), 4.26 (d, 2H, CH$_2$Ph), 4.33 (m, 1H, α-H), 7.19 and 7.29 (m, 5H, Ph), 8.51 (t, 1H, NH), 8.67 (d, 1H, NH).

29. (2R,3R)-3-(1-Benzylcarbamoylethylcarbamoyl)oxirane-2-carboxylic Acid (HOOC-(2R,3R)-EP-CO-Ala-NH-Bzl). This compound was synthesized using NH$_2$CH(CH$_3$)CONHBzl as the starting material. $^1$H NMR (DMSO-d$_6$): 1.25 (d, 3H, Ala), 3.49 and 3.65 (d, 2H, epoxy), 4.26 (d, 2H, CH$_2$Ph), 4.33 (m, 1H, α-H), 7.19 and 7.29 (m, 5H, Ph), 8.51 (t, 1H, NH), 8.67 (d, 1H, NH).

30. (2S,3S)-3-(1-Carbamoyl-3-methylbutylcarbamoyl)oxirane-2-carboxylic Acid (HOOC-(2S,3S)-EP-CO-Leu- NH$_2$). This compound was synthesized using NH$_2$CH(CH$_2$CH(CH$_3$)$_2$)CONH$_2$ as the starting material. $^1$H NMR (DMSO-d$_6$): 0.84 (d, 6H, CH$_3$), 1.46 (m, 2H, CH$_2$), 1.55 (m, 1H, CH), 3.48 and 3.64 (d, 2H, epoxy), 4.20 (m, 1H, α-H), 7.00 (s, 1H, NH), 7.45 (s, 1H, NH), 8.50 (d, 1H, NH).

31. (2R,3R)-3-(1-Carbamoyl-3-methylbutylcarbamoyl)oxirane-2-carboxylic Acid (HOOC-(2R,3R)-EP-CO-Leu-NH$_2$). This compound was synthesized using NH$_2$CH(CH$_2$CH(CH$_3$)$_2$)CONH$_2$ as the starting material. $^1$H NMR (DMSO-d$_6$): 0.85 (d, 6H, CH$_3$), 1.46 (m, 2H, CH$_2$), 1.56 (m, 1H, CH), 3.48 and 3.64 (d, 2H, epoxy), 4.20 (m, 1H, α-H), 7.00 (s, 1H, NH), 7.45 (s, 1H, NH), 8.50 (d, 1H, NH).

32. (2S,3S)-3-(1-Carbamoyl-2-phenylethylcarbamoyl)oxirane-2-carboxylic Acid (HOOC-(2S,3S)-EP-CO-Phe-NH$_2$). This compound was synthesized using NH$_2$CH(CH$_2$Ph)CONH$_2$ as the starting material. $^1$H NMR (DMSO-d$_6$): 2.78 (m, 1H, CH$_2$Ph), 3.02 (m, 1H, CH$_2$Ph), 3.25 and 3.56 (d, 2H, epoxy), 4.45 (m, 1H, α-H), 7.13–7.25 (m, 6H, Ph and NH), 7.57 (s, 1H, NH), 8.52 (d, 1H, NH).

33. (2R,3R)-3-(1-Carbamoyl-2-phenylethylcarbamoyl)oxirane-2-carboxylic Acid (HOOC-(2R,3R)-EP-CO-Phe-NH$_2$). This compound was synthesized using NH$_2$CH(CH$_2$Ph)CONH$_2$ as the starting material. $^1$H NMR (DMSO-d$_6$): 2.78 (m, 1H, CH$_2$Ph), 3.02 (m, 1H, CH$_2$Ph), 3.32 and 3'.59 (d, 2H, epoxy), 4.42 (m, 1H, α-H), 7.13– 7.25 (m, 6H, Ph and NH), 7.57 (s, 1H, NH), 8.60 (d, 1H, NH).

33. (2S,3S)-3-(1-Carbamoyl-2(4-hydroxyphenyl)ethylcarbamoyl)oxirane-2-carboxylic Acid (HOOC-(2S,3S)-EP-CO-Tyr-NH$_2$). This compound was synthesized using NH$_2$CH(CH$_2$Ph-4-OH)CONH$_2$ as the starting material. $^1$H NMR (CD$_3$COCD$_3$): 2.85 (m, 1H, CH$_2$Ph), 3.10 (m, 1H, CH$_2$Ph), 3.40 and 3.59 (d, 2H, epoxy), 4.60 (m, 1H, α-H), 6.50 (b, 1H, OH), 6.74 and 7.07(d of d, 4H, Ph), 7.15 (s, 1H, NH), 7.35 (d, 1H, NH).

UTILITY OF THE PRESENT INVENTION

Peptide aza-peptide epoxides are irreversible inhibitors for cysteine proteases. Peptide aza-peptide epoxides containing hydrophobic aza-amino acid residues in the P1 and/or P2 site have been found to be excellent inhibitors of cysteine proteases including cathepsin B and papain. We show that peptide aza-peptide epoxides containing aza-amino acid residues with anionic side chains in the P1 site are excellent inhibitors of caspases. Legumain is inhibited by aza-peptide expoxides with a P1 aza-asparagine residue. Clostripain and gingipain are inhibited by aza-peptide epoxides with P1 basic side chains. Peptide aza-peptide epoxides containing aza-amino acid residues with hydrophobic side chains at the P2 site have also been found to be excellent inhibitors of several cysteine proteases including papain, cathepsin B, calpain I, and calpain II. These structures may be used in vivo to treat diseases such as cancer and neurodegenerative diseases which result from the uncontrolled proteolysis by cathepsin B, calpain, caspases, and related cysteine proteases. These inhibitors may be used in vitro to prevent proteolysis which occurs in the process of production, isolation, purification, storage, or transport of peptides and proteins. These inhibitors may be useful as therapeutic agents for treatment of neurodegeneration, viral infections, muscular dystrophy, myocardial tissue damage, tumor metastasis, and bone resorption.

1. Enzyme Assays

Caspase-1. The preparation of the autolytically stable caspase-1 variant used in these studies has been described previously. Briefly, the variant contains a mutation (D381E) which renders it resistant to autolytic inactivation, but has no detectable affect on enzyme activity as compared to the naturally occurring enzyme. The enzyme variant was expressed in E. coli, purified first by immobilized metal chromatography via the N-terminal N-His tag, treated with excess oxidized glutathione to stabilize the reactive thiolate, and then re-purified by size-exclusion chromatography.

Inhibition data was measured using the progress curve assay method. Serial dilutions of each compound were prepared using an initial 8-fold dilution of a DMSO stock into HGE (100 mM HEPES,20% glycerol v/v, 0.5 mM EDTA), followed by seven serial two-fold dilutions into HGE and 12.5% DMSO, thus maintaining constant DMSO through the dilution series. Ten µL of diluted stocks or of vehicle (HGE and 12.5% DMSO) were placed in triplicate onto a 96-well microtiter plate, allowing several compounds to be tested on each plate. The plate was covered to minimize evaporation, and the plate was pre-warmed to 30° C. for 20 minutes. Enzyme was diluted into 10.0 mL of assay buffer (HGE, 5 mM DTT, plus 15 µM Ac-YVAD-AMC, 2 nM approximate final enzyme concentration), and this activated reaction mixture was added to the plate at 90 µL/well. Progress of substrate hydrolysis was monitored for 900 s in a LabSystems (Needham, Mass.) Fluoroskan Ascent fluorescent plate-reader using 385 and 460 nm excitation and emission filters, respectively, and a photomultiplier gain setting of 10. Triplicate curves were averaged and fit by nonlinear regression to the equation for irreversible inactivation shown below.

$$F(t) = F_0 + \frac{V_i(1 - e^{-k_{obs}t})}{k_{obs}}$$

where $F_0$ was routinely fixed to zero, since fluorescence values were always adjusted to an origin of 0. The second order rate constant $k_{on}$ ($M^{-1}s^{-1}$) was obtained from the slopes by linear regression, and errors represent the standard deviation of the regression slope.

Caspase-3, -6, and -8. Caspase-3, -6 and -8 were expressed in E. coli and purified according to methods previously described by Stennicke and Salvesen. Assays using the fluorogenic substrate Z-DEVD-AFC ($\lambda_{ex}$=400 nm, $\lambda_{em}$=505 nm) were carried out on a Molecular Devices fMax fluorescence microplate reader. Inhibition rates and equilibria were determined by the progress curve method. The standard 100 µL reaction was started by adding enzyme to a mixture of substrate (final concentration of Z-DEVD-AFC 100 µM) and various amounts of inhibitor in buffer (50 mM Hepes, 100 mM NaCl, 0.1% (w/v) CHAPS, sucrose 10% (w/v), and 10 mM DTT, at pH 7.4). The caspases were pre-activated for 10 min at 37° C. in the presence of 10 mM DTT.

Legumain Assays with legumain were performed as follows. A fluorometric assay for legumain has been described previously. Legumain, purified from pig kidney tissue, was assayed at 30° C. in buffer (39.5 mM citric acid, 121 mM Na$_2$HPO$_4$ at pH 5.8 containing 1 mM EDTA, 1 mM TCEP, and 0.01% CHAPS) with Cbz-Ala-Ala-Asn-AMC as the substrate (10 µM final concentration). The assays were carried out in a Perkin Elmer LS 3B fluorescence spectrometer ($\lambda_{ex}$=360 nm, $k_{em}$=460 nm) under the control of an IBM-compatible computer running the FLUSYS software. The rate of substrate hydrolysis in the absence of inhibitor was recorded, after which the inhibitor was added in a negligible volume and the new rate was monitored. Rate constants for irreversible inactivation were found by non-linear regression analysis of the pseudo first-order curves using the FLUSYS software, giving $k_{obs}$. The second-order rate constant $k_2$ was calculated as $k_{obs}/[I]$, at $[S]<K_M$. The test substrates were used at $[S]<K_M$, so no corrections for competition with the inhibitors were required. A minimum of three different concentrations of inhibitor were used to determine second-order rate constants with legumain (range used 100 µM–100 nM).

Studies with the aza-peptide epoxides using the schistosome legumain SmAE (Schistosoma mansoni asparaginyl endopeptidase) were also performed. The enzymatically pure enzyme (zymogen form) was expressed in Pichia without interference from other proteases (ref FEBS lett 2000 466 244–248 Caffrey). The actual active site enzyme concentration is unknown. The lyophilized enzyme (50–100 mg) was reconstituted in 1.5 mL 0.5 M sodium acetate, pH 4.5 containing 4 mM DTT, and left to stand at 37° C. for 3–4 hours to allow for auto-activation of the zymogen. In a black 96-well microtiter plate, 50 uL of activated enzyme was added to an equal volume of 0.1 M citrate-phosphate buffer pH 6.8 containing 4 mM DTT. Inhibitor stock solutions (20 mM) were prepared in DMSO. Serial dilutions (using water) of inhibitor were added (as 1 uL aliquots) to yield concentrations of between 2 and 0.00002 uM inhibitor. The inhibitors were preincubated with the protease at room temperature for 20 minutes before the assay ($IC_{50}$s were the same when incubated for only 5 minutes). After incubating various inhibitor concentrations with enzyme, 100 uL of the same buffer containing 20 uM substrate (Cbz-Ala-Ala-Asn-AMC) was added to the wells and the reaction monitored at room temperature with linear kinetics up to 20 minutes. Inhibitors are tested in duplicate. A plot of the RFU/min versus the inhibitor concentration [µM] permitted calculation of an $IC_{50}$ value and estimation of the $k_{obs}/[I]$.

Papain and Cathepsin B. The incubation method was used to measure the irreversible inhibition of papain and cathepsin B. With cathepsin B, 30 µL of a stock inhibitor solution was added to 300 µL of 0.1 M potassium phosphate buffer containing 1.25 mM EDTA, 0.01% Brij 35 at pH 6.0, followed by the addition of 30 µL of a freshly prepared cathepsin B solution (approximate concentration $6.98\times10^{-3}$ µg/µL) in the same potassium phosphate buffer containing 1 mM DTT (freshly prepared). Aliquots (50 µL) from the inhibition mixture were withdrawn at various time intervals and added to 200 µL of a 0.1 M potassium phosphate buffer containing 1.25 mM EDTA, 0.01% Brij 35 at pH 6.0, and the substrate Z-Arg-Arg-AMC (499 µM). The release of 7-amino-4-methylcoumarin was monitored ($\lambda_{ex}$=360 nm, $\lambda_{em}$=465 nm) using a Tecan Spectra Fluor microplate reader. Pseudo first-order inactivation rate constants were obtained from plots of ln $v_t/v_o$ versus time.

The incubation method was also used for papain. The inhibition incubation buffer for papain was 50 mM Hepes buffer at pH 7.5, containing 2.5 mM DTT and 2.5 mM EDTA. The assay used the substrate Z-Phe-Arg-pNA (53.7 µM) in the same buffer. The approximate concentration of papain added to the incubation buffer was 0.29 mg/mL. The release of p-nitroanilide was monitored at 405 nm with a Molecular Devices Thermomax microplate reader.

Aspartyl Proteases. Assays with the following aspartyl proteases were performed: porcine pepsin, human cathepsin D, plasmepsin 2 (from P. falciparum), and the secreted aspartic proteinase 2 (SAP-2) from Candida albicans. The inhibitors were also assayed with HIV-1 protease. The inhibitors were preincubated for 30 minutes with HIV-1 protease and 20 minutes with the other enzymes. Substrate was then added and the substrate hydrolysis was monitored. The following buffers were used: 0.05 M sodium acetate, 0.15 M NaCl, and 1 mM DTT for HIV-1 protease; 0.1 M sodium formate at pH 4.5 for plasmepsin-2 and SAP-2; and 0.1 M sodium formate at pH 3.5 for pepsin and cathepsin D. The inhibitor Cbz-Ala-Ala-AAsn-(2S,3S)-EP-COOEt showed almost no inhibition (less than 20% inhibition) of any of the enzymes.

Granzyme B. Assays with granzyme B were also performed. In the preliminary assays, the inhibitor (10 µL, 5 mM stock solution in DMSO) was incubated with granzyme B (90 µL) for 1 hour. After the incubation period, to these wells was added IETD-pNA (100 µL) and the rate was monitored at 405 nm. The inhibitor Cbz-Ala-Ala-AAsn-(2S, 3S)-EP-COOEt showed no inhibition.

2. Structure-Activity Relationships

Table I shows the inhibition rate constants ($k_{obs}/[I]$) for the inhibition of papain, cathepsin B, and calpain by aza-peptide epoxides. The inhibition constants are second-order rate constants and the inhibitors with the higher numbers are more potent.

TABLE I

Inhibition of Papain, Cathepsin B, and Calpain by Aza-peptide Epoxides.

| | $k_{obs}/[I]$ (M$^{-1}$ s$^{-1}$) | | |
|---|---|---|---|
| Inhibitor | papain | cathepsin B | calpain |
| Boc-Nva-AHph-trans-EP-COOEt | 1.4 | 2.7 | |
| Boc-Nle-AHph-trans-EP-COOEt | 1.6 | 1.3 | |
| Boc-Abu-AHph-trans-EP-CH$_2$CH$_2$Ph | 0.2 | NI | |
| Boc-Nle-AHph-trans-EP-CH$_2$CH$_2$Ph | 0.5 | NI | |
| Cbz-APhe-trans-EP-COOEt | 8.5 | 1.8 | |
| Cbz-APhe-trans-EP-CH$_2$CH$_2$Ph | 0.92 | | |
| Cbz-ALeu-trans-EP-COOEt | 16.1 | 4.43 | 1.75 |
| Cbz-AHph-trans-EP-COOEt | 18.8 | 8.91 | 2.44 |
| Ac-AHph-trans-EP-COOEt | 26.88 | 40.62 | 1.29 |
| Cbz-Leu-ALeu-(2S, 3S)-EP-COOEt | 10.53 | 1.8 | 8.58 |
| Cbz-Leu-ALeu-(2R, 3R)-EP-COOEt | 6.70 | NI | 1.45 |
| Cbz-Leu-ALeu-trans-EP-COOEt | 6.37 | 23.32 | 3.09 |
| Cbz-Leu-ALeu-cis-EP-COOEt | 0.38 | 6.27 | 1.88 |
| Cbz-Phe-ALeu-trans-EP-COOEt | 0.91 | 3.61 | |
| Cbz-Phe-ALeu-trans-EP-CH$_2$CH$_2$Ph | 0.7 | NI | |
| Cbz-Phe-APhe-trans-EP-CH$_2$CH$_2$Ph | 0.5 | NI | |

TABLE I-continued

Inhibition of Papain, Cathepsin B, and Calpain by Aza-peptide Epoxides.

| Inhibitor | papain | cathepsin B | calpain |
|---|---|---|---|
| Cbz-Leu-AAbu-trans-EP-COOEt | 4.94 | | 1.98 |
| Cbz-Leu-AAbu-trans-EP-COOH | 1.47 | NI | 0.57 |
| Cbz-Leu-AHph-cis-EP-COOEt | 1.03 | NI | 1.09 |
| Cbz-Leu-AHph-(2S, 3S)-EP-COOEt | 5.68 | 0.67 | 2.28 |
| Cbz-Leu-AHph-(2R, 3R)-EP-COOEt | 2.16 | NI | 2.12 |
| Cbz-Leu-AHph-(2S, 3S)-EP-COOH | | | 2.12 |
| Boc-Np2-ALeu-trans-EP-COOEt | 3.9 | 0.39 | |
| Suc-Np2-ALeu-trans-EP-COOEt | 1.39 | 0.8 | |
| Ac-Leu-AHph-trans-EP-COOEt | 1.9 | 0.59 | 0.84 |
| Ac-Leu-ALeu-trans-EP-COOEt | 2.09 | 8.0 | 1.48 |
| Cbz-Leu-Leu-ALeu-trans-EP-COOEt | 34.77 | NI | 2.65 |
| Cbz-Leu-Leu-ALeu-(2S, 3S)-EP-COOEt | 10.53 | 0.98 | 2.48 |
| Cbz-Leu-Leu-ALeu-(2R, 3R)-EP-COOEt | 20.58 | NI | NI |
| Cbz-Leu-Leu-ALeu-(2S, 3S)-EP-COOH | 6.93 | 7.02 | 0.82 |
| Cbz-Leu-Phe-AGln-trans-EP-COOEt | 0.9 | 1.3 | |
| Cbz-Leu-Phe-AGln-(2S, 3S)-EP-COOEt | | 4.73 | |
| Cbz-Leu-Phe-AGln-(2R, 3R)-EP-COOEt | | NI | |
| Cbz-Ala-Ala-AAsn-trans-EP-COOEt | 0.9 | 1.27 | |
| Cbz-Ala-Ala-AAsn-(2R, 3R)-EP-COOEt | 3 | NI | |
| Cbz-Ala-Ala-AAsn-(2S, 3S)-EP-COOEt | 4 | 6 | |
| Cbz-Ala-Ala-AAsn-cis-EP-COOEt | NI | NI | |
| Cbz-Ala-Ala-AAsn-trans-EP-COOCH$_2$Ph | | 1.09 | |
| Cbz-Ala-Ala-NHN(CH$_2$COOEt)-trans-EP-COOEt | 8.17 | 2.53 | |
| PhPr-Val-Ala-AAsp-trans-EP-COOCH$_2$Ph | <10 | <10 | |
| PhPr-Val-Ala-AAsp-trans-EP-CH$_2$CH$_2$Ph | NI | NI | |
| PhPr-Val-Ala-AAsp-(2S, 3S)-EP-COOCH$_2$Ph | | 0.81 | |
| PhPr-Val-Ala-AAsp-(2R, 3R)-EP-COOCH$_2$Ph | | NI | |
| Cbz-Asp-Glu-Val-AAsp-(2S, 3S)-EP-COOEt | NI | NI | |
| Cbz-Asp-Glu-Val-AAsp-(2R, 3R)-EP-COOEt | NI | NI | |
| Cbz-Leu-Glu-Thr-AAsp-(2S, 3S)-EP-COOEt | 0.47 | NI | |
| Cbz-Leu-Glu-Thr-AAsp-(2R, 3R)-EP-COOEt | 0.24 | NI | |
| Cbz-Ile-Glu-Thr-AAsp-(2S, 3S)-EP-COOEt | | NI | |

NI = no inhibition,
EP = epoxide,
PhPr = PhCH$_2$CH$_2$CO—.

The aza-peptide epoxide inhibitors are quite specific and do not react with serine proteases. Table II shows tests of a number of aza-peptide epoxide inhibitors with chymotrypsin. None of the aza-peptide epoxide derivatives inhibited this serine protease.

TABLE II

Inactivity of Aza-peptide Epoxides Toward Chymotrypsin.

| Inhibitor | $k_{obs}/[I]$ (M$^{-1}$ s$^{-1}$) chymotrypsin |
|---|---|
| Cbz-Asp-Glu-Val-AAsp-(2S,3S)-EP-COOEt | NI |
| Cbz-Asp-Glu-Val-AAsp-(2R,3R)-EP-COOEt | NI |
| Cbz-Leu-Glu-Thr-AAsp-(2S,3S)-EP-COOEt | NI |
| Cbz-Leu-Glu-Thr-AAsp-(2R,3R)-EP-COOEt | NI |
| PhPr-Val-Ala-AAsp-trans-EP-COOCH$_2$Ph | NI |
| PhPr-Val-Ala-AAsp-trans-EP-CH$_2$CH$_2$Ph | NI |
| Cbz-Ala-Ala-AAsn-trans-EP-COOEt | NI |
| Cbz-Ala-Ala-AAsn-(2R,3R)-EP-COOEt | NI |
| Cbz-Ala-Ala-AAsn-(2S,3S)-EP-COOEt | NI |
| Cbz-Ala-Ala-AAsn-cis-EP-COOEt | NI |

NI = no inhibition,
EP = epoxide.

Table III shows the rate of inhibition of dipeptidyl peptidase I (DPPI, cathepsin C) by aza-peptide epoxides.

TABLE III

Inhibition of DPPI by Aza-peptide Epoxides.

| Inhibitor | $k_{obs}/[I]$ (M$^{-1}$ s$^{-1}$) DPPI |
|---|---|
| Boc-Nva-AHph-trans-EP-COOEt | 0.5 |
| Boc-Nle-AHph-trans-EP-COOEt | 0.7 |
| Nva-AHph-trans-EP-COOEt.TFA | 3.2 |
| Nva-AHph-trans-EP-CH$_2$CH$_2$Ph.TFA | 0.1 |
| Nle-AHph-trans-EP-COOEt.TFA | 8.2 |

EP = epoxide.

Table IV and V show the rates of inhibition of caspases aza-peptide epoxides. Several of the inhibitors are highly effective with inhibition rate constants in the range of 300,000 to over 1 million M$^{-1}$S$^{-1}$. They also exhibit a high degree of selectivity for the target enzyme. They don't inhibit aspartyl protease, serine proteases such as granzyme B, which is also specific for a P1 Asp.

TABLE IV

Inhibition of Caspases by Aza-peptide Epoxides.

| | inhibitor | EP | $k_2$ (M$^{-1}$s$^{-1}$) caspase-1 | caspase-3 | ⑦ |
|---|---|---|---|---|---|
| 22c | Cbz-Val-AAsp-EP-COOEt | S,S | NA | 3650 ± 570 | ⑦ |
| 22n | Cbz-Val-AAsp-EP-COOH | S,S | NA | 1110 ± 340 | |
| 22a | Cbz-Val-AAsp-EP-CH$_2$CH$_2$Ph | trans | NA | 310 ± 5 | |
| 22b | Cbz-Val-AAsp-EP-Ph-4-Cl | trans | NA | 145 ± 18 | |
| 23a | PhPr-Val-Ala-AAsp-EP-CH$_2$CH$_2$Ph | trans | 300 ± 144 | NA | ⑦ |
| 23c | PhPr-Val-Ala-AAsp-EP-COOEt | S,S | 32200 ± 14560 | 1040 ± 80 | |
| | | R,R | 6290 ± 1524 | NI | |
| 23d | PhPr-Val-Ala-AAsp-EP-COOCH$_2$Ph | trans | 18070 ± 2625 | 680 ± 140 | ⑦ |
| | | S,S | 52140 ± 5295 | 1470 ± 40 | ⑦ |
| | | R,R | 1860 ± 302 | NI | |
| 23e | PhPr-Val-Ala-AAsp-EP-COOCH$_2$CH$_2$Ph | S,S | 56640 ± 9322 | 2110 ± 50 | ⑦ |
| 23f | PhPr-Val-Ala-AAsp-EP-CONHCH$_2$CH$_3$ | S,S | | 1910 ± 370 | ⑦ |
| 23g | PhPr-Val-Ala-AAsp-EP-CONHCH$_2$Ph | S,S | 65900 ± 9153 | 1610 ± 5 | ⑦ |
| | | R,R | 1630 ± 522 | NI | |
| 23h | PhPr-Val-Ala-AAsp-EP-CONHCH$_2$CH$_2$Ph | S,S | 17150 ± 2254 | 1110 ± 100 | ⑦ |
| | | R,R | 950 ± 51 | NI | |
| 23i | PhPr-Val-Ala-AAsp-EP-CONHCH$_2$CH(OH)Ph | S,S | 12260 ± 19 | 510 ± 100 | |
| | | R,R | 400 ± 19 | NI | |
| 23j | PhPr-Val-Ala-AAsp-EP-CO-Ala-NHCH$_2$Ph | S,S | 13400 | 260 ± 25 | |
| | | R,R | 268 ± 75 | NI | |
| 23k | PhPr-Val-Ala-AAsp-EP-CO-Leu-NH$_2$ | S,S | 26090±2562 | 420 ± 6 | |
| 23l | PhPr-Val-Ala-AAsp-EP-CO-Phe-NH$_2$ | S,S | 32740±9937 | 625 ± 160 | |
| | | R,R | 330 | NI | |
| 23m | PhPr-Val-Ala-AAsp-EP-CO-Tyr-NH$_2$ | S,S | 3245 ± 2330 | 87 ± 4 | |
| 24c | Cbz-Glu-Val-AAsp-EP-COOEt | S,S | 58500 | 50500 ± 2075 | 41 |
| 24l | Cbz-Glu-Val-AAsp-EP-CO-Phe-NH$_2$ | R,R | 1040 ± 455 | 470 ± 77 | |
| 24h | Cbz-Glu-Val-AAsp-EP-CONHCH$_2$CH$_2$Ph | S,S | 41070 ± 440 | 27330 ± 5430 | 31 |
| 25c | Cbz-Asp-Glu-Val-AAsp-EP-COOEt | S,S | 11840 ± 1214 | 1074440 ± 154710 | 54 |
| | | R,R | 4320 ± 830 | 464420 ± 186300 | 4 |
| 25l | Cbz-Asp-Glu-Val-AAsp-EP-CO-Phe-NH$_2$ | S,S | 9250 ± 2835 | 722180 ± 340860 | 61 |
| 25g | Cbz-Asp-Glu-Val-AAsp-EP-CONHCH$_2$Ph | S,S | 25420 ± 4013 | 1097820 ± 94860 | 60 |
| 25d | Cbz-Asp-Glu-Val-AAsp-EP-COOCH$_2$Ph | S,S | 54690 ± 15913 | 1915200 ± 209200 | 127 |
| 26c | Cbz-Leu-Glu-Thr-AAsp-EP-COOEt | S,S | 25730 | 3210 ± 315 | 86 |
| | | R,R | 19570 | 3250 ± 160 | 43 |
| 26d | Cbz-Leu-Glu-Thr-AAsp-EP-COOCH$_2$Ph | S,S | 43500 ± 2150 | 3520 ± 600 | 102 |
| 26h | Cbz-Leu-Glu-Thr-AAsp-EP-CONHCH$_2$CH$_2$Ph | S,S | NA | 2550 ± 25 | 100 |
| 26j | Cbz-Leu-Glu-Thr-AAsp-EP-CO-Ala-NHCH$_2$Ph | S,S | NA | 1280 ± 77 | 66 |
| 27c | Cbz-Ile-Glu-Thr-AAsp-EP-COOEt | S,S | 12372 | 4080 ± 360 | 4577 |
| | | R,R | 13260±3684 | 2630 ± 365 | 340 |
| 27d | Cbz-Ile-Glu-Thr-AAsp-EP-COOCH$_2$Ph | S, S | 45788 | 9545 ± 960 | 862 |
| | | R,R | 13000±980 | 3115 ± 125 | 454 |
| 27g | Cbz-Ile-Glu-Thr-AAsp-EP-CONHCH$_2$Ph | R,R | 18140±4085 | 6475 ± 240 | 601 |
| 27j | Cbz-Ile-Glu-Thr-AAsp-EP-CO-Ala-NHCH$_2$Ph | S,S | NA | 3050 | 382 |

PhPr = Ph-CH$_2$—CH$_2$—CO—,
NI = no inhibition,
EP = epoxide,
AAsp = aza-Asp,
Cbz = Ph-CH$_2$—CO—.

TABLE V

Inhibition of Caspases by Aza-peptide Epoxides with Disubstituted Amides.

| | inhibitor | EP | $k_2$ (M$^{-1}$s$^{-1}$) caspase-1 | caspase-3 | caspase-6 |
|---|---|---|---|---|---|
| 10-129 | PhPr-Val-Ala-AAsp-EP-CON(CH$_2$CH$_2$CH$_2$CH$_3$)$_2$ | S, S | 26150 ± 5460 | 520 ± 10 | 53 ± 9 |
| 10-127 | PhPr-Val-Ala-AAsp-EP-CON(CH$_2$Ph)$_2$ | S, S | 101140 ± 9547 | 830 ± 40 | 145 ± 1 |
| 11-4 | Cbz-Leu-Glu-Thr-AAsp-EP-CON(CH$_2$Ph)$_2$ | S, S | NA | 2750 ± 205 | 13840 ± 270 |
| 11-11 | Cbz-Ile-Glu-Thr-AAsp-EP-CON(CH$_2$Ph)$_2$ | S, S | NA | 3550 | 32000 ± 1680 |
| 11-16 | Cbz-Leu-Glu-Thr-AAsp-EP-CON(CH$_3$)CH$_2$Ph | S, S | NA | 2640 ± 100 | 9680 ± 875 |
| 11-17 | PhPr-Val-Ala-AAsp-EP-CON(CH$_3$)CH$_2$Ph | S, S | NA | 1950 ± 150 | 136 |
| 11-18 | Cbz-Ile-Glu-Thr-AAsp-EP-CON(CH$_3$)CH$_2$Ph | S, S | NA | 4780 | 47730 ± 420 |

TABLE VI

Inhibition of Legumain by Aza-peptide Epoxides.

| inhibitor | $R_3$ | Stereochemistry | Schistosome Legumain $IC_{50}$ (nM) |
|---|---|---|---|
| 12a | COOEt | S,S | 53 ± 25 |
| | COOEt | R,R | 788 ± 88 |
| | COOEt | trans | |
| | COOEt | cis | |
| 12b | COOCH$_2$Ph | S,S | 47 ± 33 |
| | COOCH$_2$Ph | trans | |
| 12c | COOCH$_2$CH$_2$Ph | S,S | 45 |
| 12d | CONHCH$_2$Ph | S,S | NI |
| 12e | CONHCH$_2$CH$_2$Ph | S,S | NI |
| 12f | CO-Ala-NH-Bzl | R,R | NI |
| 12g | CON(nBu)$_2$ | S,S | 68 ± 4 |
| 12h | CON(CH$_3$)CH$_2$Ph | S,S | 63 ± 11 |
| 12i | CH$_2$CH$_2$Ph | trans | 70 ± 14 |
| 12j | Ph-4-Cl | trans | 90 ± 0 |

NI = no inhibition.

Legumain is inhibited by a variety of AAsn derivatives which are either not inhibitors for-caspases or very poor. Both Schistosome and pig kidney legumain are inhibited.

Overall, the aza-peptide epoxide inhibitors have worked with every cysteine protease we have tested. The rates are higher with cysteine proteases that belong to clan CD compared to clan CA.

3. Inhibition Mechanism

The active site of cysteine proteases contains a cysteine and a histidine residue. The proposed mechanism involves the attack of the active site cysteine residue on the epoxide functional group to form a covalent adduct. An example of a caspase inhibitor is shown in the following figure. The enzyme recognizes the P1 AAsp residue and inhibition occurs. Additional interactions would occur between the extended substrate binding site of the cysteine protease and the inhibitor which would increase the binding affinity and specificity of the inhibitors.

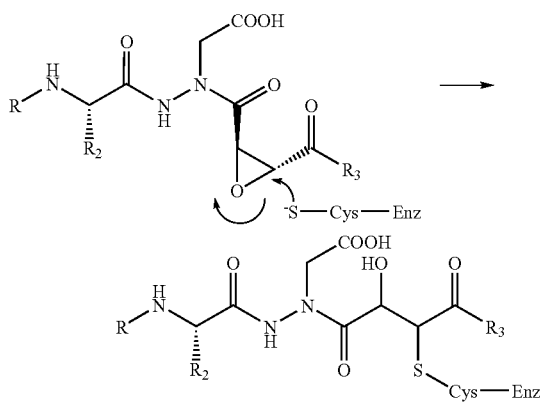

The peptide and amino acid aza-peptide epoxide derivatives, as shown above, bind to the enzymes using many of the interactions that are found in complexes of a particular enzyme with its substrates and/or inhibitors. Additional interactions with the enzyme can be obtained by tailoring the $R_3$ group of the inhibitor to imitate the amino acid residues which are preferred by an individual protease at the S1' and S2 subsites. For example, aza-peptide epoxides with $R_3$ phenylalkyl groups would interact effectively with caspase-1, which is shown to prefer such structures in alpha-ketoamide peptide inhibitors. Likewise, the $M_1$ group can interact with the S subsites of the target cysteine protease. Once a good inhibitor structure for a particular enzyme is found, it is then possible to change other characteristics such as solubility or hydrophobicity by adding substituents to the $M_1$ or $R_1$ and $R_2$ groups.

The following structures are inhibitors for the listed enzymes. The inhibitor sequences were obtained from peptide substrate and/or inhibitor sequences in the protease literature.

| | |
|---|---|
| Cl—C$_6$H$_4$CH$_2$OCO-Phe-AGly-EP-COOH | for papain |
| C$_6$H$_5$CH$_2$NHCO-Gly-Phe-AGly-EP-COOH | for cathepsin B |
| Morpholine-CO-2-Naphthyl-AHph-EP-COOEt | for cathepsin S |
| 2-Naphthyl-SO$_2$-Ile-ATrp-EP-COOH | for cathepsin B |
| 1-Naphthyl-SO$_2$-Val-ATrp-EP-COOH | for cathepsin B and L |
| Pro-Phe-AArg-EP-COOH | for cathepsin B and L |
| Cbz-Phe-Leu-Leu-AMet(O$_2$)-EP-COOH | for cathepsin K |
| Ph-CH$_2$—SO$_2$-AAsp-EP-COOCH$_2$Ph | for caspase-1 |
| Ph-CH$_2$CHFCO-Val-Ala-AAsp-EP-COOCH$_2$Ph | for caspase-1 |
| 4-Cl-PhCH$_2$CH$_2$CO-Val-Ala-AAsp-EP-COOCH$_2$Ph | for caspase-1 |
| 4-NO$_2$-PhCH$_2$CH$_2$CO-Val-Ala-AAsp-EP-COOCH$_2$Ph | for caspase-1 |
| 4-CH$_3$O-PhCH$_2$CH$_2$CO-Val-Ala-AAsp-EP-COOCH$_2$Ph | for caspase-1 |
| 3-F-PhCH$_2$CH$_2$CO-Val-Ala-AAsp-EP-COOCH$_2$Ph | for caspase-1 |
| 3,4-dichloro-PhCH$_2$CH$_2$CO-Val-Ala-AAsp-EP-COOCH$_2$Ph | for caspase-1 |
| Naphthyl-CH$_2$OCO-Val-Ala-AAsp-EP-COOCH$_2$Ph | for caspase-1 |
| 4-CF$_3$-PhCH$_2$CH$_2$CO-Val-Ala-AAsp-EP-COOCH$_2$Ph | for caspase-1 |
| 4-CH$_3$-PhCH$_2$CH$_2$CO-Val-Ala-AAsp-EP-COOCH$_2$Ph | for caspase-1 |
| PhCH$_2$NHCO-Val-Ala-AAsp-EP-COOCH$_2$Ph | for caspase-1 |
| 4-HO-PhCH$_2$CH$_2$CO-Val-Ala-AAsp-EP-COOCH$_2$Ph | for caspase-1 |
| 4-Cl-Ph-CH$_2$OCO-Leu-Glu-Thr-AAsp-EP-COOEt | for caspase-8 |
| 4-Cl-Ph-CH$_2$OCO-Ile-Glu-Thr-AAsp-EP-COOEt | for caspase-8 |
| 4-Cl-Ph-CH$_2$OCO-Asp-Glu-Val-AAsp-EP-COOEt | for caspase-3 |
| C$_5$H$_9$-OCO-Asp-Glu-Val-AAsp-EP-COOEt | for caspase-3 |
| 3-F-Ph-CH$_2$OCO-Ala-Ala-AAsn-EP-COOEt | for legumain |
| 4-PhO-PhCH$_2$OCO-Ala-Ala-AAsn-EP-COOEt | for legumain |
| 3-F-Ph-CH$_2$OCO-Leu-Glu-Thr-AAsp-EP-COOEt | for caspase-6 |
| PhCH$_2$CO-Val-Ala-AAsp-EP-COO(CH$_2$)$_2$Ph-4-Cl | for caspase-1 |
| Cbz-Leu-Glu-Thr-AAsp-EP-COO(CH$_2$)$_2$Ph-4-CH$_3$ | for caspase-8 |
| Cbz-Leu-Glu-Thr-AAsp-EP-COOCH$_2$C$_6$H$_{11}$ | for caspase-8 |
| Cbz-Asp-Glu-Val-AAsp-EP-COO(CH$_2$)$_2$C$_6$H$_4$-p-OCH$_3$ | for caspase-3 |
| Cbz-Ala-Ala-AAsn-EP-COO(CH$_2$)$_2$-2-naphthyl | for legumain |
| PhCH$_2$CH$_2$CO-Val-Ala-AAsp-EP-(CH$_2$)$_2$Ph-3-F | for caspase-1 |
| PhCH$_2$CH$_2$CO-Val-Ala-AAsp-EP-COO(CH$_2$)$_2$-2-naphthyl | for caspase-1 |
| Cbz-Leu-Glu-Thr-AAsp-EP-COO(CH$_2$)$_2$C$_6$H$_4$-p-NO$_2$ | for caspase-6 |
| Cbz-Ala-Ala-AAsn-EP-COO(CH$_2$)$_2$C$_6$H$_4$-p-CN | for legumain |
| PhCH$_2$CH$_2$CO-Val-Ala-AAsp-EP-COO(CH$_2$)$_2$C$_6$H$_4$-m-OPh | for caspase-1 |
| 2,4-dinitrophenyl-Ahx-Gly-Phe-AAla-EP-COOH | for cathepsin L |
| Cbz-Leu-ALys-EP-COOEt | gingipain |
| Cbz-Leu-AOrn-EP-COOEt | gingipain |
| Cbz-Leu-ALys-EP-COOEt | clostripain |
| Cbz-Leu-AOrn-EP-COOEt | clostripain |
| Cbz-Lys(Biotinyl)-Val-Ala-AAsp-EP-COOEt | caspase-1 |

4. In Vitro Uses

To use the above inhibitors in vitro, they are dissolved in an organic solvent such as dimethylsulfoxide or ethanol, and are added to an aqueous solution containing serine and/or cysteine proteases. The final concentration of the organic solvent should be less than 25%. The inhibitors may also be added as solids or in suspension. The cysteine protease inhibitors of this invention would be useful in a variety of experimental procedures where proteolysis is a significant problem. Inclusion of these inhibitors in radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast, and human cells to produce a purified cloned product in higher yield.

The novel compounds of this invention are effective in the prevention of unnecessary proteolysis caused by cysteine proteases in the process of purification, transport and storage of peptides and proteins as shown in Table I–VI by effective inhibition of many cysteine proteases.

Diagnostic Reagents

Aza-peptide epoxides of the present invention can be used for the identification of proteases, for example novel cysteine proteases. One embodiment provides a method for screening a sample for the presence of a protease, particularly a cysteine protease, by contacting the sample with an aza-peptide epoxide, for example an aza-peptide epoxide of Formula I, and detecting the presence of the the aza-peptide epoxide-protease conjugate. Detection of the conjugate may be accomplished using known techniques. For example, aza-peptide epoxides of the present invention can be modified with a detectable label including but not limited to a radioisotope, fluorescent marker, biotin, antibody, enzyme conjugate such as horseradish peroxidase, or the like. The aza-peptide conjugates can be fixed to a support, for example using known chemical fixatives, and a sample can then by added to the aza-peptide epoxide. Such support can be microarrays or the like. The fixed aza-peptide epodixe can then irreverisible or reveribsibly bind a protease, for example a cysteine protease, in the sample. The support can be washed to remove excess sample. The aza-peptide epoxide-protease conjugate can then be eluted from the support and the protease can be detected or identified using conventional techniques. The support can be any durable substance including but not limited to metal, plastic, glass, quartz or the like. The aza-peptide epoxides can be linked to the support with a linker, for example a cleavable linker to facilliate the removal of aza-peptide epoxide-protease conjugates.

5. In Vivo Uses

Effective inhibitors of the proteolytic function of caspases (Table IV and V) can be used to treat a variety of diseases. Excessive cell death can result from acquired or genetic conditions which increase the accumulation of signals that induce apoptosis or that diminish the threshold at which such events induce apoptosis. Excessive apoptosis has been associated with a variety of disease states including neuro-degenerative disorders, ischemic injuries, acquired immunodeficiency syndrome (AIDS), and osteoporosis. Apoptosis is involved in amyotrophic lateral sclerosis (ALS), Huntington's disease, Alzheimer's disease, Parkinson's disease, and spinal muscular atrophy. In multiple sclerosis (MS), the death of the oligodendrocytes is an important example of the glial degeneration through apoptosis.

Huntingtin, the first protein identified as a neurodegenerative disease, is a substrate for proteolytic cleavage by caspase-3. Thus, aza-peptide epoxides would be useful for the treatment of Huntington's disease and other neurodegenerative diseases such as dentatorubropallidoluysian atrophy (DRPLA), spinocerebellar atrophy type 3 (SCA-3), and spinal bulbar muscular atrophy (SBMA).

Effector caspases cleave Alzheimer's gene products, presenilins 1 and 2 proteins. Recently, it has been shown that caspase-6 is involved in human neuronal cell apoptosis, amyloidogenesis, and Alzheimer's disease. Amyloid β peptide (Aβ), which builds up in the brains of people with Alzheimer's disease, causes cultured neurons to die by apoptosis. Thus effective caspase-6 aza-peptide epoxide inhibitors (Table IV and V) can be used for the treatment of Alzheimer's disease.

In models related to Parkinson disease, peptide caspase inhibitors protect against 1-methyl-4-phenylpyridinium (MPP$^+$)-induced apoptosis of cultured cerebellar granular neurons and increase the rate of survival. Also, in mice overexpressing Bcl-2, dopaminergic 1-methyl-4-phenyl-1,2,3,6-tetrahydropyridine (MPTP) caspase activity is blocked, toxicity is decreased, and substantial nigra neurons survive. Thus, effective caspase aza-peptide epoxide inhibitors (Table IV) can be used for the treatment of Parkinson's disease.

Neuronal apoptosis is also seen after acute injuries such as stroke, trauma, and ischemia. Apoptosis has been observed in striatal and cortical neurons in animal models of stroke. Transgenic mice, expressing a caspase-1 inhibitor, are protected from ischemic damage after middle cerebral artery occlusion. During ischemia, activated caspases dismantle the cell by cleaving multiple substrates such as the enzymes essential for cell repair and cytoskeletal proteins. Therefore, caspase activation develops in models of global ischemia and may accompany the ischemic component of head injury. The effect of irreversible inhibitors (Z-VAD-FMK, Z-DEVD-FMK, and YVAD-CMK) on ischemia-induced tissue shows that caspase-1 and caspase-3 are involved in the mechanism of cell death in ischemic and excitotoxic brain injury. Caspases are recognized as novel therapeutic targets for central nervous diseases in which cell death occurs mainly by the mechanism of apoptosis. Thus effective caspase aza-peptide epoxide inhibitors (Table IV and V) can be used for the treatment of many diseases involving apoptosis.

Legumain is involved in Schistosomiasis (blood flukes) and in immune disorders. Thus, legumain inhibitors can be used to treat Schistosomiasis and many immunological problems. Gingipain is involved in periodontal disease and thus gingipain inhibitors can be use to treat periodontal disease. Clostripain inhibitors should be useful as antibacterial agents. Separin inhibitors can be use to treat disease which involve cell mitosis.

Aza-peptide epoxides can be used to control protein turnover, muscular dystrophy, myocardial tissue damage, tumor metastasis, and bone resorption as shown in Table I by effective inhibition of lysosomal cathepsin B in buffer. Peptide aza-peptide epoxides can also be used as neuroprotectants or for the treatment of ischemia, stroke, or Alzheimer's disease as shown in Table I by effective inhibition of calpain I and calpain II.

6. Drug Delivery

This invention also provides a pharmaceutical composition which comprises a compound according to Formula I and a pharmaceutically accepted carrier, dilutent or excipient. Accordingly, the compounds of Formula I may be used in the manufacture of a medicament. For therapeutic use, the peptide aza-peptide epoxides may be administered orally, topically, or parenterally. The term parenteral, as used, includes subcutaneous injection, intravenous, intramuscular, intrastemal injection, or infusion techniques. The dosage depends primarily on the specific formulation and on the object of the therapy or prophylaxis. The amount of the individual doses as well as the administration is best determined by individually assessing each case.

The pharmaceutical compositions containing the active ingredient may be in a form suitable for oral use, for example, as tablets, troches, lozenges, aqueous or oily suspensions, dispersible powders or granules, emulsions, hard or soft capsules, syrups, or elixirs. Dosage levels of the order of 0.2 mg to 140 mg per kilogram of body weight per day are useful in the treatment of the above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the peptide aza-peptide epoxides or their pharmaceutically acceptable salts will normally be in the dosage range from 0.2 to 140 mg/kg of body weight. Administration is made by intravenous, intramuscular, or subcutaneous injection. Accordingly, pharmaceutical compositions for parenteral administration will contain from about 10 mg to 7 gms of the compounds per dose. In addition to the active ingredient, these pharmaceutical compositions will usually contain a buffer, e.g. a phosphate buffer which keeps the pH in the range from 3.5 to 7 and sodium chloride, mannitol, or sorbitol for adjusting the isotonic pressure.

A composition for topical application can be formulated as an aqueous solution, lotion, jelly or an oily solution or suspension. A composition in the form of an aqueous solution is obtained by dissolving the compounds of this invention in aqueous buffer solution of pH 4 to 6.5 and, if desired, adding a polymeric binder. An oily formulation for topical application is obtained by suspending the compounds of this invention in an oil, optionally with the addition of a swelling agent such as aluminium stearate and/or a surfactant.

EXAMPLES

The following detailed examples are given to illustrate the invention and are not intended to limit it in any manner.

Example 1

EDC/HOBt Coupling Method. trans-3-($N^2$-(N-3-Phenyl-propanoylvalylalanyl)-$N^1$-t-butoxycarbonylmethylhydrazinocarbonyl)oxirane-2-carboxylic Acid Benzyl Ester (PhPr-Val-Ala-AAsp(O-tBu)-trans-EP-COOCH$_2$Ph). To a stirred solution of monobenzyl epoxysuccinate 5 (Y=COOBzl), HOBt, and PhPr-Val-Ala-NH—NH—CH$_2$COO-tBu in DMF, was added EDC. The mixture was allowed to react for 16 h at room temperature. The DMF was evaporated, and the residue was treated with EtOAc (20 mL). The organic layer was washed with 2% citric acid (2×20 mL), saturated NaHCO$_3$ (2×20 mL), H$_2$O (10 mL), saturated NaCl (10 mL), dried over MgSO$_4$, and concentrated. Chromatography on silica gel column using 1:19 MeOH:CH$_2$Cl$_2$ as eluent afforded PhPr-Val-Ala-AAsp(O-tBu)-trans-EP-COOCH$_2$Ph as white solid, yield=36%. MS and $^1$H NMR (CDCl$_3$) was consistent with the proposed structures.

Example 2

Pentafluorophenol Coupling Method. (2R,3R)-3-($N^2$-(N-Benzyloxycarbonylleucyl-t-butoxyglutamylthreonyl)-$N^1$-t-butoxycarbonylmethylhydrazinocarbonyl)oxirane-2-carboxylic Acid Ethyl Ester (Cbz-Leu-Glu(O-tBu)-Thr-AAsp(O-tBu)-(2R,3R)-EP-COOEt). Coupling of Cbz-Leu-Glu(O-tBu)-Thr-NH—NH—CH$_2$COO-tBu with 5 (Y=COOEt) was accomplished using the pentafluorophenol method. The epoxide 5 (1 eq, Y=COOEt) in DMF was reacted with pentafluorophenol (1 eq) and DCC (1 eq) in DMF at 0° C. The reaction was allowed to reach room temperature and then was stirred for 24 hours. Dicyclohexylurea was removed by filtration and the filtrate was evaporated to dryness under reduced pressure. The peptide Cbz-Leu-Glu(O-tBu)-Thr-NH—NH—CH$_2$COO-tBu (1 eq) in DMF was added to the residue and the reaction was allowed to stir at room temperature for 24 hours. The solvent was evaporated and the product was purified by chromatography using two silica gels columns, the first column with 1:9 MeOH:CH$_2$Cl$_2$ as the eluent, followed by another column with 2:1 EtOAc:hexane as the eluent; white solid, yield 16%. MS and $^1$H NMR (CDCl$_3$) were consistent with the proposed structure.

Example 3

Mixed Anhydride Coupling Method. Coupling of bulky peptides, such as Z-Asp(O-tBu)-Glu(O-tBu)-Val-NH—NH$_2$—COO-tBu and Cbz-Leu-Glu(O-tBu)-Thr-NH—NH—CH$_2$COO-tBu, with 5 (Y=COOEt), was accomplished using the mixed anhydride method. To a solution of 5 (5 eq) in DMF at 0° C. was added N-methylmorpholine (NMM, 5 eq) followed isobutyl chloroformate (IBCF, 5 eq). After the reaction mixture was allowed to stir for 30 min, the substituted hydrazide (1 eq) dissolved in DMF was added to the mixture. After 10 min the ice bath was removed and the reaction was stirred for 16 hr at room temperature. The DMF was evaporated and the residue was washed and purified using the same procedure as described above for the EDC/HOBT coupling. MS and $^1$H NMR (DMSO-d$_6$ or CDCl$_3$) were consistent with the proposed structures. Examples 3A-3C were prepared using this mixed anhydride method.

Example 3A

Cbz-Asp(O-tBu)-Glu(O-tBu)-Val-AAsp(O-tBu)-(2S,3S)-EP-COOEt was purified using column chromatography on silica gel using 2:18:5 MeOH:CH$_2$Cl$_2$:EtOAc as the eluent; white solid, yield 58%.

Example 3B

Cbz-Asp(O-tBu)-Glu(O-tBu)-Val-AAsp(O-tBu)-(2R,3R)-EP-COOEt was purified using column chromatography on silica gel using 2:18:5 MeOH:CH$_2$Cl$_2$:EtOAc as the eluent; white solid, yield 57%.

Example 3C

Cbz-Leu-Glu(O-tBu)-Thr-AAsp(O-tBu)-(2S,3S)-EP-COOEt was purified by chromatography on two successive columns, using 1:13 MeOH:CH$_2$Cl$_2$ as the eluent, followed by column chromatography using 2:1 EtOAc:hexane as the eluent; white solid, yield 44%.

Example 3D

PhPr-Val-Ala-AAsp(O-tBu)-(2S,3S)-EP-CON(nBu)$_2$ was obtained using the EDC/HOBt coupling method, purified by column chromatography on silica gel with 19:1 CH$_2$Cl$_2$:MeOH as the eluent, and then rechromatographed using 50:45:5 CH$_2$Cl$_2$:EtOAc:MeOH as the eluent; white solid, yield 38%. $^1$H NMR (CDCl$_3$): 0.85 and 0.95 (m, 12H, Val and n-butyl CH$_3$), 1.35 (m, 7H, Ala CH$_3$ and CH$_2$), 1.45 (s, 9H, tBu), 1.60 (m, 4H, CH$_2$), 2.00 (m, 1H, Val CH), 2.55 (m, 2H, PhCH$_2$), 2.95 (m, 2H, PhCH$_2$CH$_2$), 3.20 (s, 2H, AAsp CH$_2$COOH), 3.35 (m, 4H, CH$_2$N), 3.80 (d, 2H, epoxy), 4.20 (m, 2H, α-H), 6.20 (s, 1H, NH), 7.10–7.25 (m, 5H, Ph), 7.60 (b, 1H, NH), 9.25 (b, 1H, NH).

Example 3E

PhPr-Val-Ala-AAsp(O-tBu)-(2S,3S)-EP-CON(CH$_3$)Bzl was obtained using the EDC/HOBt coupling method, purified by column chromatography on silica gel with 19:1 CH$_2$Cl$_2$:MeOH as the eluent, and then rechromatographed using 50:45:5 CH$_2$Cl$_2$:EtOAc:MeOH as the eluent; white solid, yield 39%. $^1$H NMR (CDCl$_3$): 0.86 (m, 6H, Val CH$_3$), 1.30 (m, 3H, Ala CH$_3$), 1.45 (s, 9H, tBu), 2.00 (m, 1H, Val CH), 2.55 (m, 2H, PhCH$_2$), 2.94 (m, 3.5H, PhCH$_2$CH$_2$CO and CH$_3$N), 3.10 (s, 1.5H, CH$_3$N), 3.20 (s, 2H, AAsp CH$_2$COOH), 3.70 (d, 2H, epoxy), 4.18 (m, 2H, α-H), 4.62 (m, 2H, PhCH$_2$N), 6.20 (b, 1H, NH), 7.10–7.35 (m, 10H, Ph), 7.60 (b, 1H, NH), 9.40 (b, 1H, NH).

Example 3F

PhPr-Val-Ala-AAsp(O-tBu)-(2S,3S)-EP-CON(Bzl)$_2$ was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 40%. $^1$H NMR (CDCl$_3$): 0.84 (m, 6H, Val CH$_3$), 1.33 (m, 3H, Ala CH$_3$), 1.46 (s, 9H, tBu), 2.00 (m, 1H, Val CH), 2.55 (m, 2H, PhCH$_2$), 2.93 (m, 2H, PhCH$_2$CH$_2$CO), 3.20 (m, 2H, AAsp CH$_2$COOH), 3.80 (s, 2H, epoxy), 4.20 (m, 2H, α-H), 4.62 (m, 4H, PhCH$_2$N), 6.20 (b, 1H, NH), 7.10–7.40 (m, 15H, Ph), 7.45 (b, 1H, NH), 9.20 (s, 1H, NH).

Example 3G

Cbz-Leu-Glu(O-tBu)-Thr-AAsp(O-tBu)-(2S,3S)-EP-CON(CH$_3$)Bzl was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 53%. $^1$H NMR (CDCl$_3$): 0.93 (t, 6H, Leu CH$_3$), 1.18 (m, 3H, Thr CH$_3$), 1.27 (m, 2H, Leu CH$_2$), 1.46 (s, 18H, tBu), 1.85 (m, 1H, Leu CH), 2.15 (m, 2H, Glu CH$_2$), 2.45 (m, 2H, Glu CH$_2$), 3.10 (m, 3H, NCH$_3$), 3.20 (s, 2H, AAsp CH$_2$), 3.76 (d, 2H, epoxy), 4.25 (m, 3H, α-H), 4.45 (m, 1H, Thr CH), 4.70 (s, 2H, CH$_2$Ph), 5.12 (q, 2H, Z), 7.10–7.40 (m, 12H, Ph and NH), 7.95 (b, 1H, NH), 9.45 (b, 1H, NH).

Example 3H

Cbz-Leu-Glu(O-tBu)-Thr-AAsp(O-tBu)-(2S,3S)-EP-CON(Bzl)$_2$ was obtained using the EDC/HOBt coupling method, purified by column chromatography on silica gel with 19:1 CH$_2$Cl$_2$:MeOH as the eluent, and then rechromatographed using 50:45:5 CH$_2$Cl$_2$:EtOAc:MeOH as the eluent; white solid, yield 41%. $^1$H NMR (Acetone-d$_6$): 0.91 (t, 6H, Leu CH$_3$), 1.16 (m, 3H, Thr CH$_3$), 1.30 (m, 2H, Leu CH$_2$), 1.45 (s, 18H, tBu), 1.65 (m, 1H, Leu CH), 1.95 and 2.15 (d of m, 2H, Glu CH$_2$), 2.40 (m, 2H, Glu CH$_2$), 2.87 (d, 2H, AAsp CH$_2$), 3.80 (d, 2H, epoxy), 4.25–4.45 (m, 4H, α-H and Thr CH), 4.66 (m, 4H, CH$_2$Ph), 5.10 (q, 2H, Z), 6.80 (d, 1H, NH), 7.20–7.40 (m, 15H, Ph), 7.45 (d, 1H, NH), 7.78 (d, 1H, NH), 9.70 (s, 1H, NH).

Example 3I

Cbz-Ile-Glu(O-tBu)-Thr-AAsp(O-tBu)-(2S,3S)-EP-CO—N(CH$_3$)Bzl was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 42%. $^1$H NMR (CDCl$_3$): 0.92 (t, 6H, Ile CH$_3$), 1.16 (m, 5H, Thr CH$_3$ and Ile CH$_2$), 1.45 (m, 19H, tBu and Ile CH), 1.90 and 2.10 (d of m, 2H, Glu CH$_2$), 2.45 (m, 2H, Glu CH$_2$), 3.00 (m, 3H, NCH$_3$), 3.22 (s, 2H, AAsp CH$_2$), 3.76 (s, 2H, epoxy), 4.20 (m, 3H, α-H), 4.40 (d, 1H, Thr CH), 4.50 (m, 2H, CH$_2$Ph), 5.11 (q, 2H, Z), 7.10–7.40 (m, 12H, Ph and NH), 7.85 (b, 1H, NH), 9.50 (b, 1H, NH).

Example 3J

Cbz-Ile-Glu(O-tBu)-Thr-AAsp(O-tBu)-(2S,3S)-EP-CO—N(Bzl)$_2$ was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 37%. $^1$H NMR (CDCl$_3$): 0.90 and 1.00 (m, 6H,Ile CH$_3$), 1.14 (d, 3H, Thr CH$_3$), 1.19 (m, 2H, Ile CH$_2$), 1.45 (m, 19H, tBu and Ile CH), 1.90 and 2.10 (d of m, 2H, Glu CH$_2$), 2.45 (m, 2H, Glu CH$_2$), 3.21 (s, 2H, AAsp CH$_2$), 3.80 (s, 2H, epoxy), 4.15 (b, 1H, α-H), 4.30 (m, 2H, α-H), 4.45–4.60 (m, 5H, Thr CH and CH$_2$Ph), 5.10 (s, 2H, Z), 7.10–7.40 (m, 17H, Ph and NH), 7.85 (d, 1H, NH), 9.50 (s, 1H, NH).

Example 3K

PhPr-Val-Ala-AAsp(O-tBu)-(2S,3S)-EP-COOEt was obtained using the EDC/HOBt coupling method and purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 31%. $^1$H NMR (CDCl$_3$): 0.84 (m, 6H, Val CH$_3$), 1.34 (m, 6H, Ala CH$_3$ and OEt), 1.44 (s, 9H, tBu), 2.00 (m, 1H, Val CH), 2.58 (m, 2H, PhCH$_2$), 2.97 (t, 2H, PhCH$_2$CH$_2$CO), 3.65 (s, 2H, AAsp CH$_2$), 3.62 and 3.91 (d, 2H, epoxy), 4.23 (m, 4H, α-H and OEt), 6.00 (d, 1H, NH), 6.60 (d, 1H, NH), 7.16–7.30 (m, 5H, Ph), 9.05 (s, 1H, NH).

Example 3L

PhPr-Val-Ala-AAsp(O-tBu)-(2R,3R)-EP-COOEt was obtained using the EDC/HOBt coupling method and purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 69%. $^1$H NMR (CDCl$_3$): 0.82 (m, 6H, Val CH$_3$), 1.30 (t, 3H, OEt), 1.37 (d, 2H, Ala CH$_3$), 1.46 (s, 9H, tBu), 2.00 (m, 1H, Val CH), 2.58 (m, 2H, PhCH$_2$), 2.97 (t, 2H, PhCH$_2$CH$_2$CO), 3.22 (s, 2H, AAsp CH$_2$), 3.62 and 3.95 (d, 2H, epoxy), 4.23 (m, 4H, α-H and OEt), 6.20 (d, 1H, NH), 6.70 (d, 1H, NH), 7.16–7.27 (m, 5H, Ph), 9.10 (s, 1H, NH).

Example 3M

PhPr-Val-Ala-AAsp(O-tBu)-(2S,3S)-EP-COOCH$_2$Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 56%. $^1$H NMR (CDCl$_3$): 0.82 (m, 6H, Val CH$_3$), 1.26 (m, 3H, Ala CH$_3$), 1.42 (s, 9H, tBu), 2.00 (m, 1H, Val CH), 2.56 (m, 2H, PhCH$_2$), 2.93 (m, 2H, PhCH$_2$CH$_2$CO), 3.67 (s, 2H, AAsp CH$_2$), 3.75 and 3.94 (d, 2H, epoxy), 4.20 and 4.35 (m, 2H, α-H), 5.19 (m, 2H, Benzyl), 6.20 (d, 1H, NH), 6.75 (d, 1H, NH), 7.15–7.37 (m, 10H, Ph), 9.25 (s, 1H, NH).

Example 3N

PhPr-Val-Ala-AAsp(O-tBu)-(2R,3R)-EP-COOCH$_2$Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 48%. $^1$H NMR (CDCl$_3$): 0.82 (m, 6H, Val CH$_3$), 1.26 (m, 3H, Ala CH$_3$), 1.42 (s, 9H, tBu), 2.00 (m, 1H, Val CH), 2.56 (m, 2H, PhCH$_2$), 2.95 (m, 2H, PhCH$_2$CH$_2$CO), 3.62 (s, 2H, AAsp CH$_2$), 3.70 and 3.94 (d, 2H, epoxy), 4.20 and 4.35 (m, 2H, α-H), 5.20 (m, 2H, Benzyl), 6.25 (d, 1H, NH), 6.75 (d, 1H, NH), 7.15–7.37 (m, 10H, Ph), 9.30 (s, 1H, NH).

Example 3O

PhPr-Val-Ala-AAsp(O-tBu)-(2S,3S)-EP-COOCH$_2$CH$_2$Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 61%. $^1$H NMR (CDCl$_3$): 0.83 (m, 6H, Val CH$_3$), 1.34 (d, 3H, Ala CH$_3$), 1.45 (s, 9H, tBu), 2.00 (m, 1H, Val CH), 2.58 (m, 2H, PhCH$_2$), 2.96 (m, 4H, PhCH$_2$CH$_2$CO and PhCH$_2$), 3.63 (s, 2H, AAsp CH$_2$), 3.75 and 3.90 (d, 2H, epoxy), 4.35 (m, 4H, α-H and OCH$_2$), 6.20 (m, 1H, NH), 7.85 (d, 1H, NH), 7.12–7.30 (m, 10H, Ph), 9.20 (s, 1H, NH).

Example 3P

PhPr-Val-Ala-AAsp(O-tBu)-(2S,3S)-EP-CONHCH$_2$CH$_3$ was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 62%. $^1$H NMR (Acetone-d$_6$): 0.88 (m, 6H, Val CH$_3$), 1.10 (t, 3H, CH$_3$), 1.35 (d, 3H, Ala CH$_3$), 1.46 (s, 9H, tBu), 2.00 (m, 1H, Val CH), 2.61 (m, 2H, PhCH$_2$), 2.82 (s, 2H, AAsp CH$_2$), 2.95 (t, 2H, PhCH$_2$CH$_2$CO), 3.25 (m, 2H, CH$_2$N), 3.41 (s, 2H, epoxy), 4.20 and 4.40 (m, 2H, α-H), 7.15 (b, 1H, NH), 7.25 (m, 6H, Ph and NH), 7.40 (b, 1H, NH), 7.60 (d, 1H, NH).

Example 3Q

PhPr-Val-Ala-AAsp(O-tBu)-(2S,3S)-EP-CONHCH$_2$Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 49%. $^1$H NMR (CDCl$_3$): 0.82 (m, 6H, Val CH$_3$), 1.32 (m, 3H, Ala CH$_3$), 1.45 (s, 9H, tBu), 2.00 (m, 1H, Val CH), 2.53 (m, 2H, PhCH$_2$), 2.93 (m, 2H, PhCH$_2$CH$_2$CO), 3.65 (d, 2H, AAsp CH$_2$), 3.62 and 3.79 (d, 2H, epoxy), 4.15 (m, 2H, α-H), 4.43 (m, 2H, PhCH$_2$N), 6.35 (b, 1H, NH), 6.90 (b, 1H, NH), 7.00 (b, 1H, NH), 7.13–7.31 (m, 10H, Ph), 9.40 (s, 1H, NH).

Example 3R

PhPr-Val-Ala-AAsp(O-tBu)-(2R,3R)-EP-CONHCH$_2$Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 48%. $^1$H NMR (CDCl$_3$): 0.82 (m, 6H, Val CH$_3$), 1.32 (m, 3H, Ala CH$_3$), 1.46 (s, 9H, tBu), 2.00 (m, 1H, Val CH), 2.57 (m, 2H, PhCH$_2$), 2.95 (m, 2H, PhCH$_2$CH$_2$CO), 3.68 (d, 2H, AAsp CH$_2$), 3.62 and 3.80 (d, 2H, epoxy), 4.20 (m, 2H, α-H), 4.40 (m, 2H, PhCH$_2$N), 6.20 (b, 1H, NH), 6.70 (b, 1H, NH), 7.00 (b, 1H, NH), 7.13–7.31 (m, 10H, Ph), 9.20 (s, 1H, NH).

Example 3S

PhPr-Val-Ala-AAsp(O-tBu)-(2S,3S)-EP-CONHCH$_2$CH$_2$Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 47%. $^1$H NMR (CDCl$_3$): 0.83 (m, 6H, Val CH$_3$), 1.35 (m, 3H, Ala CH$_3$), 1.43 (s, 9H, tBu), 2.05 (m, 1H, Val CH), 2.56 (t, 2H, PhCH$_2$), 2.78 (t, 2H, PhCH$_2$CH$_2$N), 2.95 (t, 2H, PhCH$_2$CH$_2$CO), 3.40 and 3.53 (d of m, 2H, AAsp CH$_2$), 3.53 and 3.69 (d, 2H, epoxy), 4.20 (m, 2H, α-H), 4.45 (m, 2H, NCH$_2$CH$_2$Ph), 6.30 (d, 1H, NH), 6.40 (t, 1H, NH), 7.00 (d, 1H, NH), 7.13–7.31 (m, 10H, Ph), 9.30 (s, 1H, NH).

Example 3T

PhPr-Val-Ala-AAsp(O-tBu)-(2R,3R)-EP-CONHCH$_2$CH$_2$Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 41%. $^1$H NMR (CDCl$_3$): 0.83 (m, 6H, Val CH$_3$), 1.35 (m, 3H, Ala CH$_3$), 1.43 (s, 9H, tBu), 2.05 (m, 1H, Val CH), 2.56 (t, 2H, PhCH$_2$), 2.78 (t, 2H, PhCH$_2$CH$_2$N), 2.95 (t, 2H, PhCH$_2$CH$_2$CO), 3.48 and 3.70 (d of m, 2H, AAsp CH$_2$), 3.53 and 3.65 (d, 2H, epoxy), 4.17 (m, 2H, α-H), 4.43 (m, 2H, NCH$_2$CH$_2$Ph), 6.30 (d, 1H, NH), 6.40 (t, 1H, NH), 6.80 (d, 1H, NH), 7.15–7.35 (m, 10H, Ph), 9.20 (s, 1H, NH).

Example 3U

PhPr-Val-Ala-AAsp(O-tBu)-(2S,3S)-EP-CONHCH$_2$CH(OH)Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 33%. $^1$H NMR (Acetone-d$_6$): 0.86 (m, 6H, Val CH$_3$), 1.38 (m, 3H, Ala CH$_3$), 1.46 (s, 9H, tBu), 2.05 (m, 1H, Val CH), 2.49 (m, 2H, PhCH$_2$), 2.90,(m, 4H, PhCH$_2$CH$_2$ and AAsp CH$_2$), 3.55 (d, 2H, epoxy), 3.45 and 3.60 (d of m, 2H, NCH$_2$), 4.20 and 4.37 (m, 2H, α-H), 4.85 (t 1H, CH), 7.15–7.40 (m, 12H, Ph and NH), 7.80 (b, 1H, NH), 7.90 (m, 1H, NH).

Example 3V

PhPr-Val-Ala-AAsp(O-tBu)-(2R,3R)-EP-CONHCH$_2$CH(OH)Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 37%. $^1$H NMR (Acetone-d$_6$): 0.86 (m, 6H, Val CH$_3$), 1.40 (m, 3H, Ala CH$_3$), 1.46 (s, 9H, tBu), 2.05 (m, 1H, Val CH), 2.45 (m, 2H, PhCH$_2$), 2.90 (m, 4H, PhCH$_2$CH$_2$ and AAsp CH$_2$), 3.40 and 3.60 (d of m, 2H, NCH$_2$), 3.60 and 3.76 (d, 2H, epoxy), 4.20 and 4.35 (m, 2H, α-H), 4.80 (b, 1H, CH), 7.00–7.40 (m, 12H, Ph and NH), 7.80 (b, 2H, NH).

Example 3W

PhPr-Val-Ala-AAsp(O-tBu)-(2S,3S)-EP-CO-Ala-NHBzl was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 41%. $^1$H NMR (Acetone-d$_6$): 0.87 (m, 6H, Val CH$_3$), 1.37 (m, 6H, Ala CH$_3$), 1.46 (s, 9H, tBu), 2.05 (m, 1H, Val CH), 2.63 (m, 2H, PhCH$_2$), 2.87 (s, 2H, AAsp CH$_2$), 2.93 (t, 2H, PhCH$_2$CH$_2$CO), 3.55 (s, 2H, epoxy), 4.15 and 4.45 (m, 3H, α-H), 4.43 (d, 2H, PhCH$_2$N), 7.15 (d, 1H, NH), 7.20–7.30 (m, 10H, Ph), 7.40 (d, 1H, NH), 7.75 (s, 1H, NH), 8.00 (b, 2H, NH).

Example 3X

PhPr-Val-Ala-AAsp(O-tBu)-(2R,3R)-EP-CO-Ala-NHBzl was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 50%. $^1$H NMR (Acetone-d$_6$): 0.87 (m, 6H, Val CH$_3$), 1.37 (m, 6H, Ala CH$_3$), 1.46 (s, 9H, tBu), 2.05 (m, 1H, Val CH), 2.60 (m, 2H, PhCH$_2$), 2.87 (s, 2H, AAsp CH$_2$), 2.90 (t, 2H, PhCH$_2$CH$_2$CO), 3.65 (s, 2H, epoxy), 4.25 (m, 3H, α-H), 4.40 (d, 2H, PhCH$_2$N), 7.15 (d, 1H, NH), 7.20–7.30 (m, 10H, Ph), 7.40 (d, 1H, NH), 7.80–8.00 (m, 3H, NH).

Example 3Y

PhPr-Val-Ala-AAsp(O-tBu)-(2S,3S)-EP-CO-Leu-NH$_2$ was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 23%. $^1$H NMR (DMSO-d$_6$): 0.86–0.96 (m, 12H, Val and Leu CH$_3$), 1.37 (d, 3H, Ala CH$_3$), 1.46 (t, 9H, tBu), 1.65 (m, 2H, Leu CH$_2$), 1.75 (m, 1H, Leu CH), 2.05 (m, 1H, Val CH), 2.63 (m, 2H, PhCH$_2$), 2.86 (s, 2H, AAsp CH$_2$), 2.94 (t, 2H, PhCH$_2$CH$_2$CO), 3.57 (s, 2H, epoxy), 4.19, 4.35 and 4.50 (m, 3H, α-H), 7.15 (d, 1H, NH), 7.25 (s, 5H, Ph), 7.35 (s, 1H, NH), 7.45 (d, 1H, NH), 7.80 (d, 1H, NH), 8.15 (d, 1H, NH), 9.75 (s, 1H, NH).

Example 3Z

PhPr-Val-Ala-AAsp(O-tBu)-(2R,3R)-EP-CO-Leu-NH$_2$ was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 64%. $^1$H NMR (DMSO-d$_6$): 0.86–0.96 (m, 12H, Val and Leu CH$_3$), 1.37 (d, 3H, Ala CH$_3$), 1.45 (t, 9H, tBu), 1.65 (m, 2H, Leu CH$_2$), 1.75 (m, 1H, Leu CH), 2.05 (m, 1H, Val CH), 2.60 (m, 2H, PhCH$_2$), 2.88 (s, 2H, AAsp CH$_2$), 2.90 (t, 2H, PhCH$_2$CH$_2$CO), 3.50 (d, 2H, epoxy), 4.20, 4.40 and 4.45 (m, 3H, α-H), 7.15 (d, 1H, NH), 7.25 (s, 5H, Ph), 7.45 (b, 2H, NH), 7.80 (b, 2H, NH), 9.90 (s, 1H, NH).

Example 3AA

PhPr-Val-Ala-AAsp(O-tBu)-(2S,3S)-EP-CO-Phe-NH$_2$ was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 39%. $^1$H NMR (Acetone-d$_6$): 0.88 (m, 6H, Val CH$_3$), 1.39 (d, 3H, Ala CH$_3$), 1.46 (s, 9H, tBu), 2.05 (m, 1H, Val CH), 2.60 (m, 2H, PhCH$_2$), 2.83 (s, 2H, AAsp CH$_2$), 2.95 (m, 3H, Phe PhCH$_2$ and PhCH$_2$CH$_2$CO), 3.20 (m, 1H, Phe PhCH$_2$), 3.50 (d, 2H, epoxy), 4.20 and 4.35 (m, 2H, α-H), 4.65 (m, 1H, Phe α-H), 7.15–7.35 (m, 11H, Ph and NH), 7.50 (s, 1H, NH), 7.80 (d, 1H, NH), 7.95 (d, 1H, NH), 8.15 (b, 1H, NH), 9.80 (s, 1H, NH).

Example 3BB

PhPr-Val-Ala-AAsp(O-tBu)-(2R,3R)-EP-CO-Phe-NH$_2$ was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 56%. $^1$H NMR (Acetone-d$_6$): 0.88 (m, 6H, Val CH$_3$), 1.37 (d, 3H, Ala CH$_3$), 1.46 (s, 9H, tBu), 2.05 (m, 1H, Val CH), 2.58 (m, 2H, PhCH$_2$), 2.83 (s, 2H, AAsp CH$_2$), 2.93 (m, 2H, PhCH$_2$CH$_2$CO), 3.00 and 3.40 (d of m, 2H, Phe PhCH$_2$), 3.45 (d, 2H, epoxy), 4.25 and 4.35 (m, 2H, α-H), 4.65 (m, 1H, Phe α-H), 7.15–7.35 (m, 11H, Ph and NH), 7.40 (d, 1H, NH), 7.50 (b, 1H, NH), 8.00 (b, 1H, NH), 8.60 (b, 1H, NH), 9.80 (s, 1H, NH).

Example 3CC

PhPr-Val-Ala-AAsp(O-tBu)-(2S,3S)-EP-CO-Tyr-NH$_2$ was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 50%. $^1$H NMR (Acetone-d$_6$): 0.87 (m, 6H, Val CH$_3$), 1.35 (d, 3H, Ala CH$_3$), 1.45 (s, 9H, tBu), 2.05 (m, 1H, Val CH), 2.60 (m, 2H, PhCH$_2$), 2.88 (s, 2H, AAsp CH$_2$), 2.94 (m, 3H, Tyr PhCH$_2$ and PhCH$_2$CH$_2$CO), 3.10 (m, 1H, Tyr PhCH$_2$), 3.72 (d, 2H, epoxy), 4.30 and 4.55 (m, 3H, α-H), 6.50 (s, 1H, NH), 6.75 (d, 2H, Ph), 7.15 (m, 5H, Ph), 7.20 (d, 2H, Ph), 7.30 (d, 1H, NH), 7.50 (d, 1H, NH), 7.80 (d, 1H, NH), 8.20 (d, 2H, NH).

Example 3DD

Cbz-Val-AAsp(O-tBu)-(2S,3S)-EP-COOEt was obtained using the EDC/HOBt coupling method, and purified by column chromatography on silica gel with 1:20:4.2 MeOH:$CH_2Cl_2$:EtOAc as the eluent; white solid, yield 51%. MS (ESI) m/z 522.2 [(M+1)$^+$]. $^1$H NMR (CDCl$_3$): 0.95–1.02 (m, 6H, Val), 1.28 (t, 3H, OCH$_2$CH$_3$), 1.63 (s, 9H, tBu), 2.05 (m, 1H, Val), 3.62 (s, 1H, epoxy), 3.97 (d, 2H, NHCH$_2$COOH), 4.15 (t, 1H, α-H), 4.25 (q, 2H, OCH$_2$CH$_3$), 5.12 (m, 2H, Cbz), 7.35 (s, 5H, Ph), 8.61 (s, 1H, NH).

Example 3EE

Cbz-Val-AAsp(O-tBu)-trans-EP-CH$_2$CH$_2$Ph was obtained using the EDC/HOBt coupling method, and purified by column chromatography on silica gel with 1:50:51 MeOH:CH$_2$Cl$_2$:EtOAc as the eluent; white solid, yield 48%. HRMS (FAB) Calcd. for $C_{30}H_{39}N_3O_7$: 553.27878. Observed m/z 553.28663. $^1$H NMR (CDCl$_3$): 0.90–1.04 (d, 6H, Val), 1.46 (s, 9H, tBu), 1.78–1.96 (d, 2H, CH$_2$CH$_2$Ph), 2.00–2.14 (m, 1H, Val), 2.66–2.87 (m, 2H, CH$_2$CH$_2$Ph), 3.16 (t, 1H, epoxy), 3.53 (s, 1H, NHCH$_2$COOH), 3.85 (t, 1H, α-H), 4.81 (d, 1H, NH), 4.99–5.20 (m, 2H, Cbz), 7.13–7.37 (m, 10H, Ph), 8.25 (s, 1H, NH).

Example 3FF

Cbz-Val-AAsp(O-tBu)-trans-EP-Ph-4-Cl was obtained using the EDC/HOBt coupling method, and purified by column chromatography on silica gel with 1:100:100 MeOH:CH$_2$Cl$_2$:EtOAc as the eluent; white solid, yield 51%. MS (ESI) m/z 560.4 [(M+ 1)$^+$]. $^1$H NMR (DMSO-d$_6$): 0.64–0.92 (d, 6H, Val), 1.20 (s, 9H, tBu), 1.84 (m, 1H, Val), 3.68 (m, 1H, NHCH$_2$COOH), 3.75 (s, 1H, epoxy), 4.05 (d, 1H, α-H), 4.80–5.09 (s, 2H, Cbz), 7.18–7.46 (m, 9H, Ph), 11.02 (m, 1H, NH).

Example 3GG

Cbz-Glu(O-tBu)-Val-AAsp(O-tBu)-(2S,3S)-EP-CONHCH$_2$CH$_2$Ph was obtained using the EDC/HOBt coupling method, purified by column chromatography on silica gel with 7:13:1:1 hexane:EtOAc:MeOH:CH$_2$Cl$_2$ as the eluent, and then rechromatographed using 3:1 EtOAc:hexane as the eluent; white solid, yield 35%. MS (ESI) m/z 782.4 [(M+1)$^+$]. $^1$H NMR (CDCl$_3$): 0.95 (d, 6H, Val), 1.45 (s, 18H, tBu), 1.90–2.30 (m, 3H, Val and Glu), 2.45 (m, 2H, Glu), 2.72 (t, 2H, NHCH$_2$CH$_2$Ph), 3.40 and 3.60 (m, 2H, NHCH$_2$CH$_2$Ph), 3.50 and 3.8 (d, 2H, epoxy), 4.10–4.30 (m, 4H, NCH$_2$ andα-H), 5.10 (m, 2H, Cbz), 6.10 and 6.25 (m, 2H, NH), 7.20–7.40 (m, 5H, Ph), 9.00 (m, 1H, NH).

Example 3HH

Cbz-Asp(O-tBu)-Glu(O-tBu)-Val-AAsp(O-tBu)-(2S,3S)-EP-COOCH$_2$Ph was obtained using the mixed anhydride coupling method, and purified using column chromatography on silica gel using 5:1:19 EtOAc:MeOH:CH$_2$Cl$_2$ as the eluent; white solid, yield 23%. MS (ESI) m/z 940.5 [(M+ 1)$^+$]. $^1$H NMR (CDCl$_3$): 0.85 (m, 6H, Val), 1.35 (m, 27H, tBu), 1.80–2.24 (m, 3H, Val and Glu), 2.41 (m, 2H, Glu), 2.65–2.90 (m, 2H, Asp), 3.60 and 4.00 (d, 2H, epoxy), 4.05–4.12 (m, 2H, NCH$_2$), 4.10–4.40 (m, 3H, α-H), 5.05 (m, 4H, Cbz), 6.05 (m, 1H, NH), 7.20–7.40 (m, 10H, Ph), 7.85 (m, 2H, NH), 9.05 (m, 1H, NH).

Example 3II

Cbz-Asp(O-tBu)-Glu(O-tBu)-Val-AAsp(O-tBu)-(2S,3S)-EP-CONHCH$_2$Ph was obtained using the mixed anhydride coupling method and was purified using column chromatography on silica gel using 1:2 EtOAc:hexane as the eluent; white solid, yield 31%. MS (ESI) m/z 939.6 [(M+1)$^+$]. $^1$H NMR (CDCl$_3$): 0.97 (m, 6H, Val), 1.40 (m, 27H, tBu), 1.9–2.3 (m, 3H, Val and Glu), 2.41 (m, 2H, Glu), 2.80–2.95 (m, 2H, Asp), 3.63 and 3.97 (d, 2H, epoxy), 4.05–4.22 (m, 4H, NCH$_2$), 4.20–4.55 (m, 3H, α-H), 4.45 (m, 2H, NHCH$_2$Ph), 5.05 (m, 2H, Cbz), 7.20–7.40 (m, 10H, Ph), 6.15 (m, 1H, NH), 6.60 (1H, NH), 7.85 (m, 2H, NH).

Example 3JJ

Cbz-Glu(O-tBu)-Val-AAsp(O-tBu)-(2S,3S)-EP-COOEt was obtained using the mixed anhydride coupling method and was purified using column chromatography on silica gel with 1:2 EtOAc:hexane as the eluent, and recrystallized from EtOAc/hexane; white solid, yield 44%. MS (ESI) m/z 706.1 [(M+1)$^+$]. $^1$H NMR (DMSO-d$_6$): 0.90 (m, 6H, Val), 1.20 (t, 3H, OCH$_2$CH$_3$), 1.40 (m, 18H, tBu), 1.60–2.00 (m, 3H, Val and Glu), 2.21 (m, 2H, Glu), 3.50 and 3.98 (d, 2H, epoxy), 4.00–4.20 (m, 4H, NCH$_2$ and OCH$_2$CH$_3$), 4.20–4.40 (m, 2H, α-H), 5.05 (m, 2H, Cbz), 7.20–7.40 (m, 5H, Ph), 8.00 (m, 2H, NH).

Example 3KK

Cbz-Glu(O-tBu)-Val-AAsp(O-tBu)-(2R,3R)-EP-COOEt was obtained using the mixed anhydride coupling method and was purified using column chromatography on silica gel with 7:13:1:19 hexane:EtOAc:MeOH:CH$_2$Cl$_2$ as the eluent, and then rechromatographed using 3:1 EtOAc:hexane as the eluent; white solid, yield 35%. MS (ESI) m/z 706.1 [(M+ 1)$^+$]. $^1$H NMR (CDCl$_3$): 0.94 (m, 6H, Val), 1.21 (t, 3H, OCH$_2$CH$_3$), 1.43 (m, 18H, tBu), 1.60–2.00 (m, 3H, Val and Glu), 2.21 (m, 2H, Glu), 3.60 and 3.98 (d, 2H, epoxy), 4.00–4.20 (m, 4H, NCH$_2$ and OCH$_2$CH$_3$), 4.20–4.40 (m, 2H, α-H), 5.10 (m, 2H, Cbz), 7.20–7.40 (m, 5H, Ph), 8.00 (m, 2H, NH).

Example 3LL

Cbz-Glu(O-tBu)-Val-AAsp(O-tBu)-(2R,3R)-EP-CO-Phe-NH$_2$ was obtained using the mixed anhydride coupling method and was purified by column chromatography on silica gel using 10:1:9 EtOAc:MeOH:CH$_2$Cl$_2$ as the eluent, and then rechromatographed using 10:7:3:1 CH$_2$Cl$_2$:EtOAc:THF:MeOH as the eluent; white solid, yield 32%. MS (ESI) m/z 825.4 [(M+1)$^+$]. $^1$H NMR (CDCl$_3$): 0.94 (m, 6H, Val), 1.43 (m, 18H, tBu), 1.60–2.00 (m, 3H, Val and Glu), 2.21 (m, 2H, Glu), 2.80 and 2.95 (m, 2H, Phe), 3.50 and 3.98 (d, 2H, epoxy), 3.90–4.20 (m, 2H, NCH$_2$), 4.00–4.40 (m, 3H, α-H), 5.10 (m, 2H, Cbz), 7.0 (s, 2H, NH$_2$), 7.20–7.40 (m, 10H, Ph), 8.00 (m, 2H, NH).

Example 3MM

Cbz-Leu-Glu(O-tBu)-Thr-AAsp(O-tBu)-(2S,3S)-EP-COOCH$_2$Ph was synthesized using the mixed anhydride coupling method, purified by column chromatography using 4:1 (10% MeOH:CH$_2$Cl$_2$):EtOAc as an eluent, and then rechromatographed using 4:1 (5% MeOH:CH$_2$Cl$_2$):EtOAc as the eluent; white solid, yield 44%. MS (ESI) m/z 884.4 [(M+1)$^+$].

Example 3NN

Cbz-Leu-Glu(O-tBu)-Thr-AAsp(O-tBu)-(2S,3S)-EP-CONHCH$_2$CH$_2$Ph was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 52%. $^1$H NMR (CDCl$_3$): 0.90 (t, 6H, Leu CH$_3$), 1.14 (m, 3H, Thr CH$_3$), 1.26 (m, 2H, Leu CH$_2$), 1.45 (s, 18H, tBu), 1.65 (m, 1H, Leu CH), 2.02 (m, 2H, Glu CH$_2$), 2.40 (m, 2H, Glu CH$_2$), 2.77 (t, 2H, CH$_2$Ph), 3.40–3.70 (m, 6H, epoxy, AAsp CH$_2$ and NCH$_2$), 4.20 (m, 3H, α-H), 4.40 (m, 1H, Thr CH), 5.07 (s, 2H, Z), 6.40 (b, 1H, NH), 7.15–7.35 (m, 12H, Ph and NH), 8.00 (s, 1H, NH), 9.45 (s, 1H, NH).

Example 3OO

Cbz-Leu-Glu(O-tBu)-Thr-AAsp(O-tBu)-(2S,3S)-EP-CO-Ala-NHBzl was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 42%. $^1$H NMR (Acetone-d$_6$): 0.90 (t, 6H, Leu CH$_3$), 1.15 (d, 3H, Thr CH$_3$), 1.25 (m, 2H, Leu CH$_2$), 1.30 (d, 3H, Ala CH$_3$), 1.45 (t, 18H, tBu), 1.60 (m, 1H, Leu CH), 1.95 and 2.10 (d of m, 2H, Glu CH$_2$), 2.40 (m, 2H, Glu CH$_2$), 2.90 (s, 2H, AAsp CH$_2$), 3.56 and 3.64 (d, 2H, epoxy), 4.25 (m, 3H, α-H), 4.35 (m, 1H, α-H), 4.40–4.50 (m, 3H, Thr CH and CH$_2$Ph), 5.05 (q, 2H, Z), 6.80 (d, 1H, NH), 7.10–7.35 (m, 10H, Ph), 7.40 (d, 1H, NH), 7.75 (b, 1H, NH), 7.90 (d, 2H, NH), 9.80 (s, 1H, NH).

Example 3PP

Cbz-Ile-Glu(O-tBu)-Thr-AAsp(O-tBu)-(2S,3S)-EP-COOEt was synthesized using the mixed anhydride coupling method, purified by column chromatography using 1:13 MeOH:CH$_2$Cl$_2$ as an eluent, and then rechromatographed using 2:1 EtOAc:hexane as the eluent. The crude product was then rechromatographed using 1:13 MeOH:CH$_2$Cl$_2$ as an eluent and placed on a preparatory TLC plate using 1:13 MeOH:CH$_2$Cl$_2$ as the eluent; white solid, yield 37%. HRMS (FAB) Calcd. for C$_{39}$H$_{60}$N$_5$O$_{14}$: 822.41368. Observed m/z 822.41366. $^1$H NMR (CDCl$_3$): 0.8–1.0 (m, 6H, Ile CH$_3$), 1.1–1.4 (m, 8H, Thr CH$_3$, Ile CH$_2$, and OCH$_2$CH$_3$), 1.4–1.5 (s, 18H, tBu), 1.9–2.2 (m, 3H, CH Ile and Glu CH$_2$), 2.3–2.45 and 2.5–2.6 (m, 2H, Glu CH$_2$), 3.0–3.2 (m, 2H, NCH$_2$COOH), 3.6 (d, 1H, epoxy), 4.0–4.3 (m, 5H, epoxy, α-H, OCH$_2$CH$_3$, and CH—OH), 4.3–4.5 (m, 2H, α-H), 5.1 (m, 2H, Cbz), 5.35 (m, 1H, NH), 7.20–7.40 (m, 5H, Ph), 8.25 (m, 1H, NH), 9.5 (m, 1H, NH).

Example 3QQ

Cbz-Ile-Glu(O-tBu)-Thr-AAsp(O-tBu)-(2S,3S)-EP-COOCH$_2$Ph was synthesized using the mixed anhydride coupling method and purified by column chromatography using 4:1 (5% MeOH:CH$_2$Cl$_2$):EtOAc as the eluent; white solid, yield 38%. MS (FAB) m/z 884 [(M+1)$^+$].

Example 3RR

Cbz-Ile-Glu(O-tBu)-Thr-AAsp(O-tBu)-(2R,3R)-EP-COOCH$_2$Ph was synthesized using the mixed anhydride coupling method and purified by column chromatography using 4:1 (10% MeOH:CH$_2$Cl$_2$):EtOAc as the eluent, and then rechromatographed using 4:1 (5% MeOH:CH$_2$Cl$_2$):EtOAc as the eluent; white solid, yield 37%. MS (FAB) m/z 884.4 [(M+1)$^+$].

Example 3SS

Cbz-Ile-Glu(O-tBu)-Thr-AAsp(O-tBu)-(2R,3R)-EP-CONHCH$_2$Ph was synthesized using the mixed anhydride coupling method, purified by column chromatography using 4:1 (10% MeOH:CH$_2$Cl$_2$):EtOAc as the eluent, and then rechromatographed using 4:1 (5% MeOH:CH$_2$Cl$_2$):EtOAc as the eluent; white solid, yield 47%. MS (ESI) m/z 883.6 [(M+1)$^+$]. $^1$H NMR (DMSO-d$_6$): 0.7–0.9 (m, 6H, Ile CH$_3$), 0.9–1.2 (m, 4H, Thr CH$_3$ and Ile CH$_2$), 1.2–1.5 (m, 19H, tBu and Ile CH$_2$), 1.6–1.8 (m, 2H, CH Ile and Glu CH$_2$), 1.8–1.9 (m, 1H, Glu CH$_2$), 2.1–2.3 (m, 2H, Glu CH$_2$), 3.5 (d, 1H, epoxy), 3.8–4.0 (m, 3H, NCH$_2$COOH and CH—OH), 4.03 (d, 1H, epoxy), 4.1–4.2 (m, 1H, α-H), 4.2–4.5 (m, 4H, NHCH$_2$Ph and α-H), 4.9–5.1 (m, 2H, Cbz), 7.15–7.40 (m, 10H, Ph), 7.85 (m, 1H, NH), 8.05 (m, 1H, NH).

Example 3TT

Cbz-Ile-Glu(O-tBu)-Thr-AAsp(O-tBu)-(2R,3R)-EP-COOEt was synthesized using the mixed anhydride coupling method, purified by column chromatography using 1:13 MeOH:CH$_2$Cl$_2$ as an eluent, and then rechromatographed using 2:1 EtOAc:hexane as an eluent; white solid, yield 43%. HRMS (FAB) Calcd. for C$_{39}$H$_{60}$N$_5$O$_{14}$: 822.41368. Observed m/z 822.41287. $^1$H NMR (CDCl$_3$): 0.8–1.0 (m, 6H, Ile CH$_3$), 1.1–1.35 (m, 8H, Thr CH$_3$, Ile CH$_2$, and OCH$_2$CH$_3$), 1.4–1.5 (d, 18H, tBu), 1.9–2.15 (m, 3H, CH Ile and Glu CH$_2$), 2.3–2.45 and 2.5–2.6 (m, 2H, Glu CH$_2$), 3.0–3.2 (m, 2H, NCH$_2$COOH), 3.6 (d, 1H, epoxy), 4.0–4.5 (m, 7H, epoxy, OCH$_2$CH$_3$, CH—OH, and α-H), 5.1 (m, 2H, Cbz), 5.4 (m, 1H, NH), 7.20–7.40 (m, 5H, Ph), 8.25 (m, 1H, NH), 9.4 (m, 1H, NH).

Example 3UU

Cbz-Ile-Glu(O-tBu)-Thr-AAsp(O-tBu)-(2S,3S)-EP-CO-Ala-NHBzl was obtained using the EDC/HOBt coupling method, purified by column chromatography on silica gel with 19:1 CH$_2$Cl$_2$:MeOH as the eluent, and then rechromatographed using 50:35:10:5 CH$_2$Cl$_2$:EtOAc:THF:MeOH as the eluent; white solid, yield 36%. $^1$H NMR (Acetone-d$_6$): 0.90 (t, 3H, Ile CH$_3$), 0.98 (d, 3H, Ile CH$_3$), 1.14 (d, 3H, Thr CH$_3$), 1.22 (m, 2H, Ile CH$_2$), 1.37 (d, 3H, Ala CH$_3$), 1.42 (m, 19H, Ile CH and tBu), 1.90 and 2.10 (d of m, 2H, Glu CH$_2$), 2.40 (m, 2H, Glu CH$_2$), 2.93 (s, 2H, AAsp CH$_2$), 3.72 (d, 2H, epoxy), 4.20 (m, 3H, α-H), 4.30 (m, 1H, α-H), 4.40–4.50 (m, 3H, Thr CH and CH$_2$Ph), 5.07 (q, 2H, Z), 6.70 (d, 1H, NH), 7.10–7.35 (m, 10H, Ph), 7.50 (d, 1H, NH), 7.80 (b, 1H, NH), 7.90 (b, 2H, NH), 9.80 (s, 1H, NH).

Example 4 trans-3-(N$^2$-(N-3-Phenylpropanoylvalylalanyl)-N$^1$-t-butoxycarbonylmethylhydrazinocarbonyl)-2-(2-phenylethyl)oxirane (PhPr-Val-Ala-AAsp(O-tBu)-trans-EP-CH$_2$CH$_2$Ph). This compound was obtained using EDC/HOBt coupling of PhPr-Val-Ala-NH—NH—CH$_2$COO-tBu with trans-3-phenethyloxirane-2-carboxylic acid (5, Y═CH$_2$CH$_2$Ph), followed by purification by chromatography on a silica gel column with 1:19 MeOH:CH$_2$Cl$_2$; white solid, yield=38%. MS and $^1$H NMR (CDCl$_3$) were consistent with the proposed structure.

Example 5

(2S,3S)-3-(N$^2$-(N-Benzyloxycarbonylalanylalanyl)-N$^1$-carbamoylmethylhydrazinocarbonyl)oxirane-2-carboxylic Acid Ethyl Ester (Cbz-Ala-Ala-AAsn-(2S,3S)-EP-COOEt). This compound was obtained using the EDC/HOBt coupling method, purified by chromatography on silica gel column using 1:7 MeOH:CH$_2$Cl$_2$ as the eluting solvent system and recrystallized from EtOAc/hexane; white solid, yield 17%. $^1$H NMR (DMSO-d$_6$): 1.2 (m, 9H, CH$_3$), 3.2 (m, 2H, NCH$_2$CO), 3.5 (s, 1H, epoxy), 4–4.05 (m, 2H, α-H and epoxy), 4.05–4.25 (m, 3H, OCH$_2$CH$_3$ and α-H), 5.20 (m, 2H, Cbz), 7.2 (s, 1H, NH), 7.22–7.4 (m, 5H, Ph), 7.5 (s, 1H, NH), 8.17 (d, 1H, NH). HRMS (FAB) Calcd. for C$_{22}$H$_{30}$N$_5$O$_9$:508.20435. Observed m/z 508.20540. Anal. Calcd. for C$_{22}$H$_{29}$N$_5$O$_9$.0.5H$_2$O: C, 51.16; H, 5.81; N, 13.56. Found: C, 51.31; H, 5.82;N, 13.24.

Example 6

(2R,3R)-3-(N$^2$-(N-Benzyloxycarbonylalanylalanyl)-N$^1$-carbamoylmethylhydrazinocarbonyl)oxirane-2-carboxylic Acid Ethyl Ester (Cbz-Ala-Ala-AAsn-(2R,3R)-EP-COOEt). This compound was obtained using the EDC/HOBt coupling method, purified by chromatography on silica gel column using 1:7 MeOH:CH$_2$Cl$_2$ as the eluting solvent system and recrystallized from EtOAc/hexane; white solid, yield 19%. $^1$H NMR (DMSO-d$_6$): 1.2 (m, 9H, CH$_3$), 3.2 (m, 2H, NCH$_2$CO), 3.5 (s, 1H, epoxy), 3.9 (s, 1H, epoxy), 4–4.3 (m, 4H, α-Hs and OCH$_2$CH$_3$), 5.20 (m, 2H, Cbz), 7.2 (s, 1H, NH), 7.25–7.4 (m, 5H, Ph), 7.5 (s, 1H, NH), 8.18 (d, 1H, NH). ☐RMS (FAB) Calcd. for C$_{22}$H$_{30}$N$_5$O$_9$: 508.20435. Observed m/z 508.20845. Anal. Calcd. for C$_{22}$H$_{29}$N$_5$O$_9$.0.57H$_2$O: C, 51.038; H, 5.827; N, 13.53. Found: C, 51.28; H, 6.00; N, 13.05.

Example 7 trans-3-(N$^2$-(N-Benzyloxycarbonylalanylalanyl)-N$^1$-carbamoylmethylhydrazinocarbonyl)oxirane-2-carboxylic Acid Ethyl Ester (Cbz-Ala-Ala-AAsn-trans-EP-COOEt). This compound was obtained using the EDC/HOBt coupling method, purified by chromatography on silica gel column using 1:9 MeOH:CH$_2$Cl$_2$ as the eluting solvent system and recrystallized from EtOAc/hexane; white solid, yield 8%. $^1$H NMR (CDCl$_3$): 1.2 (m, 9H, CH$_3$), 3.4 (m, 2H, NCH$_2$CO), 3.6 (s, 1H, epoxy), 3.9 (s, 1H, epoxy), 4.1–4.3 (m, 3H, α-H and OCH$_2$CH$_3$), 4.4 (m, 1H, α-H), 5.15 (m, 2H, Cbz), 5.5 (m, 1H, NH), 6.6 (m, 1H, NH), 7.2 (s, 1H, NH), 7.3 (m, 5H, Ph). HRMS (FAB) Calcd. for C$_{22}$H$_{30}$N$_5$O$_9$: 508.20435. Observed m/z 508.20362. Anal. Calcd. for C$_{22}$H$_{29}$N$_5$O$_9$.0.7H$_2$O: C, 50.81; H, 5.85; N, 13.47. Found: C, 51.05; H, 5.89; N, 13.19.

Example 8 cis-3-(N$^2$-(N-Benzyloxycarbonylalanylalanyl)-N$^1$-carbamoylmethylhydrazinocarbonyl)oxirane-2-carboxylic Acid Ethyl Ester (Cbz-Ala-Ala-AAsn-cis-EP-COOEt). This compound was obtained using the EDC/HOBt coupling method, purified by chromatography on silica gel column using 1:7 MeOH:CH$_2$Cl$_2$ as the eluting solvent system and recrystallized from EtOAc/hexane; white solid, yield 4%. $^1$H NMR (DMSO-d$_6$): 1.1–1.3 (m, 9H, CH$_3$), 3.4 (m, 2H, NCH$_2$CO), 3.7–3.8 and 3.85 (m, 2H, epoxy), 4.0–4.18 (m, 3H, α-H and OCH$_2$CH$_3$), 4.19–4.3 (m, 1H, α-H), 5.03 (m, 2H, Cbz), 7.2 (m, 1H, NH), 7.3–7.5 (m, 6H, Ph and NH), 8.18 (m, 1H, NH). HRMS (FAB) Calcd. for C$_{22}$H$_{30}$N$_5$O$_9$: 508.20435. Observed m/z 508.20490. Anal. Calcd. for C$_{22}$H$_{29}$N$_5$O$_9$.0.6H$_2$O: C, 50.98; H, 5.83; N, 13.51. Found: C, 50.74; H, 5.80; N, 13.20.

Example 9

(2S,3S)-3-(N$^2$-(N-Benzyloxycarbonylleucylleucyl)-N$^1$-isobutylhydrazinocarbonyl)oxirane-2-carboxylic Acid Ethyl Ester (Cbz-Leu-Leu-ALeu-(2S,3S)-EP-COOEt). This compound was obtained using the EDC/HOBt coupling method, purified by chromatography on silica gel column using 5:78:17 MeOH:CH$_2$Cl$_2$:EtOAc as the eluting solvent system and recrystallized from EtOAc/hexane; white solid, yield 49%. $^1$H NMR (CDCl$_3$): 0.90 (m, 18H, Leu), 1.21 (t, 3H, OCH$_2$CH$_3$), 1.40–1.90 (m, 7H, Leu), 3.20–3.45 (m, 2H, ALeu), 3.60 and 3.82 (d, 2H, epoxy), 4.15 (m, 1H, α-H), 4.20 (q, 2H, OCH$_2$CH$_3$), 4.45 (m, 1H, α-H) 5.20 (m, 2H, Cbz), 5.30 (m, 1H, NH), 6.41 (m, 1H, NH), 7.16–7.37 (m, 5H, Ph), 9.00 (m, 1H, NH). HRMS (FAB) Calcd. for C$_{30}$H$_{47}$N$_4$O$_8$: 591.3394. Observed m/z 591.3425. Anal. Calcd. for C$_{30}$H$_{46}$N$_4$O$_8$.0.6H$_2$O: C, 59.90; H, 7.90; N, 9.31. Found: C, 59.90; H, 7.77; N, 9.32.

Example 10

(2R,3R)-3-(N$^2$-(N-Benzyloxycarbonylleucylleucyl)-N$^1$-isobutylhydrazinocarbonyl)oxirane-2-carboxylic Acid Ethyl Ester (Cbz-Leu-Leu-ALeu-(2R,3R)-EP-COOEt). This compound was obtained using the EDC/HOBt coupling method, purified by chromatography on silica gel column using 1:9 MeOH:CH$_2$Cl$_2$ as the eluting solvent system and recrystallized from ether/hexane; white solid, yield 39%. $^1$H NMR (CDCl$_3$): 0.90 (m, 18H, Leu), 1.21 (t, 3H, OCH$_2$CH$_3$), 1.40–1.90 (m, 7H, Leu), 3.20–3.45 (m, 2H, ALeu), 3.60 and 3.82 (d, 2H, epoxy), 4.15 (m, 1H, α-H), 4.20 (q, 2H, OCH$_2$CH$_3$), 4.45 (m, 1H, α-H) 5.20 (m, 2H, Cbz), 5.30 (m, 1H, NH), 6.41 (m, 1H, NH), 7.16–7.37 (m, 5H, Ph), 9.00 (m, 1H, NH). HRMS (FAB) Calcd. for C$_{30}$H$_{47}$N$_4$O$_8$: 591.3394. Observed m/z 591.3435. Anal. Calcd. for C$_{30}$H$_{46}$N$_4$O$_8$.0.55H$_2$O: C, 59.99; H, 7.90; N, 9.33. Found: C, 60.02; H, 7.78; N, 9.33.

Example 11 trans-3-(N$^2$-(N-Benzyloxycarbonylleucylleucyl)-N$^1$-isobutylhydrazinocarbonyl)oxirane-2-carboxylic Acid Ethyl Ester (Cbz-Leu-Leu-ALeu-trans-EP-COOEt). This compound was obtained using the EDC/HOBt coupling method, purified by chromatography on silica gel column using 1:9 MeOH:CH$_2$Cl$_2$ as the eluting solvent system and recrystallized from ether/hexane; white solid, yield 42%. $^1$H NMR (CDCl$_3$): 0.90 (m, 18H, Leu), 1.21 (t, 3H, OCH$_2$CH$_3$), 1.40–1.90 (m, 7H, Leu), 3.20–3.45 (m, 2H, ALeu), 3.60 and 3.82 (d, 2H, epoxy), 4.15 (m, 1H, α-H), 4.20 (q, 2H, OCH$_2$CH$_3$), 4.45 (m, 1H, α-H) 5.20 (m, 2H, Cbz), 5.30 (m, 1H, NH), 6.41 (m, 1H, NH), 7.16–7.37 (m, 5H, Ph), 9.00 (m, 1H, NH). HRMS (FAB) Calcd. for: C$_{30}$H$_{47}$N$_4$O$_8$ 591.3394. Observed m/z 591.3419. Anal. Calcd. for C$_{30}$H$_{46}$N$_4$O$_8$.0.5H$_2$O: C, 60.08; H, 7.90; N, 9.34. Found: C, 60.09; H, 7.86; N, 9.28.

Example 12

Deblocking of the t-Butyl Group in Aza-Asp Peptides. Epoxysuccinyl peptides (PhPr-Val-Ala-AAsp(O-tBu)-trans-EP-COOCH$_2$Ph), (PhPr-Val-Ala-AAsp(O-tBu)-trans-EP- CH₂CH₂Ph), (Cbz-Asp-Glu-Val-AAsp(O-tBu)-(2S,3S)-EP-COOEt), (Cbz-Asp-Glu-Val-AAsp(O-tBu)-(2R,3R)-EP-COOEt), (Cbz-Leu-Glu-Thr-AAsp(O-tBu)-(2S,3S)-EP-COOEt), and peptidyl-AAsp(O-tBu)-EP-R₃ derivatives all were separately reacted with TFA at 0° C. for 1 h⁻¹·⁵ hr. The excess TFA was removed under vacuum, and the final products were recrystallized from methanol/ether and ether/hexane to give the final epoxysuccinyl peptides as white solids (yields 59–85%). The products of these reactions are listed in Examples 12A–12F.

Example 12A trans-3-(N²-(N-3-Phenylpropanoylvalylalanyl)-N¹-carboxylmethylhydrazinocarbonyl)oxirane-2-carboxylic Acid Benzyl Ester (PhPr-Val-Ala-AAsp-trans-EP-COOCH₂Ph). ¹H NMR (CDCl₃): 0.80 (m, 6H, Val), 1.21 (m, 3H, Ala), 1.90 (m, 1H, Val), 2.54 (m, 3H, PhCH₂ and Asp), 2.90 (m, 3H, PhCH₂CH₂CO and Asp), 3.64 and 3.71 (d, 2H, epoxy), 4.15 (m, 2H, NCH₂COOH), 4.50 (m, 2H, α-H), 5.20 (m, 2H, Benzyl), 6.51 (m, 1H, NH), 6.95 (M, 1H, NH), 7.16–7.37 (m, 10H, Ph), 9.60 (M, 1H, NH). HRMS (FAB) Calcd. for C₃₀H₃₆N₄O₉: 597.2561. Observed m/z 597.2647. Anal. Calcd. for C₃₀H₃₆N₄O₉.0.5H₂O: C, 59.48; H, 6.33; N, 9.25. Found: C, 59.47; H, 6.13; N, 9.31.

Example 12B trans-3-(N²-(N-3-Phenylpropanoylvalylalanyl)-N¹-carboxylmethylhydrazinocarbonyl)-2-(2-phenylethyl)oxirane (PhPr-Val-Ala-AAsp-trans-EP-CH₂CH₂Ph). ¹H NMR (CDCl₃): 0.78 (m, 6H, Val), 1.20 (t, 3H, Ala), 1.90 (m, 2H, PhCH₂), 2.52 (m, 2H, PhCH₂CH₂CO), 2.67 (m, 2H, PhCH₂CH₂-EP), 2.88 (m, 2H, PhCH₂CH₂CO), 4.18 (M, 2H, NCH₂COOH), 4.52 (M, 2H, α-H), 6.55 (m, 1H, NH), 6.95 (m, 1H, NH), 7.16–7, 26 (M, 10H, Ph), 9.60 (m, 1H, NH). HRMS (FAB) Calcd. for C₃₀H₃₈N₄O₇: 597.2819. Observed m/z 567.2868. Anal. Calcd. for C₃₀H₃₆N₄O₉H₂O: C, 61.62; H, 6.88; N, 9.58. Found: C, 61.52; H, 6.58; N, 9.56.

Example 12C (2S,3S)-3-(N²-(N-Benzyloxycarbonylaspartyl-glutamylvalyl)-N¹-carboxymethylhydrazinocarbonyl)oxirane-2-carboxylic Acid Ethyl Ester (Cbz-Asp-Glu-Val-AAsp-(2S,3S)-EP-COOEt). ¹H NMR (DMSO-d₆): 0.84 (m, 6H, Val), 1.20, 1.21 (t, 3H, OCH₂CH₃), 1.7–2.1 (m, 3H, Val, Glu), 2.21 (m, 2H, Glu), 2.40–2.65 (m, 2H Asp), 3.58 and 4.10 (d, 2H, epoxy), 4.05–4.22 (m, 4H, NCH₂COOH and OCH₂CH₃), 4.50–4.60 (m, 3H, α-H), 5.05 (m, 2H, Cbz), 7.20–7.40 (m, 5H, Ph), 7.60 (1H, NH), 7.85 (m, 2H, NH), 11.00 (m, COOH). HRMS (FAB) Calcd. for C₃₀H₃₉N₅O₁₅: 710.25209. Observed m/z 710.2550. Anal. Calcd. for C₃₀H₃₉N₅O₁₅.1.65H₂O: C, 48.73; H, 5.76; N, 9.47. Found: C, 48.73; H, 5.63; N, 9.45.

Example 12D (2R,3R)-3-(N²-(N-Benzyloxycarbonylaspartyl-glutamylvalyl)-N¹-carboxymethylhydrazinocarbonyl)oxirane-2-carboxylic Acid Ethyl Ester (Cbz-Asp-Glu-Val-AAsp-(2R,3R)-EP-COOEt). ¹H NMR (DMSO-d₆): 0.84 (m, 6H, Val), 1.20, 1.21 (t, 3H, OCH₂CH₃), 1.7–2.1 (m, 3H, Val, Glu), 2.21 (m, 2H, Glu), 2.40–2.65 (m, 2H Asp), 3.58 and 4.10 (d, 2H, epoxy), 4.05–4.22 (m, 4H, NCH₂COOH and OCH₂CH₃), 4.50–4.60 (m, 3H, α-H), 5.05 (m, 2H, Cbz), 7.20–7.40 (m, 5H, Ph), 7.60 (1H, NH), 7.85 (m, 2H, NH), 11.00 (m, COOH). HRMS (FAB) Calcd. for C₃₀H₃₉N₅O₁₅: 710.25209. Observed m/z 710.25195. Anal. Calcd. for C₃₀H₃₉N₅O₁₅.0.9H₂O: C, 49.64; H, 5.66; N, 9.65. Found: C, 49.59; H, 5.56; N, 9.66.

Example 12E (2R,3R)-3-(N²-(N-Benzyloxycarbonylleucyl-glutamylthreonyl)-N¹-carboxymethylhydrazinocarbonyl)oxirane-2-carboxylic Acid Ethyl Ester (Cbz-Leu-Glu-Thr-AAsp-(2R,3R)-EP-COOEt). ¹H NMR (DMSO-d₆): 0.82 (t, 6H, Leu CH₃), 1.0 (d, 3H, Thr CH₃), 1.2 (t, 3H, OCH₂CH₃), 1.4 (m, 2H, Leu CH₂), 1.6 (m, 1H, CH Leu), 1.78 (m, 1H, Glu CH₂), 1.9 (m, 1H, Glu CH₂), 2.25 (m, 2H, Glu), 3.5 (s, 1H, epoxy), 3.9–4.0 (m, 1H, α-H), 4.0–4.1 (m, 3H, NCH₂COOH, epoxy), 4.1–4.2 (m, 3H, OCH₂CH₃ and CH—OH), 4.32–4.41 (m, 2H, α-H), 5.05 (m, 2H, Cbz), 7.30–7.40 (m, 5H, Ph), 7.45 (d, 1H, NH), 7.80 (m, 1H, NH), 8.05 (m, 1H, NH), 11.00 (m, COOH).

HRMS (FAB) Calcd. for C₃₁H₄₄N₅O₁₄: 710.28848. Observed m/z 710.29480. Anal. Calcd. for C₃₁H₄₃N₅O₁₄.H₂O: C, 51.17; H, 6.19; N, 9.63. Found: C, 51.33; H, 6.02; N, 9.66.

Example 12F (2S,3S)-3-(N²-(N-Benzyloxycarbonylleucyl-glutamylthreonyl)-N¹-carboxymethylhydrazinocarbonyl)oxirane-2-carboxylic Acid Ethyl Ester (Cbz-Leu-Glu-Thr-AAsp-(2S,3S)-EP-COOEt). ¹H NMR (DMSO-d₆): 0.85 (t, 6H, Leu CH₃), 1.05 (d, 3H, Thr CH₃), 1.2 (t, 3H, OCH₂CH₃), 1.4 (m, 2H, Leu CH₂), 1.6 (m, 1H, CH Leu), 1.77 (m, 1H, Glu CH₂), 1.9 (m, 1H, Glu CH₂), 2.3 (m, 2H, Glu CH₂), 3.5 (s, 1H, epoxy), 3.9–4.1 (m, 4H, NCH₂COOH, epoxy, α-H), 4.1–4.3 (m, 3H, OCH₂CH₃ and CH—OH), 4.3–4.4 (m, 2H, α-H), 4.95 (m, 1H, NH), 5.02 (m, 2H, Cbz), 7.30–7.40 (m, 5H, Ph), 7.50 (d, 1H, NH), 7.78 (m, 1H, NH), 8.05 (m, 1H, NH), 11.00 (m, COOH). HRMS (FAB) Calcd. for C₃₁H₄₄N₅O₁₄: 710.28848. Observed m/z 710.28450. Anal. Calcd. for C₃₁H₄₃N₅O₁₄.1.25H₂O: C, 50.85; H, 6.22; N, 9.57. Found: C, 50.74; H, 6.27; N, 9.67.

Example 12G (2S,3S)-2-(Dibutylcarbamoyl)-3-(N²-(3-phenylpropanoylvalylalanyl)-N¹-carboxymethylhydrazinocarbonyl)oxirane (PhPr-Val-Ala-AAsp-(2S,3S)-EP-CON(nBu)₂). ¹H NMR (DMSO-d₆): 0.74 and 0.79 (m, 12H, Val and n-butyl CH₃), 1.20 (m, 7H, Ala CH₃ and CH₂), 1.45 (m, 4H, CH₂), 1.88 (m, 1H, Val CH), 2.44 (m, 2H, PhCH₂), 2.79 (m, 2H, PhCH₂CH₂), 3.20 (m, 4H, CH₂N), 3.32 (s, 2H, AAsp CH₂COOH), 3.75 (d, 2H, epoxy), 4.17 (m, 2H, α-H), 7.13–7.24 (m, 6H, Ph and NH), 7.82 (d, 1H, NH), 8.20 (b, 1H, NH), 10.90 (b, 1H, COOH). HRMS (FAB) Calcd. for C₃₁H₄₈N₅O₈: 618.3503. Observed m/z 618.3534. Anal. Calcd. for C₃₁H₄₇N₅O₈.H₂O: C, 58.57; H, 7.77; N, 11.02. Found: C, 58.62; H, 7.59; N, 11.26.

Example 12H (2S,3S)-2-(N-Methyl-N-benzylcarbamoyl)-3-(N²-(3-phenylpropanoylvalylalanyl)-N¹-carboxymethylhydrazinocarbonyl)oxirane (PhPr-Val-Ala-AAsp-(2S,3S)-EP-CON(CH₃)Bzl). ¹H NMR (DMSO-d₆): 0.76 (m, 6H, Val CH₃), 1.16 (m, 3H, Ala CH₃), 1.89 (m, 1H, Val CH), 2.42 (m, 2H, PhCH₂), 2.77 (m, 3.5H, PhCH₂CH₂CO and CH₃N), 3.00 (m, 1.5H, CH₃N), 3.40 (d, 2H, AAsp CH₂COOH), 3.96 (s, 2H, epoxy), 4.15 (m, 2H, α-H), 4.45 (m, 2H, PhCH$_2$N), 7.12–7.37 (m, 11H, Ph and NH), 7.83 (m, 1H, NH), 8.22 (d, 1H, NH), 10.80 (s, 1H, COOH). HRMS (FAB) Calcd. for C$_{31}$H$_{40}$N$_5$O$_8$: 610.2877. Observed m/z 610.2870. Anal. Calcd. for C$_{31}$H$_{39}$N$_5$O$_8$.H$_2$O: C, 59.32; H, 6.58; N, 11.16. Found: C, 59.49; H, 6.32; N, 11.36.

Example 12H (2S,3S)-2-(Dibenzylcarbamoyl)-3-(N$^2$-(3-phenylpropanoylvalylalanyl)-N$^1$-carboxymethylhydrazinocarbonyl)oxirane (PhPr-Val-Ala-AAsp-(2S,3S)-EP- CON(CH$_2$Ph)$_2$). $^1$H NMR (DMSO-d$_6$): 0.75 (m, 6H, Val CH$_3$), 1.08 (m, 3H, Ala CH$_3$), 1.90 (m, 1H, Val CH), 2.42 (m, 2H, PhCH$_2$), 2.77 (t, 2H, PhCH$_2$CH$_2$CO), 3.40 (d, 2H, AAsp CH$_2$COOH), 3.80 (s, 2H, epoxy), 4.15 (m, 2H, α-H), 4.55 (d, 4H, PhCH$_2$N), 7.13–7.40 (m, 11H, Ph and NH), 7.85 (m, 1H, NH), 8.15 (m, 1H, NH), 10.80 (s, 1H, COOH). HRMS (FAB) Calcd. for C$_{37}$H$_{44}$N$_5$O$_8$: 686.3190. Observed m/z 686.3238. Anal. Calcd. for C$_{37}$H$_{43}$N$_5$O$_8$.0.5H$_2$O: C, 63.98; H, 6.34; N, 10.08. Found: C, 64.18; H, 6.13; N, 9.91.

Example 12I (2S,3S)-2-(N-Methyl-N-benzylcarbamoyl)-3-(N$^2$-(N-benzyloxycarbonylleucylglutamylthreonyl)-N$^1$-carboxymethylhydrazinocarbonyl)oxirane (Cbz-Leu-Glu-Thr-AAsp-(2S,3S)-EP-CON(CH$_3$)Bzl). $^1$H NMR (DMSO-d$_6$): 0.83 (t, 6H, Leu CH$_3$), 1.04 (m, 3H, Thr CH$_3$), 1.41 (m, 2H, Leu CH$_2$), 1.60 (m, 1H, Leu CH), 1.75 and 1.90 (d of m, 2H, Glu CH$_2$), 2.24 (m, 2H, Glu CH$_2$), 2.82 and 2.95 (d, 3H, NCH$_3$), 3.32 (s, 2H, AAsp CH$_2$), 3.80–4.10 (m, 5H, epoxy and α-H), 4.25 (d, 1H, Thr CH), 4.37 (m, 2H, CH$_2$Ph), 4.99 (s, 2H, Z), 7.15–7.44 (m, 11H, Ph and NH), 7.75 (b, 1H, NH), 8.06 (b, 2H, NH), 10.80 (b, 2H. COOH). Anal. Calcd. for C$_{37}$H$_{48}$N$_6$O$_{13}$.2H$_2$O: C, 54.14; H, 6.39; N, 10.24. Found: C, 53.81; H, 6.16; N, 9.99.

Example 12J (2S,3S)-2-(Dibenzylcarbamoyl)-3-(N$^2$-(N-benzyloxycarbonylleucylglutamylthreonyl)-N$^1$-carboxymethylhydrazinocarbonyl)oxirane (Cbz-Leu-Glu-Thr-AAsp-(2S,3S)-EP-CON(Bzl)$_2$). $^1$H NMR (DMSO-d$_6$): 0.84 (t, 6H, Leu CH$_3$), 1.03 (m, 3H, Thr CH$_3$), 1.42 (m, 2H, Leu CH$_2$), 1.60 (m, 1H, Leu CH), 1.76 and 1.92 (d of m, 2H, Glu CH$_2$), 2.24 (m, 2H, Glu, CH$_2$), 3.32 (s, 2H, AAsp CH$_2$), 3.76 (s, 2H, epoxy), 4.03 (b, 2H, α-H), 4.11 (s, 1H, α-H), 4.28–4.55 (m, 5H, Thr CH and CH$_2$Ph), 5.00 (s, 2H, Z), 7.18–7.43 (m, 16H, Ph and NH), 7.78 (b, 1H, NH), 8.07 (b, 2H, NH), 10.85 (b, 2H. COOH). HRMS (FAB) Calcd. for C$_{43}$H$_{53}$N$_6$O$_{13}$: 861.3671. Observed m/z 861.3649. Anal. Calcd. for C$_{43}$H$_{52}$N$_6$O$_{13}$.H$_2$O: C, 58.76; H, 6.19; N, 9.56. Found: C, 58.87; H, 6.01; N, 9.37.

Example 12K (2S,3S)-2-(N-Methyl-N-benzylcarbamoyl)-3-(N$^2$-(N-benzyloxycarbonylisoleucylglutamylthreonyl)-N$^1$-carboxymethylhydrazinocarbonyl)oxirane (Cbz-Ile-Glu-Thr-AAsp-(2S,3S)-EP-CO—N(CH$_3$)Bzl). $^1$H NMR (DMSO-d$_6$): 0.79 (t, 6H, Ile CH$_3$), 1.09 (m, 5H, Thr CH$_3$ and Ile CH$_2$), 1.40 (m, 1H, Ile CH), 1.71 and 1.92 (d of m, 2H, Glu CH$_2$), 2.25 (m, 2H, Glu CH$_2$), 2.79 and 2.98 (d, 3H, NCH$_3$), 3.32 (s, 2H, AAsp CH$_2$), 3.80–4.10 (m, 5H, epoxy and α-H), 4.27 (d, 1H, Thr CH), 4.39 (m, 2H, CH$_2$Ph), 5.00 (s, 2H, Z), 7.15–7.40 (m, 11H, Ph and NH), 7.80 (b, 1H, NH), 8.07 (b, 2H, NH), 10.80 (b, 2H. COOH). HRMS (FAB) Calcd. for C$_{37}$H$_{49}$N$_6$O$_{13}$: 785.3358. Observed m/z 785.3401. Anal. Calcd. for C$_{37}$H$_{48}$N$_6$O$_{13}$.2H$_2$O: C, 54.14; H, 6.39; N, 10.24. Found: C, 53.26; H, 6.12; N, 9.90.

Example 12L (2S,3S)-2-(Dibenzylcarbamoyl)-3-(N$^2$-(N-benzyloxycarbonylisoleucylglutamylthreonyl)-N$^1$-carboxymethylhydrazinocarbonyl)oxirane (Cbz-Ile-Glu-Thr-AAsp-(2S,3S)-EP-CO—N(Bzl)$_2$). $^1$H NMR (DMSO-d$_6$): 0.82 (m, 6H,Ile CH$_3$), 1.02 (m, 3H, Thr CH$_3$), 1.10 (m, 2H, Ile CH$_2$), 1.40 (m, 1H, Ile CH), 1.75 and 1.85 (d of m, 2H, Glu CH$_2$), 2.24 (m, 2H, Glu CH$_2$), 3.32 (s, 2H, AAsp CH$_2$), 3.61 and 3.76 (d, 2H, epoxy), 3.88 (b, 2H, α-H), 4.00 (m, 1H, α-H), 4.30–4.55 (m, 5H, Thr CH and CH$_2$Ph), 5.00 (s, 2H, Z), 7.15–7.45 (m, 17H, Ph and NH), 7.85 (d, 1H, NH), 9.55 (s, 1H, NH), 10.85 (b, 2H. COOH). HRMS (FAB) Calcd. for C$_{43}$H$_{53}$N$_6$O$_{13}$: 861.36706. Observed m/z 861.36964. Anal. Calcd. for C$_{43}$H$_{52}$N$_6$O$_{13}$.2H$_2$O: C, 57.58; H, 6.29; N, 9.37. Found: C, 57.62; H, 5.95; N, 9.24.

Example 13 cis-3-(N-(N-Benzyloxycarbonylleucyl)-N$^1$-phenylethylhydrazinocarbonyl)oxirane-2-carboxylic Acid Ethyl Ester (Cbz-Leu-AHph-cis-EP-COOEt). This compound was obtained using the EDC/HOBt coupling method and purified by chromatography on a silica gel column using 1:29:10 MeOH:CH$_2$Cl$_2$:EtOAc as the eluting solvent system; white solid, yield 20%. $^1$H NMR (CDCl$_3$): 0.95 (t, 6H, Leu), 1.25 (t, 3H, OCH$_2$CH$_3$), 1.40–1.90 (m, 3H, Leu), 2.80–2.90 (m, 2H, CH$_2$Ph), 3.50 and 3.55 (d, 2H, epoxy), 3.60 (m, 2H, NCH$_2$CH$_2$Ph), 4.00 (m, 1H, α-H), 4.20 (q, 2H, OCH$_2$CH$_3$), 5.20 (m, 2H, Cbz), 5.30 (m, 1H, NH), 7.16–7.37 (m, 101H, Ph), 8.1 (m, 1H, NH). HRMS (FAB) Calcd. for C$_{28}$H$_{36}$N$_3$O$_7$: 526.2553. Observed m/z 526.2551.

Example 14

(2S,3S)-3-(N$^2$-(N-Benzyloxycarbonylleucyl)-N$^1$-phenylethylhydrazinocarbonyl)oxirane-2-carboxylic Acid Ethyl Ester (Cbz-Leu-AHph-(2S,3S)-EP-COOEt). This compound was obtained using the EDC/HOBt coupling method and purified by chromatography on a silica gel column using 1:32:7 MeOH:CH$_2$Cl$_2$:EtOAc as the eluting solvent system; white solid, yield 48%. $^1$H NMR (CDCl$_3$): 0.95 (t, 6H, Leu), 1.25 (t, 3H, OCH$_2$CH$_3$), 1.40–1.90 (m, 3H, Leu), 2.80–2.90 (m, 2H, CH$_2$Ph), 3.56 and 3.76 (d, 2H, epoxy), 3.60 and 3.90 (m, 2H, NCH$_2$CH2Ph), 4.00 (m, 1H, α-H), 4.20 (q, 2H, OCH$_2$CH$_3$), 5.00 (d, 1H, NH), 5.20 (m, 2H, Cbz), 7.16–7.37 (m, 10H, Ph), 8.1 (m, 1H, NH). HRMS (FAB) Calcd. for C$_{28}$H$_{36}$N$_3$O$_7$: 526.2553. Observed m/z 526.2516.

Example 15

(2R,3R)-3-(N$^2$-(N-Benzyloxycarbonylleucyl)-N$^1$-phenylethylhydrazinocarbonyl)oxirane-2-carboxylic Acid Ethyl Ester (Cbz-Leu-AHph-(2R,3R)-EP-COOEt). This compound was obtained using the EDC/HOBt coupling method and purified by chromatography on a silica gel column using 1:29:10 MeOH:CH$_2$Cl$_2$:EtOAc as the eluting solvent system; white solid, yield 64%. $^1$H NMR (CDCl$_3$): 0.95 (t, 6H, Leu), 1.25 (t, 3H, OCH$_2$CH$_3$), 1.40–1.90 (m, 3H, Leu), 2.80–2.90 (m, 2H, CH$_2$Ph), 3.58 and 3.80 (d, 2H, epoxy), 3.60 and 3.90 (m, 2H, NCH$_2$CH2Ph), 4.00 (m, 1H, α-H), 4.20 (q, 2H, OCH$_2$CH$_3$), 4.80 (d, 1H, NH), 5.20 (m, 2H, Cbz), 7.16–7.37 (m, 10H, Ph), 7.90 (m, 1H, NH). HRMS (FAB) Calcd. for $C_{28}H_{36}N_3O_7$: 526.2553. Observed m/z 526.2538.

Example 16

(2S,3S)-3-($N^2$-(N-Benzyloxycarbonyleucyl)-$N^1$-phenylethylhydrazinocarbonyl)oxirane-2-carboxylic Acid (Cbz-Leu-AHph-(2S,3S)-EP-COOH). This compound was recrystallized using (1:19 MeOH:$CH_2Cl_2$)/hexane to yield a white solid, yield 92%. $^1H$ NMR (DMSO-$d_6$): 0.95 (t, 6H, Leu), 1.40–1.90 (m, 3H, Leu), 2.80–2.90 (m, 2H, $CH_2$Ph), 3.56 and 3.80 (d, 2H, epoxy), 3.60 and 3.90 (m, 2H, $NCH_2CH2Ph$), 4.00 (m, 1H, α-H), 5.00 (d, 1H, NH), 5.20 (m, 2H, Cbz), 7.16–7.37 (m, 5H, Ph), 8.1 (m, 1H, NH), 11.00 (s, 1H, COOH). HRMS (FAB) Calcd. for $C_{26}H_{32}N_3O_7$: 498.2240. Observed m/z 498.2252.

Example 17

(2R,3R)-3-($N^2$-(N-Benzyloxycarbonyleucyl)-$N^1$-isobutylhydrazinocarbonyl)oxirane-2-carboxylic Acid Ethyl Ester (Cbz-Leu-ALeu-(2R,3R)-EP-COOEt). This compound was obtained using the EDC/HOBt coupling method and purified by chromatography on a silica gel column using 1:29:10 MeOH:$CH_2Cl_2$:EtOAc as the eluting solvent system; white solid, yield 51%. $^1H$ NMR ($CDCl_3$): 0.95 (m, 12H, Leu and ALeu), 1.25 (t, 3H, $OCH_2CH_3$), 1.40–1.90 (m, 4H, Leu and ALeu), 3.20 and 3.50 (m, 2H, $NCH_2CH$), 3.60 and 3.90 (d, 2H, epoxy), 4.10 (m, 1H, α-H), 4.20 (q, 2H, $OCH_2CH_3$), 4.90 (d, 1H, NH), 5.10 (m, 2H, Cbz), 7.16–7.37 (m, 5H, Ph), 8.40 (m, 1H, NH). HRMS (FAB) Calcd. for $C_{24}H_{36}N_3O_7$: 478.2553 Observed m/z 478.2550.

Example 18 cis-3-($N^2$-(N-Benzyloxycarbonyleucyl)-$N^1$-isobutylhydrazinocarbonyl)oxirane-2-carboxylic Acid Ethyl Ester (Cbz-Leu-ALeu-cis-EP-COOEt). This compound was obtained using the EDC/HOBt coupling method and purified by chromatography on a silica gel column using 1:2 EtOAc:$CH_2Cl_2$ as the eluting solvent system; white solid, yield 40%. $^1H$ NMR ($CDCl_3$): 0.95 (m, 12H, Leu and ALeu), 1.25 (t, 3H, $OCH_2CH_3$), 1.40–1.90 (m, 4H, Leu and ALeu), 3.20 and 3.50 (m, 2H, $NCH_2CH$), 3.50 and 3.55 (d, 2H, epoxy), 4.10 (m, 1H, α-H), 4.20 (q, 2H, $OCH_2CH_3$), 5.10 (m, 1H, NH), 5.20 (m, 2H, Cbz), 7.16–7.37 (m, 5H, Ph), 8.1 (m, 1H, NH). HRMS (FAB) Calcd. for $C_{24}H_{36}N_3O_7$: 478.2553. Observed m/z 478.2573.

Example 19 trans-3-($N^2$-(N-Benzyloxycarbonylleucylphenylalanyl)-$N^1$-carbamoylethylhydrazinocarbonyl)oxirane-2-carboxylic Acid Ethyl Ester (Cbz-Leu-Phe-AGln-trans-EP-COOEt). This compound was obtained using the EDC/HOBt coupling method and purified by chromatography on a silica gel column using 1:19 MeOH:$CH_2Cl_2$ as the eluting solvent system; white solid, yield 30%. $^1H$ NMR (DMSO-$d_6$): 0.8 (t, 6H, $CH_3$), 1.1–1.2 (m, 3H, $OCH_2CH_3$), 1.2–1.4 (m, 2H, Leu $CH_2$), 1.5 (m, 1H, Leu $CH(CH_3)_2$), 2–2.4 (m, 2H, $NCH_2CH_2CO$), 2.8–3.0 (m, 2H, Phe $CH_2$), 3.2–3.4 (m, 2H, $NCH_2CH_2CO$), 3.5 (s, 1H, epoxy), 3.8 (m, 1H, α-CH), 4.0–4.2 (m, 3H, epoxy and $OCH_2CH_3$), 4.25–4.35 (m, α-H and NH), 5.0 (s, 2H, Cbz), 6.85 (m, 1H, NH), 7.2–7.4 (m, 10H, Ph), 8.25 (m, 1H, NH). MS (FAB) m/z 640 [(M+1)$^+$]. HRMS (FAB) Calcd. for $C_{32}H_{42}N_5O_9$: 640.29825. Observed m/z 640.29854. Anal. Calcd. for $C_{32}H_{41}N_5O_9$·$0.5H_2O$: C, 59.26; H, 6.48; N, 10.8. Found: C, 59.47; H, 6.48; N, 10.50.

Example 20

(2S,3S)-3-($N^2$-(N-Benzyloxycarbonylleucylphenylalanyl)-$N^1$-carbamoylethylhydrazinocarbonyl)oxirane-2-carboxylic Acid Ethyl Ester (Cbz-Leu-Phe-AGln-(2S,3S)-EP-COOEt). This compound was obtained using the EDC/HOBt coupling method and purified by chromatography on a silica gel column using 1:13 MeOH:$CH_2Cl_2$ as the eluting solvent system; white solid, yield 72%. $^1H$ NMR (DMSO-$d_6$): 0.8 (t, 6H, $CH_3$), 1.18 (t, 3H, $OCH_2CH_3$), 1.2–1.4 (m, 2H, Leu $CH_2$), 1.42–1.55 (m, 1H, Leu $CH(CH_3)_2$), 2.05–2.3 (m, 2H, $NCH_2CH_2CO$), 2.8–3.0 (m, 2H, Phe $CH_2$), 3.4–3.6 and 3.7 (m, 2H, $NCH_2CH_2CO$), 3.5 (m, 1H, epoxy), 4.0 (m, 1H, α-CH), 4.05–4.2 (m, 3H, epoxy and $OCH_2CH_3$), 4.35–4.53 (m, 2H, α-H and NH), 5.0 (s, 2H, Cbz), 6.9 (m, 1H, NH), 7.18–7.42 (m, 10H, Ph), 8.3 (m, 1H, NH). MS (FAB) m/z 640 [(M+1)$^+$]. HRMS (FAB) Calcd. for $C_{32}H_{42}N_5O_9$: 640.29825. Observed m/z 640.29635. Anal. Calcd. for $C_{32}H_{41}N_5O_9$: C, 60.08; H, 6.46; N, 10.95. Found: C, 60.12; H, 6.46; N, 10.72.

Example 21

(2R,3R)-3-($N^1$-(N-Benzyloxycarbonylleucylphenylalanyl)-$N^1$-carbamoylethylhydrazinocarbonyl)oxirane-2-carboxylic Acid Ethyl Ester (Cbz-Leu-Phe-AGln-(2R,3R)-EP-COOEt). This compound was obtained using the EDC/HOBt coupling method and purified by chromatography on a silica gel column using 1:13 MeOH:$CH_2Cl_2$ as the eluting solvent system; white solid, yield 35%. $^1H$ NMR (DMSO-$d_6$): 0.8 (t, 6H, $CH_3$), 1.18 (t, 3H, $OCH_2CH_3$), 1.3–1.4 (m, 2H, Leu $CH_2$), 1.42–1.6 (m, 1H, Leu $CH(CH_3)_2$), 2–2.3 (m, 2H, $NCH_2CH_2CO$), 2.8–3.1 (m, 2H, Phe $CH_2$), 3.3–3.4 and 3.55–3.65 (m, 2H, $NCH_2CH_2CO$), 3.45 (s, 1H, epoxy), 3.83 (m, 1H, α-CH), 4.0–4.2 (m, 3H, epoxy and $OCH_2CH_3$), 4.3–4.5 (m, 2H, α-H and NH), 5.0 (s, 2H, Cbz), 6.85 (m, 1H, NH), 7.2–7.4 (m, 10H, Ph), 8.3 (m, 1H, NH). MS (FAB) m/z 640 [(M+1)$^+$]. HRMS (FAB) Calcd. for $C_{32}H_{42}N_5O_9$: 640.29825. Observed m/z 640.30011. Anal. Calcd. for $C_{32}H_{41}N_5O_9$: C, 60.08; H, 6.46; N, 10.95. Found: C, 60.21; H, 6.49; N, 10.74.

Example 22 trans-3-($N^2$-(N-Benzyloxycarbonylalanylalanyl)-$N^1$-ethoxycarbonylmethylhydrazinocarbonyl)oxirane-2-carboxylic Acid Ethyl Ester (Cbz-Ala-Ala-AAsp(OEt)-trans-EP-COOEt). This compound was obtained using the EDC/HOBt coupling method and purified by chromatography on silica gel column using 1:9 MeOH:$CH_2Cl_2$ as the eluting solvent system; recrystallized from EtOAc/hexane; white solid, yield 19%. $^1H$ NMR ($CDCl_3$): 1.2–1.4 (m, 12H, $CH_3$), 3.4– 3.6 (m, 2H, $NCH_2CO$), 3.6 (s, 1H, epoxy), 3.92 (s, 1H, epoxy), 4.1–4.3 (m, 5H, α-H and 2×$OCH_2CH_3$), 4.4 (m, 1H, α-H), 5.13 (m, 2H, Cbz), 6.5 (m, 1H, NH), 7.2 (m, 1H, NH), 7.35 (s, 5H, Ph), 9.0 (m, 1H, NH). MS (FAB) m/z 537 [(M+1)$^+$]. HRMS (FAB) Calcd. for $C_{24}H_{33}N_4O_{10}$: 537.21967. Observed m/z 537.22012. Anal. Calcd. for $C_{24}H_{32}N_4O_{10}$·$0.75H_2O$: C, 52.41; H, 6.096; N, 10.19. Found: C, 52.61; H, 5.93; N, 9.98.

Example 23 trans-3-(N²-(N-Benzyloxycarbonylalanylalanyl)-N¹-carbamoylmethylhydrazinocarbonyl)oxirane-2-carboxylic Acid Benzyl Ester (Cbz-Ala-Ala-AAsn-trans-EP-COOBzl). This compound was obtained using the EDC/HOBt coupling method and purified by chromatography on a silica gel column using 1:7 MeOH:CH$_2$Cl$_2$ as the eluting solvent system; recrystallized from EtOAc/hexane; white solid, yield 4%. $^1$H NMR (DMSO-d$_6$): 1–1.3 (m, 6H, CH$_3$), 3.25–3.4 and 3.5–3.7 (m, 3H, epoxy and NCH$_2$CO), 3.98 (d, 1H, epoxy), 4.0–4.1 (m, 1H, α-H), 4.2 (m, 1H, α-H), 5.0 and 5.2 (m, 4H, OCH$_2$Ph), 7.2–7.5 (m, 11H, NH and Ph), 7.55 (m, 1H, NH), 8.2 (m, 1H, NH). HRMS (FAB) Calcd. for C$_{27}$H$_{32}$N$_5$O$_9$: 570.22000. Observed m/z 570.21623. Anal. Calcd. for C$_{27}$H$_{31}$N$_5$O$_9$.0.6H$_2$O: C, 55.88; H, 5.55; N, 12.07. Found: C, 56.21; H, 5.68; N, 11.69.

Example 24 trans-3-(N²-(N-tert-Butoxycarbonyl-2-naphthylalanyl)-N¹-isobutylhydrazinocarbonyl)oxirane-2-carboxylic Acid Ethyl Ester (Boc-Np2-ALeu-trans-EP-COOEt). This compound was obtained using the EDC/HOBt coupling method and purified by chromatography on a silica gel column using 1:2 EtOAc:CH$_2$Cl$_2$ as the eluting solvent system; 78% yield. $^1$H NMR (CDCl$_3$): 0.6–0.9 (m, 6H, Leu CH$_3$), 1.3–1.5 (m, 4H, Leu CH and OCH$_2$CH$_3$), 2.2–2.5 (m, 4H, Suc CH$_2$), 3.0–3.4 (m, 4H, Np2 CH$_2$ and NCH$_2$CO), 3.5 (s, 1H, epoxy), 4.03–4.2 (m, 3H, OCH$_2$CH$_3$ and epoxy), 4.4–4.6 (m, 1H, α-H), 4.6–4.7 (m, 1H, NH), 7.4–7.5 and 7.7–7.9 (m, 7H, Ph), 8.5 (m, 1H, NH), HRMS (FAB) Calcd. for C$_{28}$H$_{38}$N$_3$O$_7$: 528.27098. Observed m/z 528.27138.

Example 25 trans-3-(N²⁻²-Naphthylalanyl)-N¹-isobutylhydrazinocarbonyl)oxirane-2-carboxylic Acid Ethyl Ester Trifluoracetate Salt (Np2-ALeu-trans-EP-COOEt-TFA). The blocked epoxysuccinyl peptide Boc-Np2-ALeu-trans-EP-COOEt was dissolved in a small amount of TFA at 0° C. After 15 minutes, the excess TFA was removed under vacuum. MS (FAB⁺) m/z 428 (M−TFA+1, 60%).

Example 26 trans-3-(N²-(N-Succinyl-2-naphthylalanyl)-N¹-isobutylhydrazinocarbonyl)oxirane-2-carboxylic Acid Ethyl Ester (Suc-Np2-ALeu-trans-EP-COOEt). To a stirred solution of Np2-ALeu-trans-EP-COOEt-TFA (1 eq) in DMF at −10° C. was added succinic anhydride (1.1 eq), followed by NMM (1 eq). The reaction was left to stir at room temperature for 16 hours, and purified by chromatography on a silica gel column using 1:9 MeOH:CH$_2$Cl$_2$ as the eluting solvent system; 34% yield. $^1$H NMR (DMSO-d$_6$): 0.2–0.9 (m, 6H, Leu CH$_3$), 1.1–1.3 (m, 4H, Leu CH and OCH$_2$CH$_3$), 2.2–2.5 (m, 4H, Suc CH$_2$), 3.0–3.4 (m, 4H, Np2 CH$_2$ and NCH$_2$CO), 3.5 (s, 1H, epoxy), 4.03–4.2 (m, 3H, OCH$_2$CH$_3$ and epoxy), 4.4–4.6 (m, 1H, α-H), 4.6–4.7 (m, 1H, NH), 7.4–7.5 and 7.7–7.9 (m, 7H, Ph), 8.5 (m, 1H, NH), 10.8 (m, COOH). HRMS (FAB) Calcd. for C$_{27}$H$_{34}$N$_3$O$_8$: 528.23459. Observed m/z 528.23471. Anal. Calcd. for C$_{27}$H$_{33}$N$_3$O$_8$1.5H$_2$O: C, 58.5; H, 6.50; N, 7.58. Found: C, 58.77; H, 6.26; N, 7.27.

Example 27 trans-3-(N²-(N-Benzyloxycarbonyl)-N¹-isobutylhydrazinocarbonyl)oxirane-2-carboxylic Acid Ethyl Ester (Cbz-ALeu-trans-EP-COOEt). This compound was obtained using the EDC/HOBt coupling method and purified by chromatography on a silica gel column using 1:4 EtOAc: CH$_2$Cl$_2$ as the eluting solvent system; 19% yield. $^1$H NMR (CDCl$_3$): 0.9 (d, 6H, CH$_3$), 1.3 (t, 3H, OCH$_2$CH$_3$), 1.7 (m, 1H, CH(CH$_3$)$_2$), 2.6–2.7 (m, 2H, N—CH$_2$), 3.55 (d, 1H, epoxy), 4.2–4.3 (q, 2H, OCH$_2$CH$_3$), 4.5 (d, 1H, epoxy), 5.3 (m, 2H, Cbz), 7.3–7.5 (m, 5H, Ph). HRMS (FAB) Calcd. for C$_{18}$H$_{25}$N$_2$O$_6$: 365.17126. Observed m/z 365.17315. Anal. Calcd. for C$_{18}$H$_{24}$N$_2$O$_6$: C, 59.33; H, 6.64; N, 7.69. Found: C, 59.31; H, 6.58; N, 7.66.

Example 28 trans-3-(N²-(N-Benzyloxycarbonyl)-N¹-phenylethylhydrazinocarbonyl)oxirane-2-carboxylic Acid Ethyl Ester (Cbz-AHph-trans-EP-COOEt). This compound was obtained using the EDC/HOBt coupling method and purified by chromatography on a silica gel column using 1:4 EtOAc: CH$_2$Cl$_2$ as the eluting solvent system; 6% yield. $^1$H NMR (CDCl$_3$): 1.3–1.4 (t, 3H, OCH$_2$CH$_3$), 2.8 (t, 2H, CH$_2$), 3.15 (t, 2H, CH$_2$), 3.55 (d, 1H, epoxy), 4.3 (q, 2H, OCH$_2$CH$_3$), 4.45 (d, 1H, epoxy), 5.3 (m, 2H, Cbz), 7.1 (m, 1H, NH), 7.2–7.4 (m, 10H, Ph). HRMS (FAB) Calcd. for C$_{22}$H$_{25}$N$_2$O$_6$: 413.17126. Observed m/z 413.17251. Anal. Calcd. for C$_{22}$H$_{24}$N$_2$O$_6$.1.04H$_2$O: C, 61.29; H, 6.05; N, 6.50. Found: C, 61.65; H, 5.82; N, 6.05.

Example 29 trans-3-(N²-(N-Acetyl)-N¹-phenylethylhydrazinocarbonyl)oxirane-2-carboxylic Acid Ethyl Ester (Ac-AHph-trans-EP-COOEt). This compound was obtained using the EDC/HOBt coupling method and purified by chromatography on a silica gel column using 1:19 MeOH:CH$_2$Cl$_2$ as the eluting solvent system; 46% yield. $^1$H NMR (CDCl$_3$): 1.25–1.35 (t, 3H, OCH$_2$CH$_3$), 1.82 (s, 3H, CH$_3$), 2.82–3.0 (m, 2H, CH$_2$), 3.55–3.7 (m, 2H, CH$_2$), 3.63 (d, 1H, epoxy), 3.77 (d, 1H, epoxy), 4.2–4.3 (q, 2H, OCH$_2$CH$_3$), 6.9 (m, 1H, NH), 7.15–7.4 (m, 5H, Ph). HRMS (EI) Calcd. for C$_{16}$H$_{20}$N$_2$O$_5$: 320.13722. Observed m/z 320.13135. Anal. Calcd. for C$_{16}$H$_{20}$N$_2$O$_5$.0.1H$_2$O: C, 59.66; H, 6.28; N, 8.70. Found: C, 59.40; H, 6.46; N, 9.11.

Example 30 trans-3-(N²-(N-Acetylleucyl)-N¹-isobutylhydrazinocarbonyl)oxirane-2-carboxylic Acid Ethyl Ester (Ac-Leu-ALeu-trans-EP-COOEt). This compound was obtained using the EDC/HOBt coupling method and purified by column chromatography using 1:19 MeOH:CH$_2$Cl$_2$ as an eluent, and was then rechromatographed using 4:1 EtOAc: CH$_2$Cl$_2$ as the eluent; white solid, 35% yield. $^1$H NMR (CDCl$_3$): 0.8–1.0 (m, 12H, CH$_3$), 1.2–1.4 (m, 3H, OCH$_2$CH$_3$), 1.5–1.9 (m, 3H, Leu CH$_2$ and CH(CH$_3$)$_2$), 2.05 (d, 3H, CH$_3$CO), 3.2–3.3 and 3.4–3.5 (m, 2H, N—CH$_2$), 3.6 (d, 1H, epoxy), 3.85 (d, 1H, epoxy), 4.2–4.3 (m, 2H, OCH$_2$CH$_3$), 4.4–4.55 (m, 1H, α-H), 6.1 (m, 1H, NH), 9.1 (m, 1H, NH). HRMS (FAB) Calcd. for C$_{22}$H$_{32}$N$_3$O$_6$: 434.22911. Observed m/z 434.23111. Anal. Calcd. for C$_{18}$H$_{31}$N$_3$O$_6$: C, 56.09; H, 8.11; N, 10.90. Found: C, 55.99; H, 8.12; N, 10.61.

Example 31 trans-3-($N^2$-(N-Acetylleucyl)-$N^1$-phenylethylhydrazinocarbonyl)oxirane-2-carboxylic Acid Ethyl Ester (Ac-Leu-AHph-trans-EP-COOEt). This compound was obtained using the EDC/HOBt coupling method and purified by chromatography on a silica gel column using 1:19 MeOH:CH$_2$Cl$_2$ as the eluting solvent system; white solid, 23% yield. $^1$H NMR (CDCl$_3$): 0.85–1.0 (m, 6H, CH$_3$), 1.22–1.32 (m, 3H, OCH$_2$CH$_3$), 1.42–1.7 (m, 3H, Leu CH$_2$ and CH(CH$_3$)$_2$), 2.03 (d, 3H, CH$_3$CO), 2.8–3.0 (m, 2H, CH$_2$), 3.58 (d, 1H, epoxy), 3.78 (d, 1H, epoxy), 3.7–3.8 and 3.8–4.0 (m, 2H, CH$_2$), 4.2–4.4 (m, 3H, OCH$_2$CH$_3$ and α-H), 5.8 (m, 1H, NH), 7.18–7.4 (m, 5H, Ph), 8.55 (m, 1H, NH). HRMS (FAB) Calcd. for C$_{22}$H$_{32}$N$_3$O$_6$: 434.22911. Observed m/z 434.23111. Anal. Calcd. for C$_{22}$H$_{31}$N$_3$O$_6$: C, 60.95; H, 7.21; N, 9.69. Found: C, 60.72; H, 7.29; N, 9.56.

Example 32

(2S,3S)-3-($N^2$-(N-Benzyloxycarbonylisoleucylglutamylthreonyl)-$N^1$-carboxymethylhydrazinocarbonyl)oxirane-2-carboxylic Acid Ethyl Ester (Cbz-Ile-Glu-Thr-AAsp-(2S,3S)-EP-COOEt). This compound was obtained using the mixed anhydride coupling method and the t-butyl esters were deblocked using the procedure previously described. $^1$H NMR (DMSO-d$_6$): 0.8 (m, 6H, Ile CH$_3$), 1–1.2 (m, 4H, Thr CH$_3$ and Ile CH$_2$), 1.2 (t, 3H, OCH$_2$CH$_3$), 1.4 (m, 1H, Ile CH$_2$), 1.6–1.8 (m, 2H, CH Ile and Glu CH$_2$), 1.8–1.9 (m, 1H, Glu CH$_2$), 2.1–2.3 (m, 2H, Glu CH$_2$), 3.5 (d, 1H, epoxy), 3.85–4.05 (m, 3H, NCH$_2$COOH and CH—OH), 4.1 (d, 1H, epoxy), 4.1–4.3 (m, 3H, OCH$_2$CH$_3$ and α-H), 4.3–4.45 (m, 2H, α-H), 4.6 (m, 1H, NH), 4.9 (m, 1H, NH), 5.05 (m, 2H, Cbz), 7.30–7.40 (m, 5H, Ph), 7.80 (m, 1H, NH), 8.1 (m, 1H, NH), 11.00 (m, COOH). HRMS (FAB) Calcd. for C$_{31}$H$_{44}$N$_5$O$_{14}$: 710.28848. Observed m/z 710.29205. Anal. Calcd. for C$_{31}$H$_{43}$N$_5$O$_{14}$.2H$_2$O: C, 49.93; H, 6.31; N, 9.40. Found: C, 49.71; H, 6.12; N, 9.42.

Example 33

(2R,3R)-3-($N^2$-(N-Benzyloxycarbonylisoleucylglutamylthreonyl)-$N^1$-carboxymethylhydrazinocarbonyl)oxirane-2-carboxylic Acid Ethyl Ester (Cbz-Ile-Glu-Thr-AAsp-(2R,3R)-EP-COOEt). This compound was obtained using the mixed anhydride coupling method and the t-butyl esters were deblocked using the procedure previously described. $^1$H NMR (D.MSO-d$_6$): 0.8 (m, 6H, Ile CH$_3$), 1.0 (d, 3H, Thr CH$_3$), 1–1.2 and 1.4 (m, 2H, Ile CH$_2$), 1.2 (t, 3H, OCH$_2$CH$_3$), 1.65–1.8 (m, 2H, CH Ile and Glu CH$_2$), 1.8–2.0 (m, 1H, Glu CH$_2$), 2.1–2.3 (m, 2H, Glu CH$_2$), 3.5 (d, 1H, epoxy), 3.8–4.0 (m, 3H, NCH$_2$COOH and CH—OH), 4.05 (d, 1H, epoxy), 4.1–4.23 (m, 3H, OCH$_2$CH$_3$ and α-H), 4.3–4.45 (m, 2H, α-H), 5.05 (m, 2H, Cbz), 7.30–7.40 (m, 5H, Ph), 7.80 (m, 1H, NH), 8.1 (m, 1H, NH), 11.00 (m, COOH). HRMS (FAB) Calcd. for C$_{31}$H$_{44}$N$_5$O$_{14}$: 710.28848. Observed m/z 710.28779. Anal. Calcd. for C$_{31}$H$_{43}$N$_5$O$_{14}$.1H$_2$O: C, 51.17; H, 6.19; N, 9.63. Found: C, 51.07; H, 6.10; N, 9.55.

Example 34 trans-3-(N-(N-tert-Butoxycarbonylnorvalyl)-$N^1$-phenylethylhydrazinocarbonyl)oxirane-2-carboxylic Acid Ethyl Ester (Boc-Nva-AHph-trans-EP-COOEt). To a stirred solution of ethyl trans-epoxysuccinate (1 eq), HOBt (1 eq) and Boc-Nva-NHNH—CH$_2$CH$_2$Ph (1 eq) in DMF was added EDC (1.1 eq), and the reaction mixture was stirred at room temperature for 16 hours. The DMF was evaporated in vacuo and the residue was dissolved in EtOAc (20 ml), and washed with 1 N HCl, 4% NaHCO$_3$, and brine, dried over MgSO$_4$, and concentrated. The residue was purified by column chromatography and the product was eluted with 1:49 MeOH:CH$_2$Cl$_2$; white solid, yield 33%; TLC R$_f$=0.4 (1:49 MeOH:CH$_2$Cl$_2$); $^1$H-NMR (CDCl$_3$): 0.9–1.0 (t, 3H), 1.2–1.4 (m, 5H), 1.4 (s, 9H), 1.5–1.8 (m, 2H), 2.8–3.0 (m, 2H), 3.6 (s, 1H), 3.7–3.9 (2s, 1H), 3.9–4.0 (m, 1H), 4.2–4.3 (m, 2H), 4.7–4.8 (m, 1H), 7.2–7.4 (m, 5H), 8.3–8.4 (2s, 1H). MS (FAB$^+$) 424 (M−tBu+1, 40%), 378 (M−Boc+1, 35%).

Example 35 trans-3-($N^2$-(N-tert-Butoxycarbonylnorleucyl)-$N^1$-phenylethylhydrazinocarbonyl)oxirane-2-carboxylic Acid Ethyl Ester (Boc-Nle-AHph-trans-EP-COOEt). This compound was prepared by the EDC/HOBt coupling method. It was purified by column chromatography using 1:49 MeOH:CH$_2$Cl$_2$ as an eluent, and was then rechromatographed using EtOAc:CH$_2$Cl$_2$=1:1 as the eluent; white solid, yield 22%; TLC R$_f$=0.7 (1:1 EtOAc:CH$_2$Cl$_2$); $^1$H-NMR (CDCl$_3$): 0.8–1.0 (t, 3H), 1.2–1.4 (m, 4H), 1.4 (s, 9H), 1.4–1.8 (m, 2H), 2.8–3.0 (m, 2H), 3.6 (s, 1H), 3.8–3.9 (2s, 1H), 3.8–4.0 (m, 2H), 4.2–4.3 (m, 2H), 4.7–4.8 (m, 1H), 7.2–7.4 (m, 5H), 8.3 (b, 1H), 8.5 (b, 1H). MS (FAB$^+$) 492 (M+1, 80%), 436 (M−tBu+1, 100%).

Example 36 trans-3-($N^2$-(N-tert-Butoxycarbonylnorvalyl)-$N^1$-phenylethylhydrazinocarbonyl)-2-(2-phenylethyl)oxirane (Boc-Nva-AHph-trans-EP-CH$_2$CH$_2$Ph). This compound was prepared by the EDC/HOBt coupling method. It was purified by column chromatography using 1:49 MeOH:CH$_2$Cl$_2$ as an eluent, and was then rechromatographed using 1:1 EtOAc:CH$_2$Cl$_2$ as the eluent; white solid, yield 38%; TLC R$_f$=0.75 (1:1 EtOAc:CH$_2$Cl$_2$); $^1$H-NMR (CDCl$_3$): 0.9–1.0 (t, 3H), 1.2–1.4 (m, 2H), 1.4 (2s, 9H), 1.6–1.9 (m, 2H), 2.7–2.9 (m, 4H), 3.1 (s, 1H), 3.3 &3.4 (2s, 1H), 3.6–3.8 (m, 1H), 3.8–4.0 (m, 2H), 4.7–4.8 (m, 1H), 7.1–7.4 (m, 10H), 7.9, 8.1 (s, 1H). MS (FAB$^+$) 510 (M+1, 20%), 454 (M−tBu+1, 100%).

Example 37 trans-3-($N^2$-(N-tert-Butoxycarbonyl-α-aminobutanoyl)-$N^1$-phenylethylhydrazinocarbonyl)-2-(2-phenylethyl)oxirane (Boc-Abu-AHph-trans-EP-CH$_2$CH$_2$Ph). This compound was obtained using the EDC/HOBt coupling method and purified by chromatography on a silica gel column using 1:9 MeOH:CH$_2$Cl$_2$ as the eluting solvent system; white solid, yield 39%. $^1$H NMR (CDCl$_3$): 1.00 (t, 3H, Abu), 1.4 (2s, 9H), 1.6 (m, 2H, EP-CH$_2$), 1.7–1.9 (m, 2H, Abu), 2.7–2.9 (m, 4H, CH$_2$Ph), 3.1 (s, 1H, epoxide), 3.3 and 3.4 (2s, 1H, epoxide), 3.6–3.8 (m, 2H NCH$_2$CH$_2$), 4.1 (m, 1H, αH), 7.1–7.4 (m, 10 H), 7.9 and 8.1 (s, 1H, NH). MS (FAB$^+$) 496 (M+1, 80%), 440 (M−tBu+1, 60%). HRMS (FAB) Calcd. for C$_{28}$H$_{38}$N$_3$O$_5$: 496.2811. Observed m/z 496.2824.

Example 38 trans-3-($N^2$-(N-tert-Butoxycarbonylalanyl)-$N^1$-phenylethylhydrazinocarbonyl)-2-(2-phenylethyl)oxirane (Boc-Ala-AHph trans-EP-CH$_2$CH$_2$Ph). This compound was obtained using the EDC/HOBt coupling method and purified by chromatography on a silica gel column using 1:4 EtOAc:

$CH_2Cl_2$ as the eluting solvent system; white solid, yield 73%. $^1$H NMR ($CDCl_3$): 1.10 (d, 3H, Ala), 1.4 (2s, 9H), 1.6 (m, 2H, EP-$CH_2$), 2.7–2.9 (m, 4H, $CH_2Ph$), 3.1 (s, 1H, epoxide), 3.3 &3.4 (2s, 1H, epoxide), 3.6–3.8 (m, 2H, $NCH_2CH_2$), 4.1 (m, 1H, αH), 4.7–4.8 (s, 1H, NH), 7.1–7.4 (m, 10 H), 7.9 and 8.1 (s, 1H, NH). MS (FAB$^+$) 481 (M+1, 20%), 426 (M–tBu+1, 100%). HRMS (FAB) Calcd. for $C_{27}H_{36}N_3O_5$: 482.2655. Observed m/z 482.2676

Example 39 trans-3-($N^2$-Norvalyl)-$N^1$-phenylethylhydrazinocarbonyl)-1-(2-phenylethyl)oxirane Trifluoroacetate Salt (Nva-AHph-trans-EP-$CH_2CH_2Ph$.TFA). The blocked epoxysuccinyl peptide was dissolved in a small amount of TFA at 0° C. After 15 minutes, the excess TFA was removed under vacuum. The residue was purified by column chromatography and the product eluted with 1:49 MeOH:$CH_2Cl_2$; white solid, yield 48%. TLC $R_f$=0.6 (9:1 $CH_2Cl_2$:MeOH); $^1$H-NMR (DMSO-$d_6$): 0.7–0.9 (m, 3H), 1.2–1.4 (m, 2H), 1.6–1.8 (m, 2H), 2.6–2.8 (m, 4H), 2.9–3.0 (m, 1H), 3.6 (s, 1H), 4.0 (m, 1H), 7.1–7.4 (m, 10H), 8.1–8.2 (m, 1H); MS (FAB$^+$) m/z 392 (M–TFA+1, 100%); HRMS Calcd. for $C_{20}H_{30}N_3O_5$: 392.21855. Observed m/z 392.21611.

Example 40 trans-3-($N^2$-Norleucyl)-$N^1$-phenylethylhydrazinocarbonyl)oxirane-2-carboxylic Acid Ethyl Ester Trifluoroacetate Salt (Nle-AHph-trans-EP-COOEt-TFA). The blocked epoxysuccinyl peptide was dissolved in a small amount of TFA at 0° C. After 15 minutes, the excess TFA was removed under vacuum. The residue was purified by column chromatography and the product eluted with 1:49 MeOH:$CH_2Cl_2$; white solid, yield 52%; TLC $R_f$=0.5 (1:9 MeOH:$CH_2Cl_2$); $^1$H-NMR (DMSO-$d_6$): 0.8–1.0 (m, 3H), 1.2–1.3 (t, 3H), 1.3–1.4 (m, 4H), 1.6–1.8 (m, 2H), 2.7–2.9 (m, 2H), 3.6 (s, 1H), 3.8–4.0 (m, 2H), 4.1–4.2 (q, 2H), 7.1–7.4 (m, 5H), 8.2–8.4 (b, 2H); MS (FAB$^+$) m/z 392 (M–TFA+1, 100%); HRMS Calcd. for $C_{20}H_{30}N_3O_5$: 392.21855. Observed m/z 392.21611.

Example 41 trans-3-($N^2$-Alanyl)-$N^1$-phenylethylhydrazinocarbonyl)-2-(2-phenylethyl)oxirane Trifluoroacetate Salt (Ala-AHph-trans-EP-$CH_2CH_2Ph$.TFA). The blocked epoxysuccinyl peptide was dissolved in a small amount of TFA at 0° C. After 15 minutes, the excess TFA was removed under vacuum. The residue was purified by column chromatography and the product eluted with 1:9 MeOH:$CH_2Cl_2$; white solid, yield 85%. TLC $R_f$=0.58 (1:9 MeOH:$CH_2Cl_2$); $^1$H-NMR (DMSO-$d_6$): 0.8 (d, 3H, Ala), 1.6 (m, 2H, EP-$CH_2$), 2.7–2.9 (m, 4H, $CH_2Ph$), 3.1 (s, 1H, epoxide), 3.3 and 3.4 (2s, 1H, epoxide), 3.6–3.8 (m, 2H, $NCH_2CH_2$), 4.1 (m, 1H, α-H), 4.7–4.8 (s, 1H, NH), 7.1–7.4 (m, 10H), 8.1 (s, 1H, NH). MS (FAB$^+$) m/z 382 (M+1, 100%); HRMS Calcd. for $C_{22}H_{28}N_3O_3$: 382.2130. Observed m/z 382.2133.

Example 42 trans-3-($N^2$-Benzyl-$N^1$-benzyloxycarbonylhydrazinocarbonyl)oxirane-2-carboxylic Acid Ethyl Ester (Cbz-APhe-(trans)-EP-COOEt). This compound was obtained using the EDC/HOBt coupling method and purified by chromatography on a silica gel column using 1:4 EtOAc:$CH_2Cl_2$ as the eluting solvent system; white solid, yield 19%. $^1$H NMR ($CDCl_3$): 1.25 (t, 3H, $OCH_2CH_3$), 3.48 and 4.45 (d, 2H, epoxy), 3.95 (d 2H, $CH_2$-Ph) 4.30 (q, 2H, $OCH_2CH_3$), 5.10 (m, 1H, NH), 5.20 (m, 2H, Cbz). HRMS (FAB) Calcd. for $C_{21}H_{23}N_2O_6$: 399.1596. Observed m/z 399.1583. Anal. Calcd. for $C_{21}H_{22}N_2O_6$: C, 63.31; H, 5.57; N, 7.03. Found: C, 63.35; H, 5.71; N, 6.9.

Example 43 trans-3-($N^2$-Benzyl-$N^1$-benzyloxycarbonylhydrazinocarbonyl)-2-(2-phenylethyl)oxirane (Cbz-APhe-trans-EP-$CH_2CH_2Ph$). This compound was obtained using the EDC/HOBt coupling method and purified by chromatography on a silica gel column using 1:4 EtOAc:$CH_2Cl_2$ as the eluting solvent system; white solid, yield 22%. $^1$H NMR ($CDCl_3$): 1.85 (m, 2H, $CH_2CH_2Ph$), 2.80 (m, 2H EPCH$_2$), 3.00 and 4.10 (d, 2H, epoxy), 3.95 (d 2H, NHCH$_2$Ph), 5.10 (m, 1H, NH), 5.20 (m, 2H, Cbz). HRMS (FAB) Calcd. for $C_{26}H_{27}N_2O_4$: 431.1970. Observed m/z 431.1961.

Example 44

(2S,3S)-3-($N^2$-(N-Benzyloxycarbonylleucyl)-$N^1$-isobutylhydrazinocarbonyl)oxirane-2-carboxylic Acid Ethyl Ester (Cbz-Leu-ALeu-(2S,3S)-EP-COOEt). This compound was obtained using the EDC/HOBt coupling method and purified by chromatography on a silica gel column using 1:34:12 MeOH:$CH_2Cl_2$:EtOAc as the eluting solvent system; white solid, yield 45%. $^1$H NMR ($CDCl_3$): 0.95 (m, 6H, Leu), 1.25 (t, 3H, $OCH_2CH_3$), 1.45–1.90 (m, 3H, Leu), 3.20 and 3.55 (m, 2H, $NCH_2CH$), 3.60 and 3.80 (d, 2H, epoxy), 4.15–4.25 (m, 3H, $OCH_2CH_3$ and α-H), 5.10 (m, 2H, Cbz), 5.15 (m, 1H, NH), 7.16–7.37 (m, 5H, Ph), 8.80 (m, 1H, NH). HRMS (FAB) Calcd. for. $C_{24}H_{36}N_3O_7$: 478.2553. Observed m/z 478.2563. Anal. Calcd. for $C_{24}H_{35}N_5O_7$.0.65$H_2O$: C, 58.92H, 7.47; N, 8.58. Found: C, 59.43; H, 7.02; N, 8.11.

Example 45 trans-3-($N^2$-(N-Benzyloxycarbonylleucyl)-$N^1$-isobutylhydrazinocarbonyl)oxirane-2-carboxylic Acid Ethyl Ester (Cbz-Leu-ALeu-trans-EP-COOEt). This compound was obtained using the EDC/HOBt coupling method and purified by chromatography on a silica gel column using 1:34:12 MeOH:$CH_2Cl_2$:EtOAc as the eluting solvent system; white solid, yield 45%. $^1$H NMR ($CDCl_3$): 0.95 (m, 12H, Leu and ALeu), 1.25 (t, 3H, $OCH_2CH_3$), 1.45–1.90 (m, 4H, Leu and ALeu), 3.20 and 3.55 (m, 2H, $NCH_2CH$), 3.60 and 3.80 (d, 2H, epoxy), 4.15–4.25 (m, 3H, $OCH_2CH_3$ and α-H), 5.10 (m, 2H, Cbz), 5.15 (m, 1H, NH), 7.16–7.37 (m, 5H, Ph), 8.80 (m, 1H, NH). HRMS (FAB) Calcd. for $C_{24}H_{36}N_3O_7$: 478.2553. Observed m/z 478.2561.

Example 46 trans-3-($N^2$-(N-3-Benzyloxyphenylalanyl)-$N^1$-isobutylhydrazinocarbonyl)oxirane-2-carboxylic Acid Ethyl Ester (Cbz-Phe-ALeu-trans-EP-COOEt). This compound was obtained using the EDC/HOBt coupling method and purified by chromatography on a silica gel column using 1:1 EtOAc:$CH_2Cl_2$ as the eluting solvent system; white solid, yield 25%. $^1$H NMR ($CDCl_3$): 0.78 (m, 6H, Leu), 1.25 (m, 3H $OCH_2CH_3$), 1.45 (m, 1H, Leu), 2.9–3.1 (m, 2H, $NCH_2CH$), 3.60 and 3.83 (d, 2H, epoxy), 4.2 (m, 2H, $OCH_2CH_3$), 4.35 (m, 1H, α-H), 5.20 (m, 2H, Cbz), 7.16–7,26 (m, 5H, Ph), 8.4 (m, 1H, NH). HRMS (FAB) Calcd. for $C_{27}H_{34}N_3O_7$: 512.2396. Observed m/z 512.2394.

Example 47 trans-3-(N²-(N-3-Benzyloxyphenylalanyl)-N¹-isobutyl-hydrazinocarbonyl)-2-(2-phenylethyl)oxirane (Cbz-Phe-ALeu-trans-EP-CH₂CH₂Ph). This compound was obtained using the EDC/HOBt coupling method. It was purified by column chromatography using 1:19 MeOH:CH₂Cl₂ as an eluent, and was then rechromatographed using 1:4 EtOAc:CH₂Cl₂ as the eluent; white solid, yield 47%. $^1$H NMR (DMSO-d₆): 0.78 (m, 6H, Leu), 1.6–1.9(m, 3H, CHCH₂ and CH₂-EP) 2.62 (m, 2H, PhCH₂CH), 2.80 (m, 2H, PhCH₂CH₂-EP), 3.20 and 3.45 (m, 2H, NCH₂CH), 3.60 and 3.80 (m, 2H, epoxy), 4.2 (m, 1H, α-H) 5.20 (m, 2H, Cbz), 7.16–7.26 (m, 15H, Ph), 8.10 (m, 1H, NH). HRMS (FAB) Calcd. for $C_{30}H_{38}N_4O_7$: 544.2815. Observed m/z 544.2803. Anal. Calcd. for $C_{32}H_{37}N_3O_5.0.5H_2O$: C, 69.56; H, 6.88; N, 7.61. Found: C, 69.52; H, 6.82; N, 7.64.

Example 48 trans-3-(N²-(N-3-Benzyloxyphenylalanyl)-N¹-benzylhydrazinocarbonyl)-2-(2-phenylethyl)oxirane (Cbz-Phe-APhe-trans-EP-CH₂CH₂Ph). This compound was obtained using the EDC/HOBt coupling method. It was purified by column chromatography using 1:3 EtOAc:CH₂Cl₂ as an eluent, and was then rechromatographed using 1:2 EtOAc:CH₂Cl₂ as the eluent; recrystallized from ether/hexane; white solid, yield 36%. $^1$H NMR (CDCl₃). 1.7–1.9 (m, 2H, CH₂-EP), 2.50–2.60 (m, 2H, PhCH₂CH), 2.80–3.10 (m, 2H, PhCH₂CH₂-EP), 3.60 and 3.80 (m, 2H, epoxy), 4.0 (m, 2H, NHCH₂), 4.2 (m, 1H, α-H) 5.20 (m, 2H, Cbz), 7.16–7.26 (m, 20H, Ph), 8.10 (m, 1H, NH). HRMS (FAB) Calcd. for $C_{35}H_{36}N_3O_5$: 577.25762. Observed m/z 577.2541. Anal. Calcd. for $C_{35}H_{35}N_3O_5.0.65H_2O$: C, 71.32; H, 6.21; N, 7.13. Found: C, 71.74; H, 6.68; N, 6.73.

Example 49 trans-3-(N²-(N-Benzyloxycarbonylleucyl)-N¹-ethylhydrazinocarbonyl)oxirane-2-carboxylic Acid Ethyl Ester (Cbz-Leu-AAbu-trans-EP-COOEt). This compound was obtained using the EDC/HOBt coupling method and purified by chromatography on a silica gel column using 1:34:12 MeOH:CH₂Cl₂:EtOAc as the eluting solvent system; white solid, yield 62%. $^1$H NMR (CDCl₃): 0.93 (m, 6H, Leu), 1.15 (q, 3H, NHCH₂CH₃), 1.25 (t, 3H, OCH₂CH₃), 1.45–1.80 (m, 3H, Leu and AAbu), 3.56 (m, 2H, NCH₂CH₃), 3.60 and 3.85(d, 2H, epoxy), 4.15–4.25 (m, 3H, OCH₂CH₃ and α-H), 5.10 (m, 2H, Cbz), 5.30 (m, 1H, NH), 7.16–7.37 (m, 5H, Ph), 8.80 (m, 1H, NH). HRMS (FAB) Calcd. for $C_{22}H_{32}N_3O_7$: 450.2240. Observed m/z 450.2256. Anal. Calcd. for $C_{22}H_{31}N_3O_7.0.55H_2O$: C, 57.50; H, 7.04; N, 9.14. Found: C, 57.58; H, 6.98; N, 9.07.

Example 50 trans-3-(N-(N-Benzyloxycarbonylleucyl)-N¹-ethylhydrazinocarbonyl)oxirane-2-carboxylic Acid (Cbz-Leu-AAbu-trans-EP-COOH). This compound was obtained by saponification of the ethyl ester with KOH/EtOH; white solid, yield 63%. $^1$H NMR (CDCl₃): 0.93 (m, 6H, Leu), 1.15 (q, 3H NHCH₂CH₃), 1.45–1.80 (m, 3H, Leu and AAbu), 3.0 (d, 2H, epoxy), 3.56 (m, 2H, NCH₂CH₃), 4.25 (m, 1H, α-H), 5.10 (m, 2H, Cbz), 5.30(m, 1H, NH), 7.16–7.37 (m, 5H, Ph), 8.10 (m, 1H, NH). HRMS (FAB) Calcd. for $C_{20}H_{38}N_3O_7$: 422.1927. Observed m/z 422.1949.

Example 51

(2S,3S)-3-(N²-(N-Benzyloxycarbonylleucylleucyl)-N¹-isobutylhydrazinocarbonyl)oxirane-2-carboxylic Acid (Cbz-Leu-Leu-ALeu-(2S,3S)-EP-COOH). This compound was obtained by saponification of the ethyl ester with KOH/EtOH and recrystallized from ether/hexane; white solid, yield 37%. $^1$H NMR (CDCl₃): 0.90 (m, 18H, Leu), 1.21 (t, 3H, OCH₂CH₃), 1.40–1.90 (m, 7H, Leu), 3.20–3.45 (m, 2H, ALeu), 3.60 and 3.70 (d, 2H, epoxy), 4.15 (m, 1H, α-H), 4.45 (m, 1H, α-H) 5.20 (m, 2H, Cbz), 5.30 (m, 1H, NH), 6.41 (m, 1H, NH), 7.16–7.37 (m, 5H, Ph), 9.00 (m, 1H, NH). HRMS (FAB) Calcd. for $C_{28}H_{43}N_4O_8$: 563.3080. Observed m/z 563.3074.

Example 52

(2S,3S)-3-(N²-(N-Benzyloxycarbonylglutamylvalyl)-N¹-carboxymethylhydrazinocarbonyl)oxirane-2-carboxylic Acid Ethyl Ester (Cbz-Glu-Val-AAsp-(2S,3S)-EP-COOEt). This compound was obtained using the mixed anhydride coupling method and the t-butyl esters were deblocked using the procedure previously described. $^1$H NMR (DMSO-d₆): 0.84 (d, 6H, Val), 1.20, 1.21 (t, 3H, OCH₂CH₃), 1.7–2.1 (m, 3H, Val, Glu), 2.21 (m, 2H, Glu), 3.60 and 4.10 (d, 2H, epoxy), 3.09–4.20 (m, 4H, NCH₂COOH, and OCH₂CH₃), 4.20–4.40 (m, 2H, α-H), 5.05 (m, 2H, Cbz), 7.20–7.40 (m, 5H, Ph), 8.00 (m, 1H, NH), 11.00 (m, COOH). HRMS (FAB) Calcd. for $C_{26}H_{35}N_4O_{12}$: 595.2251. Observed m/z 5952268. Anal. Calcd. for $C_{26}H_{35}N_4O_{12}.0.5H_2O$: C, 51.74; H, 5.84; N, 9.28. Found: C, 51.70; H, 5.80; N, 9.17.

Example 53 trans-2-(N²-(N-Benzyloxycarbonylalanylalanyl)-N¹-carbamoylmethylhydrazinocarbonyl)-3-(4-chlorophenyl)oxirane (Cbz-Ala-Ala-AAsn-trans-EP-Ph-4-Cl) was obtained using the EDC/HOBt coupling method, purified by column chromatography on silica gel using 1:9 MeOH:CH₂Cl₂ as the eluent, and then recrystallized from EtOAc/CH₂Cl₂; white powder, yield 50%. $^1$H NMR(DMSO-d₆): 1.02–1.03 (d, 3H, CH₃), 1.14–1.18 (d, 3H, CH₃), 3.29–3.31 (d, 2H, NCH₂CO), 3.94–4.16 (m, 4H, epoxy and 2×α-H), 4.99 (m, 2H, Cbz), 7.20 (s, 1H, NH), 7.32 (m, 9H, Ph and Ph-Cl), 8.07–8.09 (d, 1H, NH), 10.64 (s, 1H, NH). HRMS (ESI) Calcd. for $C_{25}H_{29}N_5O_7Cl$ : 546.1758. Observed m/z 546.175551. Anal. Calcd. for $C_{25}H_{28}N_5O_7Cl.0.2H_2O$: C, 54.63; H, 5.21; N, 12.74. Found: C, 54.65; H, 5.25; N, 12.47.

Example 54 trans-3-(N²-(N-Benzyloxycarbonylalanylalanyl)-N¹-carbamoylmethylhydrazinocarbonyl)-2-(2-phenethyl)oxirane (Cbz-Ala-Ala-AAsn-trans-EP-CH₂CH₂Ph) was obtained using the EDC/HOBt coupling method, purified by column chromatography on silica gel using 1:9 MeOH:CH₂Cl₂ as the eluent, and then recrystallized from EtOAc/hexane; white powder, yield 40%. $^1$H NMR (DMSO-d₆): 1.15–1.17 (d, 3H, CH₃), 1.23–1.25 (d, 3H, CH₃), 1.67 (m, 2H, CH₂CH₂Ph), 2.65 (m, 2H, CH₂CH₂Ph), 2.86 (m, 1H, epoxy), 3.28–3.31 (d, 2H, NCH₂CO), 3.63 (s, 1H, epoxy), 4.01 (m, 1H, α-H), 4.24 (m, 1H, α-H), 4.99 (m, 2H, Cbz), 7.13 (s, 1H, NH), 7.17–7.41 (m, 10H, 2×Ph), 7.48 (s, 1H, NH), 8.17 (d, 1H, NH), 10.67 (s, 1H, NH). MS (ESI) m/z 540 [(M+1)⁺]. HRMS (ESI) Calcd. for $C_{27}H_{34}N_5O_7$: 540.2392. Observed m/z 540.2458. Anal. Calcd. for $C_{27}H_{33}N_5O_7.0.2H_2O$: C, 59.70; H, 6.20; N, 12.89. Found: C, 59.46; H, 6.15; N, 12.76.

Example 55

(2S,3S)-2-(Dibutylcarbamoyl)-3-(N²-(N-benzyloxycarbonylalanylalanyl)-N¹-carbamoylmethylhydrazinocarbonyl)oxirane (Cbz-Ala-Ala-AAsn-(2S,3S)-EP-CON(nBu)$_2$) was obtained using the EDC/HOBt coupling method, purified by column chromatography on silica gel using 1:9 MeOH:CH$_2$Cl$_2$ as the eluent, and then recrystallized from EtOAc/hexane; white powder, yield 26%. $^1$H NMR (DMSO-d$_6$): 0.84–0.90 (m, 6H, 2×NCH$_2$CH$_2$CH$_2$CH$_3$), 1.17–1.27 (m, 10H, 2×Ala-CH$_3$ and 2×NCH$_2$CH$_2$CH$_2$CH$_3$), 1.41 (t, 2H, NCH$_2$CH$_2$CH$_2$CH$_3$), 1.51 (t, 2H, NCH$_2$CH$_2$CH$_2$CH$_3$), 3.20–3.32 (m, 7H, NCH$_2$CO and CH$_2$NCH$_2$ and epoxy), 3.63 (s, 1H, epoxy), 4.04 (m, 1H, α-H), 4.26 (m, 1H, α-H), 4.99 (m, 2H, Cbz), 7.21 (s, 1H, NH), 7.33 (m, 5H, Ph), 7.49 (s, 1H, NH), 8.15 (d, 1H, NH), 10.62 (s, 1H, NH). MS (ESI) m/z 591 [(M+1)$^+$]. HRMS (ESI) Calcd. for C$_{28}$H$_{43}$N$_6$O$_8$: 591.3059. Observed m/z 591.314238. Anal. Calcd. for C$_{28}$H$_{42}$N$_6$O$_8$.1H$_2$O: C, 55.25; H, 7.29; N, 13.81. Found: C, 55.32; H, 7.10; N, 13.80.

Example 56

(2S,3S)-3-(N²-N-Benzyloxycarbonylalanylalanyl)-N¹-carbamoylmethylhydrazinocarbonyl)oxirane-2-carboxylic Acid Phenethyl Ester (Cbz-Ala-Ala-AAsn-(2S,3S)-EP-COOCH$_2$CH$_2$Ph) was obtained using the EDC/HOBt coupling method, purified by column chromatography on silica gel using 1:9 MeOH:CH$_2$Cl$_2$ as the eluent, and then recrystallized from EtOAc/hexane; white powder, yield 9%. $^1$H NMR ((CD$_3$)$_2$CO): 1.34 (m, 6H, 2×Ala-CH$_3$), 2.87 (s, 2H, NCH$_2$CO), 2.98 (t, 2H, CH$_2$Ph), 3.48 (s, 1H, epoxy), 4.04 (m, 1H, α-H), 4.17 (m, 1H, α-H), 4.28–4.43 (m, 3H, CH$_2$CH$_2$Ph and epoxy), 5.10 (m, 2H, Cbz), 6.57 (s, 1H, NH), 6.65 (s, 1H, NH), 7.19–7.38 (m, 10H, 2×Ph), 7.77 (s, 1H, NH), 9.89 (s, 1H, NH). MS (ESI) m/z 584 [(M+1)$^+$]. HRMS (ESI) Calcd. for C$_{28}$H$_{34}$N$_5$O$_9$: 584.233. Observed n/z 584.235653. Anal. Calcd. for C$_{28}$H$_{33}$N$_5$O$_9$.0.1H$_{200.5}$EtOAc: C, 57.18; H, 6.06; N, 11.11. Found: C, 56.96; H, 5.88; N, 11.08.

Example 57

(2S,3S)-2-(N-Methyl-N-benzylcarbamoyl)-3-(N²-(N-benzyloxycarbonylalanylalanyl)-N¹-carbamoylmethylhydrazinocarbonyl)oxirane (Cbz-Ala-Ala-AAsn-(2S,3S)-EP-CON(CH$_3$)Bzl) was obtained using the EDC/HOBt coupling method, purified by column chromatography on silica gel using 1:9 MeOH:CH$_2$Cl$_2$ as the eluent, and then recrystallized from EtOAc/hexane; white powder, yield 10%. $^1$H NMR (DMSO-d$_6$): 1.11–1.27 (m, 6H, 2×Ala-CH$_3$), 2.95 (d, 3H, N—CH$_3$), 3.20–3.32 (d, 3H, NCH$_2$CO and epoxy), 3.34 (s, 1H, epoxy), 4.04–4.61 (m, 4H, 2×α-H, CH$_2$Ph), 5.02 (m, 2H, Cbz), 7.21 (s, 1H, NH), 7.33 (m, 5H, Ph), 7.42 (d, 1H, NH), 8.20 (d, 1H, NH), 10.73 (s, 1H, NH). MS (ESI) m/z 583 [(M+1)$^+$]. HRMS (ESI) Calcd. for C$_{28}$H$_{35}$N$_6$O$_8$: 583.2567. Observed m/z 583.251638. Anal. Calcd. for C$_{28}$H$_{34}$N$_6$O$_8$.1.3H$_2$O: C, 55.49; H, 6.09; N, 13.87. Found: C, 55.45; H, 5.89; N, 13.85.

Example 58

(2S,3S)-2-(2-Phenethylcarbamoyl)-3-(N²-(N-benzyloxycarbonylalanylalanyl)-N¹-carbamoylmethylhydrazinocarbonyl)oxirane (Cbz-Ala-Ala-AAsn-(2S,3S)-EP-CONHCH$_2$CH$_2$Ph) was obtained using the EDC/HOBt coupling method, purified by chromatography on a silica gel column using 1:13 MeOH:CH$_2$Cl$_2$ as the eluent, rechromatographed using 1:19 MeOH:CH$_2$Cl$_2$ as the eluent, and then recrystallized from EtOAc/hexane; white solid, yield 8%. HRMS (FAB) Calcd. for C$_{28}$H$_{35}$N$_6$O$_8$: 583.25164. Observed m/z 583.25393. $^1$H NMR (DMSO-d$_6$): 1.1–1.3 (m, 6H, CH$_3$), 2.7–2.8 (m, 2H, NHCH$_2$CH$_2$Ph), 3.2–3.4 (m, 2H, NHCH$_2$CH$_2$Ph), 3.8–4.0 (d, 1H, epoxy), 4.0–4.1 (m, 3H, epoxy and NCH$_2$CO), 4.35–4.5 (m, 2H, α-H), 4.9–5.1 (m, 3H, NH and OCH$_2$Ph), 6.5 (d, 1H, NH), 7.1–7.4 (m, 11H, NH and Ph), 8.05 (m, 1H, NH), 8.1 (m, 1H, NH). Anal. Calcd. for C$_{28}$H$_{34}$N$_6$O$_8$.0.75H$_2$O: C, 56.42; H, 5.96; N, 14.10. Found: C, 56.81; H, 5.92; N, 13.66.

Example 59

(2R,3R)-2-(1-Benzylcarbamoylethylcarbamoyl)-3-(N²-(N-benzyloxycarbonylalanylalanyl)-N¹-carbamoylmethylhydrazinocarbonyl)oxirane (Cbz-Ala-Ala-AAsn-(2R,3R)-EP-CO-Ala-NHBzl) was obtained using the EDC/HOBt coupling method, purified by chromatography on a silica gel column using 1:13 MeOH:CH$_2$Cl$_2$ as the eluent, rechromatographed using 1:7 MeOH:CH$_2$Cl$_2$ as the eluent, and then recrystallized from EtOAc/hexane; white solid, yield 4%. HRMS (FAB)Calcd. for C$_{30}$H$_{38}$N$_7$O$_9$:640.273101. Observed m/z 640.2717. $^1$H NMR (DMSO-d$_6$): 1.1–1.4 (m, 9H, CH$_3$), 3.9–4.2 (m, 4H, epoxy and NCH$_2$CO), 4.2–4.4 (m, 4H, α-H and NCH$_2$Ph), 4.45 (m, 1H, α-H), 4.9–5.05 (m, 2H, OCH$_2$Ph), 5.05 (s, 1H, NH), 6.7 (m, 1H, NH), 7.15–7.5 (m, 10H, Ph), 8.1–8.2 (m, 2H, NH), 8.45 (m, 1H, NH). Anal. Calcd. for C$_{30}$H$_{37}$N$_7$O$_9$.EtOAc: C, 56.12; H, 6.19; N, 13.48. Found: C, 56.19; H, 6.21; N, 13.56.

Example 60

(2S,3S)-2-(2-Benzylcarbamoyl)-3-(N²-(N-benzyloxycarbonylalanylalanyl)-N¹-carbamoylmethylhydrazinocarbonyl)oxirane (Cbz-Ala-Ala-AAsn-(2S,3S)-EP-CONHCH$_2$Ph) was obtained using the EDC/HOBt coupling method, purified by chromatography on a silica gel column using 1:13 MeOH:CH$_2$Cl$_2$ as the eluent, and then recrystallized from EtOAc/hexane; white solid, yield 15%. MS (ESI) m/z 569 [(M+1)$^+$]. $^1$H NMR (DMSO-d$_6$): 1.15–1.25 (m, 6H, CH$_3$), 3.9 (m, 1H, epoxy), 4.0–4.1 (m, 3H, epoxy and NCH$_2$CO), 4.2–4.3 and 4.3–4.5 (m, 3H, α-H and NCH$_2$Ph), 4.5 (m, 1H, α-H), 4.9–5.05 (m, 2H, OCH$_2$Ph), 5.05 (s, 1H, NH), 6.5 (d, 1H, NH), 7.15–7.3 (m, 11H, NH and Ph), 8.05 (m, 1H, NH), 8.5 (m, 1H, NH). Anal. Calcd. for C$_{27}$H$_{32}$N$_6$O$_8$: C, 57.04; H, 5.67; N, 14.78. Found: C, 57.11; H, 5.83; N, 14.52.

Example 61

(2S,3S)-3-(N²-(N-Benzyloxycarbonylalanylalanyl)-N¹-carbamoylmethylhydrazinocarbonyl)oxirane-2-carboxylic Acid Benzyl Ester (Cbz-Ala-Ala-AAsn-(2S,3S)-EP-COOBzl) was obtained using the EDC/HOBt coupling method, purified by chromatography on a silica gel column using 1:13 MeOH:CH$_2$Cl$_2$ as the eluent, and then recrystallized from EtOAc/hexane; white solid, yield 15%. HRMS (FAB) Calcd. for C$_{27}$H$_{32}$N$_5$O$_9$: 570.22000. Observed m/z 570.21949. $^1$H NMR(DMSO-d$_6$): 1.1–1.3 (m, 6H, CH$_3$), 3.25–3.4 and 3.5–3.7 (m, 3H, epoxy and NCH$_2$CO), 4.05 (m, 2H, epoxy and α-H), 4.2 (m, 1H, α-H), 4.95 and 5.2 (m, 4H, OCH$_2$Ph), 7.2–7.5 (m, 11H, NH and Ph), 7.5 (s, 1H, NH), 8.15 (m, 1H, NH). Anal. Calcd. for C$_{27}$H$_{31}$N$_5$O$_9$.H$_2$O: C, 55.20; H, 5.62; N, 11.92. Found: C, 55.55; H, 5.61; N, 11.49.

Example 62 trans-2-($N^2$-(N-Benzyloxycarbonylvalyl)-$N^1$-carboxymethylhydrazinocarbonyl)-3-(4-chlorophenyl)oxirane (Cbz-Val-AAsp-trans-EP-Ph-4-Cl). $^1$H NMR (DMSO-$d_6$): 0.75–0.88 (d, 6H, Val), 1.80 (m, 1H, Val), 3.58 (s, 1H, epoxy), 4.11 (s, 1H, NHCH$_2$COOH), 4.35 (s, 1H, α-H), 5.02 (s, 2H, Cbz), 6.18 (d, 1H, NH), 7.15–7.53(m, 9H, Ph), 7.92 (d, 1H, NH). HRMS (ESI) Calcd. for $C_{24}H_{26}N_3O_7Cl$: 503.1543. Observed m/z 503.1537. Anal. Calcd. for $C_{24}H_{26}N_3O_7Cl \cdot 1.5H_2O$: C, 54.29; H, 4.93; N, 7.91. Found: C, 54.12; H, 5.00; N, 7.68.

Example 63

(2S,3S)-3-($N^2$-(3-Phenylpropanoylvalylalanyl)-$N^1$-carboxymethylhydrazinocarbonyl)oxirane-2-carboxylic Acid Ethyl Ester (PhPr-Val-Ala-AAsp-(2S,3S)-EP-COOEt). $^1$H NMR (DMSO-$d_6$): 0.75 (m, 6H, Val CH$_3$), 1.17 (m, 6H, Ala CH$_3$ and OEt), 1.85 (m, 1H, Val CH), 2.42 (m, 2H, PhCH$_2$), 2.76 (t, 2H, PhCH$_2$CH$_2$CO), 3.32 (s, 2H, AAsp CH$_2$COOH), 3.59 (d, 2H, epoxy), 4.15 (m, 4H, α-H and OEt), 7.16–7.24 (m, 6H, Ph and NH), 7.80 (m, 1H, NH), 8.15 (d, 1H, NH), 10.85 (s, 1H, COOH). HRMS (FAB) Calcd. for $C_{25}H_{35}N_4O_9$: 535.24040. Observed m/z 535.24220. Anal. Calcd. for $C_{25}H_{34}N_4O_9$: C, 56.17; H, 6.41; N, 10.48. Found: C, 55.90; H, 6.12; N, 10.16.

Example 64

(2R,3R)-3-$N^2$-(3-Phenylpropanoylvalylalanyl)-$N^1$-carboxymethylhydrazinocarbonyl)oxirane-2-carboxylic Acid Ethyl Ester (PhPr-Val-Ala-AAsp-(2R,3R)-EP-COOEt). $^1$H NMR (DMSO-$d_6$): 0.77 (m, 6H, Val CH$_3$), 1.19 (m, 6H, Ala CH$_3$ and OEt), 1.87 (m, 1H, Val CH), 2.42 (m, 2H, PhCH$_2$), 2.76 (m, 2H, PhCH$_2$CH$_2$CO), 3.32 (s, 2H, AAsp CH$_2$COOH), 3.45 (s, 2H, epoxy), 4.15 (m, 4H, α-H and OEt), 7.11–7.24 (m, 6H, Ph and NH), 7.84 (m, 1H, NH), 8.26 (d, 1H, NH), 10.85 (s, 1H, COOH). HRMS (FAB) Calcd. for $C_{25}H_{35}N_4O_9$: 535.24040. Observed m/z 535.24153. Anal. Calcd. for $C_{25}H_{34}N_4O_9 \cdot 0.5H_2O$ C., 55.25; H, 6.44; N, 10.31. Found: C, 55.04; H, 6.36; N, 10.26.

Example 65

(2S,3S)-3-$N^2$-(3-Phenylpropanoylvalylalanyl)-$N^1$-carboxymethylhydrazinocarbonyl)oxirane-2-carboxylic Acid Benzyl Ester (PhPr-Val-Ala-AAsp-(2S,3S)-EP-COOCH$_2$Ph). $^1$H NMR (DMSO-$d_6$): 0.77 (m, 6H, Val CH$_3$), 1.13 (m, 3H, Ala CH$_3$), 1.87 (m, 1H, Val CH), 2.42 (m, 2H, PhCH$_2$), 2.77 (m, 2H, PhCH$_2$CH$_2$CO), 3.32 (s, 2H, AAsp CH$_2$COOH), 3.61 (d, 2H, epoxy), 4.15 (m, 2H, α-H), 5.17 (m, 2H, Benzyl), 7.15–7.37 (m, 11H, Ph and NH), 7.80 (m, 1H, NH), 8.15 (m, 1H, NH), 10.90 (s, 1H, COOH). HRMS (FAB) Calcd. for $C_{30}H_{37}N_4O_9$: 597.25605. Observed m/z 597.26012. Anal. Calcd. for $C_{30}H_{36}N_4O_9 \cdot 0.5H_2O$: C, 59.49; H, 6.17; N, 9.25. Found: C, 58.68; H, 6.03; N, 9.54.

Example 66

(2R,3R)-3-($N^2$-(3-Phenylpropanoylvalylalanyl)-$N^1$-carboxymethylhydrazinocarbonyl)oxirane-2-carboxylic Acid Benzyl Ester (PhPr-Val-Ala-AAsp-(2R,3R)-EP-COOCH$_2$Ph). $^1$H NMR (DMSO-$d_6$): 0.77 (m, 6H, Val CH$_3$), 1.13 (m, 3H, Ala CH$_3$), 1.87 (m, 1H, Val CH), 2.42 (m, 2H, PhCH$_2$), 2.77 (t, 2H, PhCH$_2$CH$_2$CO), 3.32 (s, 2H, AAsp CH$_2$COOH), 3.61 (d, 2H, epoxy), 4.15 (m, 2H, α-H), 5.17 (m, 2H, Benzyl), 7.15–7.37 (m, 11H, Ph and NH), 7.84 (m, 1H, NH), 8.24 (m, 1H, NH), 10.90 (b, 1H, COOH). HRMS (FAB) Calcd. for $C_{30}H_{37}N_4O_9$: 597.25605. Observed m/z 597.25875. Anal. Calcd. for $C_{30}H_{36}N_4O_9 \cdot 0.5H_2O$: C, 59.49; H, 6.17; N, 9.25. Found: C, 58.75; H, 6.00; N, 9.47.

Example 67

(2S,3S)-3-($N^2$-(3-Phenylpropanoylvalylalanyl)-$N^1$-carboxymethylhydrazinocarbonyl)oxirane-2-carboxylic Acid Phenethyl Ester (PhPr-Val-Ala-AAsp-(2S,3S)-EP-COOCH$_2$CH$_2$Ph). $^1$H NMR (DMSO-$d_6$): 0.77 (m, 6H, Val CH$_3$), 1.18 (m, 3H, Ala CH$_3$), 1.86 (m, 1H, Val CH), 2.41 (m, 2H, PhCH$_2$), 2.76 (t, 2H, PhCH$_2$CH$_2$CO), 2.90 (t, 2H, PhCH$_2$), 3.32 (s, 2H, AAsp CH$_2$COOH), 3.53 and 3.69 (d, 2H, epoxy), 4.16 (m, 2H, α-H), 4.27 (m, 2H, OCH$_2$), 7.12–7.30 (m, 11H, Ph and NH), 7.80 (m, 1H, NH), 8.24 (d, 1H, NH), 10.85 (s, 1H, COOH). HRMS (FAB) Calcd. for $C_{31}H_{39}N_4O_9$: 611.27170. Observed m/z 611.27640. Anal. Calcd. for $C_{31}H_{38}N_4O_9 \cdot H_2O$: C, 59.23; H, 6.41; N, 8.91. Found: C, 59.19; H, 6.25; N, 9.26.

Example 68

(2S,3S)-2-(2-Ethylcarbamoyl)-3-($N^2$-(3-phenylpropanoylvalylalanyl)-$N^1$-carboxymethylhydrazinocarbonyl)oxirane (PhPr-Val-Ala-AAsp-(2S,3S)-EP-CONHCH$_2$CH$_3$). $^1$H NMR (DMSO-$d_6$): 0.76 (m, 6H, Val CH$_3$), 1.02 (t, 3H, CH$_3$), 1.19 (d, 3H, Ala CH$_3$), 1.90 (m, 1H, Val CH), 2.45 (m, 2H, PhCH$_2$), 2.77 (t, 2H, PhCH$_2$CH$_2$CO), 3.09 (m, 2H, CH$_2$N), 3.37 (s, 2H, AAsp CH$_2$COOH), 3.41 (s, 2H, epoxy), 4.17 (m, 2H, α-H), 7.11–7.25 (m, 6H, Ph and NH), 7.82 (d, 1H, NH), 8.23 (s, 1H, NH), 8.36 (t, 1H, NH), 10.85 (s, 1H, COOH). HRMS (FAB) Calcd. for $C_{25}H_{36}N_5O_8$: 534.2564. Observed m/z 534.2535. Anal. Calcd. for $C_{25}H_{35}N_5O_8 \cdot H_2O$: C, 54.44; H, 6.76; N, 12.70. Found: C, 54.53; H, 6.65; N, 12.90.

Example 69

(2S,3S)-2-(2-Benzylcarbamoyl)-3-($N^2$-(3-phenylpropanoylvalylalanyl)-$N^1$-carboxymethylhydrazinocarbonyl)oxirane (PhPr-Val-Ala-AAsp-(2S,3S)-EP-CONHBzl). $^1$H NMR (DMSO-$d_6$): 0.75 (m, 6H, Val CH$_3$), 1.13 (m, 3H, Ala CH$_3$), 1.87 (m, 1H, Val CH), 2.43 (m, 2H, PhCH$_2$), 2.77 (m, 2H, PhCH$_2$CH$_2$CO), 3.37 (m, 2H, AAsp CH$_2$COOH), 3.50 (s, 2H, epoxy), 4.15 (m, 2H, α-H), 4.31 (t, 2H, PhCH$_2$N), 7.13–7.31 (m, 11H, Ph and NH), 7.83 (m, 1H, NH), 8.10 (m, 1H, NH), 8.91 (t, 1H, NH), 10.85 (s, 1H, COOH). HRMS (FAB) Calcd. for $C_{30}H_{38}N_5O_8$: 596.27204. Observed m/z 596.27178. Anal. Calcd. for $C_{30}H_{37}N_5O_8 \cdot 0.7H_2O$: C, 59.22; H, 6.37; N, 11.52. Found: C, 59.20; H, 6.18; N, 11.52.

Example 70

(2R,3R)-2-(2-Benzylcarbamoyl)-3-($N^2$-(3-phenylpropanoylvalylalanyl)-$N^1$-carboxymethylhydrazinocarbonyl)oxirane (PhPr-Val-Ala-AAsp-(2R,3R)-EP-CONHBzl). $^1$H NMR (DMSO-$d_6$): 0.75 (m, 6H, Val CH$_3$), 1.13 (m, 3H, Ala CH$_3$), 1.87 (m, 1H, Val CH), 2.42 (m, 2H, PhCH$_2$), 2.77 (m, 2H, PhCH$_2$CH$_2$CO), 3.37 (m, 2H, AAsp CH$_2$COOH), 3.55 (d, 2H, epoxy), 4.15 (m, 2H, α-H), 4.28 (t, 2H, PhCH$_2$N), 7.14–7.30 (m, 11H, Ph and NH), 7.85 (m, 1H, NH), 8.24 (m, 1H, NH), 8.90 (t, 1H, NH), 10.94 (s, 1H, COOH). HRMS (FAB) Calcd. for $C_{30}H_{38}N_5O_8$: 596.27204. Observed m/z 596.27030. Anal. Calcd. for $C_{30}H_{37}N_5O_8 \cdot H_2O$: C, 58.72; H, 6.41; N, 11.41. Found: C, 58.42; H, 6.05; N, 11.62.

Example 71

(2S,3S)-2-(2-Phenethylcarbamoyl)-3-(N²-(3-phenylpropanoylvalylalanyl)-N¹-carboxymethylhydrazinocarbonyl)oxirane (PhPr-Val-Ala-AAsp-(2S,3S)-EP-CONHCH₂CH₂Ph). $^1$H NMR (DMSO-d$_6$): 0.75 (m, 6H, Val CH₃), 1.18 (m, 3H, Ala CH₃), 1.88 (m, 1H, Val CH), 2.43 (m, 2H, PhCH₂), 2.47–2.80 (m, 4H, PhCH₂CH₂CO and PhCH₂CH₂N), 3.32 (m, 4H, NCH₂CH₂Ph and AAsp CH₂COOH), 3.43 (s, 2H, epoxy), 4.16 (m, 2H, α-H), 7.13–7.31 (m, 11H, Ph and NH), 7.82 (m, 1H, NH), 8.25 (m, 1H, NH), 8.48 (t, 1H, NH), 10.85 (s, 1H, COOH). HRMS (FAB) Calcd. for $C_{31}H_{40}N_5O_8$: 610.28769. Observed m/z 610.28714. Anal. Calcd. for $C_{31}H_{39}N_5O_8 \cdot 0.8H_2O$: C, 59.65; H, 6.57; N, 11.22. Found: C, 59.59; H, 6.42; N, 11.26.

Example 72

(2R,3R)-2-(2-Phenethylcarbamoyl)-3-(N²-(3-phenylpropanoylvalylalanyl)-N¹-carboxymethylhydrazinocarbonyl)oxirane (PhPr-Val-Ala-AAsp-(2R,3R)-EP-CONHCH₂CH₂Ph). $^1$H NMR (DMSO-d$_6$): 0.75 (m, 6H, Val CH₃), 1.12 (m, 3H, Ala CH₃), 1.86 (m, 1H, Val CH), 2.40 (m, 2H, PhCH₂), 2.76 (m, 4H, PhCH₂CH₂CO and PhCH₂CH₂N)), 3.33 (m, 4H, NCH₂CH₂Ph and AAsp CH₂COOH), 3.67(s, 2H, epoxy), 4.15 (m, 2H, α-H), 7.13–7.31 (m, 11H, Ph and NH), 7.83 (m, 1H, NH), 8.15 (m, 1H, NH), 8.24 (t, 1H, NH), 10.93 (s, 1H, COOH). HRMS (FAB) Calcd. for $C_{31}H_{40}N_5O_8$: 610.28769. Observed m/z 610.29073. Anal. Calcd. for $C_{31}H_{39}N_5O_8$: C, 59.32 H, 6.58; N, 11.16. Found: C, 59.49; H, 6.45; N, 11.59.

Example 73

(2S,3S)-2-(2-Hydroxy-2-phenylethylcarbamoyl)-3-(N²-(3-phenylpropanoylvalylalanyl)-N¹-carboxymethylhydrazinocarbonyl)oxirane (PhPr-Val-Ala-AAsp-(2S,3S)-EP-CONHCH₂CH(OH)Ph). $^1$H NMR (DMSO-d$_6$): 0.76 (m, 6H, Val CH₃), 1.18 (m, 3H, Ala CH₃), 1.85 (m, 1H, Val CH), 2.43 (m, 2H, PhCH₂), 2.77 (m, 2H, PhCH₂CH₂), 3.37 (m, 4H, NCH₂ and AAsp CH₂COOH), 3.53 (s, 2H, epoxy), 4.16 (m, 2H, α-H), 4.60 (b, 1H, CH), 7.14–7.39 (m, 11H, Ph and NH), 7.80 (m, 1H, NH), 8.20 (m, 1H, NH), 8.50 (t, 1H, NH), 10.90 (s, 1H, COOH). HRMS (FAB) Calcd. for $C_{31}H_{40}N_5O_9$: 626.28260. Observed m/z 626.28608. Anal. Calcd. for $C_{31}H_{39}N_5O_9 \cdot H_2O$: C, 57.84; H, 6.42; N, 10.88. Found: C, 58.03; H, 6.35; N, 10.65.

Example 74

(2R,3R)-2-(2-Hydroxy-2-phenylethylcarbamoyl)-3-(N²-(3-phenylpropanoylvalylalanyl)-N¹-carboxymethylhydrazinocarbonyl)oxirane (PhPr-Val-Ala-AAsp-(2R,3R)-EP-CONHCH₂CH(OH)Ph). $^1$H NMR (DMSO-d$_6$): 0.77 (m, 6H, Val CH₃), 1.17 (m, 3H, Ala CH₃), 1.85 (m, 1H, Val CH), 2.43 (m, 2H, PhCH₂), 2.77 (m, 2H, PhCH₂CH₂), 3.32 (m, 4H, NCH₂ and AAsp CH₂COOH), 3.40 (s, 2H, epoxy), 4.16 (m, 2H, α-H), 4.60 (b, 1H, CH), 7.13–7.39 (m, 11H, Ph and NH), 7.80 (m, 1H, NH), 8.21 (m, 1H, NH), 8.50 (t, 1H, NH), 10.90 (s, 1H, COOH). HRMS (FAB) Calcd. for $C_{31}H_{40}N_5O_9$: 626.28260. Observed m/z 626.28250. Anal. Calcd. for $C_{31}H_{39}N_5O_9 \cdot H_2O$: C, 57.84; H, 6.42; N, 10.88. Found: C, 57.92; H, 6.40; N, 10.76.

Example 75

(2S,3S)-2-(1-Benzylcarbamoylethylcarbamoyl)-3-(N²-(3-phenylpropanoylvalylalanyl)-N¹-carboxymethylhydrazinocarbonyl)oxirane (PhPr-Val-Ala-AAsp-(2S,3S)-EP-CO-Ala-NHBzl). $^1$H NMR (DMSO-d$_6$): 0.76 (m, 6H, Val CH₃), 1.16 (d, 3H, Ala CH₃), 1.26 (d, 3H, Ala CH₃), 1.88 (m, 1H, Val CH), 2.43 (m, 2H, PhCH₂), 2.78 (t, 2H, PhCH₂CH₂CO), 3.33 (d, 2H, AAsp CH₂COOH), 3.60 (s, 2H, epoxy), 4.15 (m, 3H, α-H), 4.27 (d, 2H, PhCH₂N), 7.13–7.30 (m, 11H, Ph and NH), 7.80 (d, 1H, NH), 8.25 (d, 1H, NH), 8.45 (s, 1H, NH), 8.70 (b, 1H, NH), 10.85 (s, 1H, COOH). HRMS (FAB) Calcd. for $C_{33}H_{43}N_6O_9$: 667.30915. Observed m/z 667.31344. Anal. Calcd. for $C_{33}H_{42}N_6O_9 \cdot 0.5H_2O$: C, 58.67; H, 6.37; N, 12.44. Found: C, 58.11; H, 6.31; N, 12.30.

Example 76

(2R,3R)-2-(1-Benzylcarbamoylethylcarbamoyl)-3-(N²-(3-phenylpropanoylvalylalanyl)-N¹-carboxymethylhydrazinocarbonyl)oxirane (PhPr-Val-Ala-AAsp-(2R,3R)-EP-CO-Ala-NHBzl). $^1$H NMR (DMSO-d$_6$): 0.77 (m, 6H, Val CH₃), 1.13 (m, 3H, Ala CH₃), 1.25 (d, 3H, Ala CH₃), 1.88 (m, 1H, Val CH), 2.43 (m, 2H, PhCH₂), 2.78 (m, 2H, PhCH₂CH₂CO), 3.36 (d, 2H, AAsp CH₂COOH), 3.50 (s, 2H, epoxy), 4.15 (m, 3H, α-H),), 4.26 (m, 2H, PhCH₂N), 7.13–7.30 (m, 11H, Ph and NH), 7.85 (d, 1H, NH), 8.25 (d, 1H, NH), 8.45 (s, 1H, NH), 8.70 (b, 1H, NH), 10.93 (s, 1H, COOH). HRMS (FAB) Calcd. for $C_{33}H_{43}N_6O_9$: 667.30915. Observed m/z 667.31059. Anal. Calcd. for $C_{33}H_{42}N_6O_9 \cdot H_2O$: C, 57.88; H, 6.48; N, 12.27. Found: C, 57.83; H, 6.37; N, 12.40.

Example 77

(2S,3S)-2-(3-Methyl-1-amido-butylcarbamoyl)-3-(N²-(3-phenylpropanoylvalylalanyl)-N¹-carboxymethylhydrazinocarbonyl)oxirane (PhPr-Val-Ala-AAsp-(2S,3S)-EP-CO-Leu-NH₂). $^1$H NMR (DMSO-d$_6$): 0.74–0.87 (m, 12H, Val and Leu CH₃), 1.17 (d, 3H, Ala CH₃), 1.45 (m, 2H, Leu CH₂), 1.54 (m, 1H, Leu CH), 1.88 (m, 1H, Val CH), 2.40 (m, 2H, PhCH₂), 2.78 (t, 2H, PhCH₂CH₂CO), 3.32 (s, 2H, AAsp CH₂COOH), 3.56 (s, 2H, epoxy), 4.16 (m, 2H, α-H), 4.26 (m, 1H, α-H), 7.00 (s, 1H, NH), 7.15–7.23 (m, 6H, Ph and NH), 7.42 (s, 1H, NH), 7.85 (d, 1H, NH), 8.25 (s, 1H, NH), 8.55 (b, 1H, NH), 10.85 (b, 1H, COOH). HRMS (FAB) Calcd. for $C_{29}H_{43}N_6O_9$: 619.30915. Observed m/z 619.3129. Anal. Calcd. for $C_{29}H_{42}N_6O_9 \cdot H_2O$: C, 54.71; H, 6.97; N, 13.20. Found: C, 54.40; H, 6.89; N, 13.18.

Example 78

(2R,3R)-2-(3-Methyl-1-amido-butylcarbamoyl)-3-(N²-(3-phenylpropanoylvalylalanyl)-N¹-carboxymethylhydrazinocarbonyl)oxirane (PhPr-Val-Ala-AAsp-(2R,3R)-EP-CO-Leu-NH₂). $^1$H NMR (DMSO-d$_6$): 0.73–0.87 (m, 12H, Val and Leu CH₃), 1.17 (d, 3H, Ala CH₃), 1.43 (m, 2H, Leu CH₂), 1.53 (m, 1H, Leu CH), 1.87 (m, 1H, Val CH), 2.40 (m, 2H, PhCH₂), 2.77 (t, 2H, PhCH₂CH₂CO), 3.32 (s, 2H, AAsp CH₂COOH), 3.48 (s, 2H, epoxy), 4.20 (m, 3H, α-H), 6.97(s, 1H, NH), 7.15–7.24 (m, 6H, Ph and NH), 7.42 (s, 1H, NH), 7.85 (d, 1H, NH), 8.25 (s, 1H, NH), 8.55 (d, 1H, NH), 10.85 (b, 1H, COOH). HRMS (FAB) Calcd. for $C_{29}H_{43}N_6O_9$: 619.30915. Observed m/z 619.31200. Anal. Calcd. for $C_{29}H_{42}N_6O_9 \cdot 0.7H_2O$: C, 55.18; H, 6.88, N, 13.32. Found: C, 55.34; H, 6.81; N, 13.31.

Example 79

(2S,3S)-2-(1-Amido-phenethylcarbamoyl)-3-(N$^2$-(3-phenylpropanoylvalylalanyl)-N$^1$-carboxymethylhydrazinocarbonyl)oxirane (PhPr-Val-Ala-AAsp-(2S,3S)-EP-CO-Phe-NH$_2$). $^1$H NMR (DMSO-d$_6$): 0.76 (m, 6H, Val CH$_3$), 1.15 (d, 3H, Ala CH$_3$), 1.90 (m, 1H, Val CH), 2.42 (m, 2H, PhCH$_2$), 2.80 (m, 3H, Phe PhCH$_2$ and PhCH$_2$CH$_2$CO), 3.00 (m, 1H, Phe PhCH$_2$), 3.32 (s, 2H, AAsp CH$_2$COOH), 3.56 (s, 2H, epoxy), 4.16 (m, 2H, α-H), 4.50 (m, 1H, Phe α-H), 7.13–7.30 (m, 12H, Ph and NH), 7.54 (s, 1H, NH), 7.84 (d, 1H, NH), 8.25 (s, 1H, NH), 8.70 (d, 1H, NH), 10.85 (b, 1H, COOH). HRMS (FAB) Calcd. for C$_{32}$H$_{41}$N$_6$O$_9$: 653.29350. Observed m/z 653.29936. Anal. Calcd. for C$_{32}$H$_{40}$N$_6$O$_9$·H$_2$O: C, 57.30; H, 6.31; N, 12.53. Found: C, 57.53; H, 6.14; N, 12.16.

Example 80

(2R,3R)-2-(1-Amido-phenethylcarbamoyl)-3-(N$^2$-(3-phenylpropanoylvalylalanyl)-N$^1$-carboxymethylhydrazinocarbonyl)oxirane (PhPr-Val-Ala-AAsp-(2R,3R)-EP-CO-Phe-NH$_2$). $^1$H NMR (DMSO-d$_6$): 0.77 (m, 6H, Val CH$_3$), 1.15 (d, 3H, Ala CH$_3$), 1.88 (m, 1H, Val CH), 2.43 (m, 2H, PhCH$_2$), 2.80 (m, 3H, Phe PhCH$_2$ and PhCH$_2$CH$_2$CO), 2.95 (m, 1H, Phe PhCH$_2$), 3.32 (s, 2H, AAsp CH$_2$COOH), 3.47 (s, 2H, epoxy), 4.15 (m, 2H, α-H), 4.45 (m, 1H, Phe α-H), 7.13–7.30 (m, 11H, Ph and NH), 7.45 (s, 1H, NH), 7.83 (d, 1H, NH), 8.00 (d, 1H, NH), 8.15 (b, 1H, NH), 8.30 (s, 1H, NH), 10.88 (s, 1H, COOH). HRMS (FAB) Calcd. for C$_{32}$H$_{41}$N$_6$O$_9$: 653.29350. Observed 653.29525. Anal. Calcd. for C$_{32}$H$_{40}$N$_6$O$_9$·0.5H$_2$O: C, 58.09; H, 6.20; N, 12.70. Found: C, 57.83; H, 6.31; N, 12.84.

Example 81

(2S,3S)-2-(2-Amido-phenyl(4-hydroxy)ethylcarbamoyl)-3-(N$^2$-(3-phenylpropanoylvalylalanyl)-N$^1$-carboxymethylhydrazinocarbonyl)oxirane (PhPr-Val-Ala-AAsp-(2S,3S)-EP-CO-Tyr-NH$_2$). $^1$H NMR (DMSO-d$_6$): 0.78 (m, 6H, Val CH$_3$), 1.08 (d, 3H, Ala CH$_3$), 1.90 (m, 1H, Val CH), 2.42 (m, 2H, PhCH$_2$), 2.77 (m, 3H, Tyr PhCH$_2$ and PhCH$_2$CH$_2$CO), 2.88 (m, 1H, Tyr PhCH$_2$), 3.32 (s, 2H, AAsp CH$_2$COOH), 3.65 (d, 2H, epoxy), 4.16 (t, 1H, α-H), 4.32 (m, 2H, α-H), 6.59 (d, 2H, Tyr Ph), 6.95 (d, 2H, Tyr Ph), 7.10–7.22 (m, 6H, Ph and NH), 7.38 (s, 1H, NH), 7.50 (d, 1H, NH), 7.85 (d, 1H, NH), 8.23 (s, 1H, NH), 9.13 (d, 1H, NH), 10.80 (b, 1H, COOH). HRMS (FAB) Calcd. for C$_{32}$H$_{41}$N$_6$O$_{10}$: 669.2884. Observed m/z 669.2879.

Anal. Calcd. for C$_{32}$H$_{40}$N$_6$O$_{10}$·H$_2$O: C, 55.97; H, 6.16; N, 12.24. Found: C, 55.72; H, 6.04; N, 11.98.

Example 82

(2S,3S)-3-(N$^2$-(N-Benzyloxycarbonylaspartylglutamylvalyl)-N$^1$-carboxymethylhydrazinocarbonyl)oxirane-2-carboxylic Acid Benzyl Ester (Cbz-Asp-Glu-Val-AAsp-(2S,3S)-EP-COOCH$_2$Ph). $^1$H NMR (DMSO-d$_6$): 0.85 (m, 6H, Val), 1.80–2.24 (m, 3H, Val, Glu), 2.41 (m, 2H, Glu), 2.65–2.90 (m, 2H, Asp), 3.60 and 4.00 (d, 2H, epoxy), 4.05–4.12 (m, 2H, NCH$_2$COOH), 4.10–4.40 (m, 3H, α-H), 5.05 (m, 4H, Cbz), 6.05 (m, 1H, NH), 7.20–7.40 (m, 10H, Ph), 7.85 (m, 2H, NH), 9.05 (m, 1H, NH). HRMS (ESI) Calcd. for C$_{47}$H$_{66}$N$_5$O$_{15}$: 940.5. Observed m/z 940.5. Anal. Calcd. for C$_{35}$H$_{41}$N$_5$O$_{15}$·1.5H$_2$O: C, 52.60; H, 5.55; N, 8.76. Found: C, 52.59; H, 5.37; N, 8.76.

Example 83

(2S,3S)-2-(2-Benzylcarbamoyl)-3-(N$^2$-(N-benzyloxycarbonylaspartylglutamylvalyl)-N$^1$-carboxymethylhydrazinocarbonyl)oxirane (Cbz-Asp-Glu-Val-AAsp-(2S,3S)-EP-CONHCH$_2$Ph). $^1$H NMR (CDCl$_3$): 0.97 (m, 6H, Val), 1.9–2.3 (m, 3H, Val and Glu), 2.41 (m, 2H, Glu), 2.80–2.95 (m, 2H, Asp), 3.63 and 3.97 (d, 2H, epoxy), 4.05–4.22 (m, 4H, NCH$_2$COOH), 4.20–4.55 (m, 3H, α-H), 4.45 (m, 2H, NHCH$_2$Ph), 5.05 (m, 2H, Cbz), 7.20–7.40 (m, 10H, Ph), 6.15 (m, 1H, NH), 6.60 (1H, NH), 7.85 (m, 2H, NH). HRMS (ESI) Calcd. for C$_{35}$H$_{43}$N$_6$O$_{14}$: 771.3. Observed m/z 771.4. Anal. Calcd. for C$_{35}$H$_{42}$N$_6$O$_{14}$·2.2H$_2$O: C, 51.86; H, 5.77; N, 10.36. Found: C, 51.92; H, 5.66; N, 10.39.

Example 84

(2S,3S)-2-(2-Phenethylcarbamoyl)-3-(N$^2$-(N-benzyloxycarbonylglutamylvalyl)-N$^1$-carboxymethylhydrazinocarbonyl)oxirane (Cbz-Glu-Val-AAsp-(2S,3S)-EP-CONHCH$_2$CH$_2$Ph). 1H NMR (DMSO-d$_6$): 0.95 (d, 6H, Val), 1.20 (t, 3H, OCH$_2$CH$_3$), 1.60–2.10 (m, 3H, Val and Glu), 2.21 (m, 2H, Glu), 3.60 and 4.10 (d, 2H, epoxy), 3.90–4.20 (m, 4H, NCH$_2$COOH, and OCH$_2$CH$_3$), 4.20–4.30 (m, 2H, α-H), 5.05 (m, 2H, Cbz), 7.20–7.40 (m, 5H, Ph), 8.00 (m, 1H, NH), 11.00 (m, COOH). HRMS (FAB) Calcd. for C$_{32}$H$_{40}$N$_5$O$_{11}$: 670.2724. Observed m/z 670.2822. Anal. Calcd. for C$_{32}$H$_{39}$N$_5$O$_{11}$·H$_2$O: C, 55.88; H, 6.00; N, 10.19. Found: C, 55.91; H, 5.89; N, 10.32.

Example 85

(2R,3R)-2-(1-Amido-phenethylcarbamoyl)-3-(N$^2$-(N-benzyloxycarbonylaspartylglutamylvalyl)-N$^1$-carboxymethylhydrazinocarbonyl)oxirane (Cbz-Glu-Val-AAsp-(2R,3R)-EP-CO-Phe-NH$_2$). $^1$H NMR (DMSO-d$_6$): 0.94 (m, 6H, Val), 1.62–2.00 (m, 3H, Val and Glu), 2.20 (m, 2H, Glu), 2.80 and 3.00 (m, 2H, Phe), 3.60 and 4.05 (d, 2H, epoxy), 4.05 (m, 2H, NCH$_2$COOH), 4.05–4.40 (m, 3H, α-H), 5.10 (m, 2H, Cbz), 7.0 (s, 2H, NH$_2$), 7.10–7.40 (m, 10H, Ph), 8.00 (m, 2H, NH). HRMS Calcd. for C$_{33}$H$_{41}$N$_6$O$_{12}$: 713.2782 Observed m/z 713.2811. Anal. Calcd. for C$_{33}$H$_{40}$N$_6$O$_{12}$·1.0H$_2$O: C, 54.21; H, 5.68; N, 11.34. Found: C, 54.24; H, 5.79; N, 10.50.

Example 86

(2S,3S)-3-(N$^2$-(N-Benzyloxycarbonylleucylglutamylthreonyl)-N$^1$-carboxymethylhydrazinocarbonyl)oxirane-2-carboxylic Acid Benzyl Ester (Cbz-Leu-Glu-Thr-AAsp-(2S,3S)-EP-COOCH$_2$Ph). $^1$H NMR (DMSO-d$_6$): 0.7–0.9 (t, 6H, Leu CH$_3$), 0.9–1.1 (d, 3H, Thr CH$_3$), 1.3–1.5 (m, 2H, Leu CH$_2$), 1.6–1.7 (m, 1H, CH Leu), 1.7–1.8 (m, 1H, Glu CH$_2$), 1.8–2.0 (m, 1H, Glu CH$_2$), 2.2–2.35 (m, 2H, Glu CH$_2$), 3.6 (s, 1H, epoxy), 3.9–4.1 (m, 4H, NCH$_2$COOH, epoxy, α-H), 4.1–4.3 (m, 1H, CH—OH), 4.3–4.4 (m, 2H, α-H), 4.95 (m, H, NH), 4.95–5.05 and 5.1–5.3 (m, 4H, Cbz), 7.20–7.50 (m, 10H, Ph), 7.78 (m, 1H, NH), 8.05 (m, 1H, NH), 11.00 (m, COOH). HRMS (FAB) Calcd. for C$_{36}$H$_{46}$N$_5$O$_{14}$: 772.30413. Observed m/z 772.30610. Anal. Calcd. for C$_{36}$H$_{46}$N$_5$O$_{14}$·H$_2$O: C, 54.75; H, 5.96; N, 8.87. Found: C, 54.78; H, 5.94; N, 8.87.

Example 87

(2S,3S)-2-(2-Phenethylcarbamoyl)-3-($N^2$-(N-benzyloxycarbonylleucylglutamylthreonyl)-$N^1$-carboxymethylhydrazinocarbonyl)oxirane (Cbz-Leu-Glu-Thr-AAsp-(2S,3S)-EP-CONHCH$_2$CH$_2$Ph). $^1$H NMR (DMSO-d$_6$): 0.83 (t, 6H, Leu CH$_3$), 1.00 (m, 3H, Thr CH$_3$), 1.40 (m, 2H, Leu CH$_2$), 1.60 (m, 1H, Leu CH), 1.75 and 1.90 (d of m, 2H, Glu CH$_2$), 2.23 (m, 2H, Glu CH$_2$), 2.71 (t, 2H, CH$_2$Ph), 3.32 (s, 2H, AAsp CH$_2$), 3.43 and 3.52 (d, 2H, epoxy), 3.92 (b, 2H, α-H), 4.02 (b, 1H, α-H), 4.19 (m, 1H, Thr CH), 4.34 (m, 2H, NCH$_2$), 4.99 (s, 2H, Z), 7.15–7.35 (m, 10H, Ph), 7.40 (d, 1H, NH), 7.78 (b, 1H, NH), 8.00 (b, 1H, NH), 8.15 (s, 1H, NH), 8.20 (b, 1H, NH), 10.80 (b, 2H. COOH). HRMS (FAB) Calcd. for C$_{37}$H$_{49}$N$_6$O$_{13}$: 785.3358. Observed m/z 785.3400. Anal. Calcd. for C$_{37}$H$_{48}$N$_6$O$_{13}$.H$_2$O: C, 55.35; H, 6.28; N, 10.47. Found: C, 54.96; H, 6.13; N, 10.21.

Example 88

(2S,3S)-2-(1-Benzylcarbamoyl-ethylcarbamoyl)-3-($N^2$-(N-benzyloxycarbonylleucylglutamylthreonyl)-$N^1$-carboxymethylhydrazinocarbonyl)oxirane (Cbz-Leu-Glu-Thr-AAsp-(2S,3S)-EP-CO-Ala-NHBzl). $^1$H NMR (DMSO-d$_6$): 0.83 (t, 6H, Leu CH$_3$), 0.99 (d, 3H, Thr CH$_3$), 1.25 (d, 3H, Ala CH$_3$), 1.39 (m, 2H, Leu CH$_2$), 1.60 (m, 1H, Leu CH), 1.75 and 1.90 (d of m, 2H, Glu CH$_2$), 2.24 (m, 2H, Glu CH$_2$), 3.32 (s, 2H, AAsp CH$_2$), 3.56 and 3.64 (d, 2H, epoxy), 3.95 (b, 1H, α-H), 4.02 (b, 2H, α-H), 4.19 (m, 1H, α-H), 4.26 (d, 1H, Thr CH), 4.35 (m, 2H, CH$_2$Ph), 4.99 (s, 2H, Z), 7.15–7.35 (m, 11H, Ph and NH), 7.40 (d, 1H, NH), 7.75 (b, 1H, NH), 8.05 (d, 1H, NH), 8.45 (m, 2H, NH), 10.85 (b, 2H. COOH). HRMS (FAB) Calcd. for C$_{39}$H$_{52}$N$_7$O$_{14}$: 842.3572. Observed m/z 842.3336. Anal. Calcd. for C$_{39}$H$_{51}$N$_7$O$_{14}$.H$_2$O: C, 54.48; H, 6.21; N, 11.40. Found: C, 53.83; H, 5.96; N, 11.10.

Example 89

(2S,3S)-3-($N^1$-(N-Benzyloxycarbonylisoleucylglutamylthreonyl)-$N^1$-carboxymethylhydrazinocarbonyl)oxirane-2-carboxylic Acid Benzyl Ester (Cbz-Ile-Glu-Thr-AAsp-(2S13S)-EP-COOCH$_2$Ph). $^1$H NMR (DMSO-d$_6$): 0.8 (m, 6H, Ile CH$_3$), 0.9–1.2 (m, 4H, Thr CH$_3$ and Ile CH$_2$), 1.3–1.5 (m, 1H, Ile CH$_2$), 1.6–1.8 (m, 2H, CH Ile and Glu CH$_2$), 1.8–2.0 (m, 1H, Glu CH$_2$), 2.2–2.3 (m, 2H, Glu CH$_2$), 3.55 (d, 1H, epoxy), 3.9–4.0 (m, 3H, NCH$_2$COOH and CH—OH), 4.05 (d, 1H, epoxy), 4.2 (m, 1H, α-H), 4.4 (m, 2H, α-H), 4.95 (m, 1H, NH), 5–5.05 and 5.1–5.2 (m, 4H, Cbz), 7.20–7.40 (m, 10H, Ph), 7.80 (m, 1H, NH), 8.1 (m, 1H, NH), 11.00 (m, COOH). HRMS (FAB) Calcd. for C$_{36}$H$_{46}$N$_5$O$_{14}$: 772.30413. Observed m/z 772.30898. Anal. Calcd. for C$_{36}$H$_{45}$N$_5$O$_{14}$.H$_2$O: C, 54.75; H, 5.96; N, 8.87. Found: C, 54.97; H, 5.80; N, 8.91.

Example 90

(2R,3R)-3-($N^2$-(N-Benzyloxycarbonylisoleucylglutamylthreonyl)-$N^1$-carboxymethylhydrazinocarbonyl)oxirane-2-carboxylic Acid Benzyl Ester (Cbz-Ile-Glu-Thr-AAsp-(2R,3R)-EP-COOCH$_2$Ph). $^1$H NMR (DMSO-d$_6$): 0.7–0.9 (m, 6H, Ile CH$_3$), 0.9–1.2 (m, 4H, Thr CH$_3$ and Ile CH$_2$), 1.4 (m, 1H, Ile CH$_2$), 1.6–1.8 (m, 2H, CH Ile and Glu CH$_2$), 1.8–2.0 (m, 1H, Glu CH$_2$), 2.2–2.35 (m, 2H, Glu CH$_2$), 3.55–3.6 (d, 1H, epoxy), 3.8–4.0 (m, 3H, NCH$_2$COOH and CH—OH), 4.05 (d, 1H, epoxy), 4.15 (m, 1H, α-H), 4.3–4.5 (m, 2H, α-H), 4.9–5.1 and 5.1–5.3 (m, 4H, Cbz), 7.20–7.50 (m, 10H, Ph), 7.7–7.9 (m, 1H, NH), 8–8.15 (m, 1H, NH), 11.00 (m, COOH). HRMS (FAB) Calcd. for C$_{36}$H$_{46}$N$_5$O$_{14}$: 772.30413. Observed m/z 772.30837. Anal. Calcd. for C$_{36}$H$_{45}$N$_5$O$_{14}$.H$_2$O: C, 54.75; H, 5.96; N, 8.87. Found: C, 54.51; H, 5.82; N, 8.82.

Example 91

(2R,3R)-2-(2-Benzylcarbamoyl)-3-($N^2$-(N-benzyloxycarbonylisoleucylglutamylthreonyl)-$N^1$-carboxymethylhydrazinocarbonyl)oxirane (Cbz-Ile-Glu-Thr-AAsp-(2R,3R)-EP-CONHCH$_2$Ph). $^1$H NMR (DMSO-d$_6$): 0.7–0.9 (m, 6H, Ile CH$_3$), 0.9–1.15 (m, 4H, Thr CH$_3$ and Ile CH$_2$), 1.4 (m, 1H, Ile CH$_2$), 1.65–1.8 (m, 2H, CH Ile and-Glu CH$_2$), 1.8–2.0 (m, 1H, Glu CH$_2$), 2.2–2.3 (m, 2H, Glu CH$_2$), 3.5 (d, 1H, epoxy), 3.8–4.0 (m, 3H, NCH$_2$COOH and CH—OH), 4.03 (d, 1H, epoxy), 4.1–4.2 (m, 1H, α-H), 4.3–4.4 (m, 2H, NHCH$_2$Ph), 4.4 (m, 2H, α-H), 4.9–5.1 (m, 2H, Cbz), 7.15–7.40 (m, 10H, Ph), 7.85 (m, 1H, NH), 8.05 (m, 1H, NH), 11.00 (m, COOH). HRMS (FAB) Calcd. for C$_{36}$H$_{47}$N$_6$O$_{13}$: 771.32011. Observed m/z 771.33322. Anal. Calcd. for C$_{36}$H$_{46}$N$_6$O$_{13}$.1.25H$_2$O: C, 54.51; H, 6.12; N, 10.60. Found: C, 54.30; H, 6.04; N, 10.36.

Example 92

(2S,3S)-2-(1-Benzylcarbamoyl-ethylcarbamoyl)-3-($N^2$-(N-benzyloxycarbonylisoleucylglutamylthreonyl)-$N^1$-carboxymethylhydrazinocarbonyl)oxirane (Cbz-Ile-Glu-Thr-AAsp-(2S,3S)-EP-CO-Ala-NHBzl). $^1$H NMR (DMSO-d$_6$): 0.79 (m, 6H, Ile CH$_3$), 1.01 (d, 3H, Thr CH$_3$), 1.10 (m, 2H, Ile CH$_2$), 1.25 (d, 3H, Ala CH$_3$), 1.39 (m, 1H, Ile CH), 1.70 and 1.90 (d of m, 2H, Glu CH$_2$), 2.24 (m, 2H, Glu CH$_2$), 3.32 (s, 2H, AAsp CH$_2$), 3.57 (s, 2H, epoxy), 3.88 (t, 1H, α-H), 3.95 (b, 2H, α-H), 4.20 (m, 1H, α-H), 4.28 (d, 1H, Thr CH), 4.36 (m, 2H, CH$_2$Ph), 4.99 (s, 2H, Z), 7.15–7.35 (m, 11H, Ph and NH), 7.40 (d, 1H, NH), 7.75 (b, 1H, NH), 8.05 (d, 1H, NH), 8.45 (m, 3H, NH), 10.85 (b, 2H, COOH). HRMS (FAB) Calcd. for C$_{39}$H$_{52}$N$_7$O$_{14}$: 842.35722. Observed m/z 842.36598. Anal. Calcd. for C$_{39}$H$_{51}$N$_7$O$_{14}$.2H$_2$O: C, 53.42; H, 6.31; N, 11.18. Found: C, 53.06; H, 6.25; N, 10.97.

Example 93

(2S,3S)-3-($N^2$-(N-Morpholinylcarbonyl)-$N^1$-phenethylhydrazinocarbonyl)oxirane-2-carboxylic Acid Ethyl Ester (Morph-CO-AHph-(2S,3S)-EP-COOEt) was obtained using the EDC/HOBt coupling method. The crude product was purified by column chromatography using 1:13 MeOH:CH$_2$Cl$_2$ as an eluent, then rechromatographed using 1:19 MeOH:CH$_2$Cl$_2$ as an eluent, and was rechromatographed a final time using 50:50 (2:1 EtoAc:Hexane):(1:19 MeOH:CH$_2$Cl$_2$) as the eluent; oil (8% yield). HRMS (FAB) Calcd. for C$_{19}$H$_{26}$N$_3$O$_6$: 392.18216. Observed m/z 392.18454. $^1$H NMR (DMSO-d$_6$): 1.25 (t, 3H, OCH$_2$CH$_3$), 2.8 (m, 2H, CH$_2$Ph), 3.3–3.4 (m, 2H, NCH$_2$ morph), 3.4–3.6 (m, 6H, OCH$_2$, OCH$_2$ and NCH$_2$ morph), 3.7 (m, 1H, epoxy), 3.9 (m, 2H, NCH$_2$Cl$_2$), 4.1–4.2 (m, 3H, epoxy and OCH$_2$CH$_3$), 7.1–7.3 (m, 5H, Ph), 9.4 (s, 1H, NH). Anal. Calcd. for C$_{19}$H$_{25}$N$_3$O$_6$.0.25H$_2$O: C, 57.65; H, 6.45; N, 10.62. Found: C, 57.78; H, 6.69; N, 10.34.

The above specification and Examples fully disclose how to make and use the compounds of the present invention. However, the present invention is not limited to the particular embodiments described hereinabove, but includes all modifications thereof within the scope of the following claims. The various references to journals, patents, and other publications which are cited herein comprise the state of the art and are incorporated herein by reference.

What is claimed is:

1. A compound of the formula:

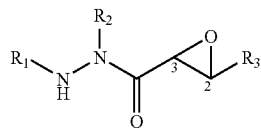

wherein,

R$_1$ is selected from the group consisting of M$_1$, M$_2$-AA$_1$, M$_2$-AA$_2$-AA$_1$, and M$_2$-AA$_3$-AA$_2$-AA$_1$;

M$_1$ is selected from the group consisting of NH$_2$—CO—, NH$_2$—CS—, NH$_2$—SO$_2$—, X—NH—CO—, X$_2$N—CO—, X—NH—CS—, X$_2$N—CS—, X—NH—SO$_2$—, X$_2$N—SO$_2$—, X—CO—, X—CS—, Y—SO$_2$—, Y—O—CO—, Y—O—CS—, phenyl substituted with K, phenyl disubstituted with K, and morpholine-CO—;

M$_2$ is selected from the group consisting of H, NH$_2$—CO—, NH$_2$—CS—, NH$_2$—SO$_2$—, X—NH—CO—, X$_2$N—CO—, X—NH—CS—, X$_2$N—CS—, X—NH—SO$_2$—, X$_2$N—SO$_2$—, X—CO—, X—CS—, Y—SO$_2$—, Y—O—CO—, Y—O—CS—, phenyl, phenyl substituted with K, phenyl disubstituted with K, and morpholine-CO—;

X is selected from the group consisting of H, C$_{1-10}$ alkyl, C$_{3-15}$ cyclized alkyl, C$_{1-10}$ fluoroalkyl, C$_{1-10}$ alkyl substituted with J, C$_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C$_{1-10}$ fluoroalkyl with an attached phenyl group, C$_{1-10}$ alkyl with an attached phenyl group, C$_{1-10}$ alkyl with two attached phenyl groups, C$_{1-10}$ alkyl with an attached phenyl group substituted with K, C$_{1-10}$ alkyl with two attached phenyl groups substituted with K, C$_{1-10}$ alkyl with an attached naphthyl group, C$_{1-10}$ alkyl with an attached naphthyl group substituted with K, C$_{1-10}$ alkyl with an attached phenoxy group, biotinyl, and C$_{1-10}$ alkyl with an attached phenoxy group substituted with K on the phenoxy group;

Y is selected from the group consisting of C$_{1-10}$ alkyl, C$_{3-15}$ cyclized alkyl, C$_{1-10}$ fluoroalkyl, C$_{1-10}$ alkyl substituted with J, C$_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C$_{1-10}$ fluoroalkyl with an attached phenyl group, C$_{1-10}$ alkyl with an attached phenyl group, C$_{1-10}$ alkyl with two attached phenyl groups, C$_{1-10}$ alkyl with an attached phenyl group substituted with K, C$_{1-10}$ alkyl with two attached phenyl groups substituted with K, C$_{1-10}$ alkyl with an attached naphthyl group, C$_{1-10}$ alkyl with an attached naphthyl group substituted with K, C$_{1-10}$ alkyl with an attached phenoxy group, biotinyl, and C$_{1-10}$ alkyl with an attached phenoxy group substituted with K on the phenoxy group;

J is selected from the group consisting of halogen, CO$_2$H, OH, CN, NO$_2$, NH$_2$, C$_{1-10}$ alkoxy, C$_{1-10}$ alkylamino, C$_{2-12}$ dialkylamino, C$_{1-10}$ alkyl-O—CO—, C$_{1-10}$ alkyl-O—CO—NH—, and C$_{1-10}$ alkyl-S—;

K is selected from the group consisting of halogen, C$_{1-10}$ alkyl, C$_{1-10}$ perfluoroalkyl, C$_{1-10}$ alkoxy, phenoxy, NO$_2$, CN, OH, CO$_2$H, amino, C$_{1-0}$ alkylamino, C$_{2-12}$ dialkylamino, C$_{1-10}$ acyl, and C$_{1-10}$ alkoxy-CO—, and C$_{1-10}$ alkyl-S—;

AA$_1$, AA$_2$, and AA$_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)—CO$_2$H, alpha-aminoheptanoic acid, NH$_2$—CH(CH$_2$-1-naphthyl)-CO$_2$H, NH$_2$—CH(CH$_2$-2-naphthyl)-CO$_2$H, NH$_2$—CH(CH$_2$-cyclohexyl)-CO$_2$H, NH$_2$—CH(CH$_2$-cyclopentyl)-CO$_2$H, NH$_2$—CH(CH$_2$-cyclobutyl)-CO$_2$H, NH$_2$—CH(CH$_2$-cyclopropyl)-CO$_2$H, trifluoroleucine, 4-fluorophenylalanine, lysine substituted on the epsilon nitrogen with a biotinyl group, and hexafluoroleucine;

R$_2$ is selected from the group consisting of C$_{1-10}$ alkyl, C$_{1-10}$ alkyl substituted with Q, C$_{1-10}$ alkyl substituted with phenyl, C$_{1-10}$ alkyl with an attached phenyl substituted with K, C$_{1-10}$ alkyl substituted with naphthyl, C$_{1-10}$ alkyl with an attached naphthyl substituted with K, phenyl, phenyl substituted with K, naphthyl, naphthyl substituted with K, C$_{1-10}$ alkyl substituted with CONH$_2$, C$_{1-10}$ alkyl substituted with CONHR$_4$, C$_{1-10}$ alkyl substituted with CO$_2$H, C$_{1-10}$ alkyl substituted with CO$_2$R$_4$, $_{CH2}$CH$_2$SCH$_3$, CH$_2$-3-indolyl, CH$_2$-2-thienyl, CH$_2$-2-furyl, CH$_2$-3-furyl, CH$_2$-2-imidazyl, C$_{1-10}$ alkyl substituted with G, C$_{1-10}$ alkyl with an attached phenyl substituted with G, C$_{1-10}$ alkyl with an attached naphthyl substituted with G, phenyl substituted with G, and naphthyl substituted with G;

R$_4$ is selected from the group consisting of C$_{1-10}$ alkyl and C$_{1-10}$ alkyl substituted with phenyl;

Q is selected independently from the group consisting of C$_{1-10}$ alkoxy, C$_{1-10}$ alkyl-S—, C$_{1-10}$ alkoxy substituted with phenyl, and C$_{1-10}$ alkyl-S— substituted with phenyl;

G is selected independently from the group consisting of amidino (—C(=NH)NH$_2$), guanidino (—NHC(=NH)NH$_2$), isothiureido (—S—C(=NH)NH$_2$), amino, C$_{1-6}$ alkylamino, C$_{2-12}$ dialkylamino, and imidazyl;

R$_3$ is selected independently from the group consisting of R$_5$, CO$_2$H, CO$_2$R$_5$, CONHR$_6$, CONR$_6$R$_7$, CO-AA$_4$-T,

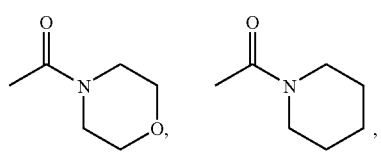

-continued

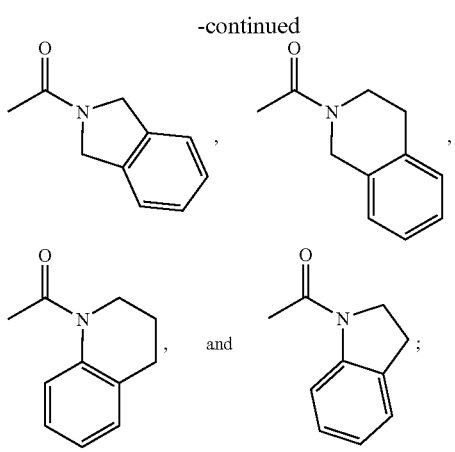

, and ;

$R_5$ is selected independently from the group consisting of $C_{1-10}$ alkyl, $C_{3-15}$ cyclized alkyl, $C_{1-10}$ alkyl with a phenyl group attached to the $C_{1-10}$ alkyl, $C_{3-15}$ cyclized alkyl with an attached phenyl group, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{3-15}$ cyclized alkyl with an attached phenyl group substituted with K, $C_{1-10}$ alkyl with a naphthyl group attached to the $C_{1-10}$ alkyl, $C_{3-15}$ cyclized alkyl with an attached naphthyl group, $C_{1-10}$ alkyl with an attached naphthyl group substituted with K, $C_{1-10}$ alkyl with an attached naphthyl group disubstituted with K, $C_{1-10}$ alkyl with an attached naphthyl group trisubstituted with K, and $C_{3-15}$ cyclized alkyl with an attached naphthyl group substituted with K;

T is selected independently from the group consisting of OH, $OR_8$, $NHR_9$, and $NR_8R_9$;

$AA_4$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2—CH(CH_2CHEt_2)—CO_2H$, alpha-aminoheptanoic acid, $NH_2—CH(CH_2$-1-naphthyl)-$CO_2H$, $NH_2—CH(CH_2$-2-naphthyl)-$CO_2H$, $NH_2—CH(CH_2$-cyclohexyl)-$CO_2H$, $NH_2—CH(CH_2$-cyclopentyl)-$CO_2H$, $NH_2—CH(CH_2$-cyclobutyl)-$CO_2H$, $NH_2—CH(CH_2$-cyclopropyl)-$CO_2H$, trifluoroleucine, 4-fluorophenylalanine, lysine substituted on the epsilon nitrogen with a biotinyl group, and hexafluoroleucine;

$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-10}$ alkyl with a morpholine [$—N(CH_2CH_2)O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, $—CH_2CH_2CH_2OCH_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, $—NH—CH_2CH_2$-(4-hydroxyphenyl), $—NH—CH_2CH_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl;

$R_8$ and $R_9$ are selected independently from the group consisting of H, $C_{1-10}$ alkyl, phenyl, nitrophenyl, and $C_{1-10}$ alkyl substituted with phenyl; or a pharmaceutically acceptable salt, pharmaceutically derivative, hydrate or solvate thereof.

2. A compound according to claim 1 wherein:

$R_1$ is selected from the group consisting of $M_2$-$AA_1$, $M_2$-$AA_2$-$AA_1$, and $M_2$-$AA_3$-$AA_2$-$AA_1$;

$M_2$ is selected from the group consisting of H, X—CO—, X—NH—CO—, Y—$SO_2$—, and Y—O—CO—;

X is selected from the group consisting of H, $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

Y is selected from the group consisting of $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

J is selected from the group consisting of $CO_2H$, OH, $NH_2$, $C_{1-10}$ alkoxy, $C_{1-10}$ alkylamino, and $C_{1-10}$ alkyl-O—CO—;

K is selected from the group consisting of $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, and $NH_2$—$CH(CH_2$-cyclopropyl)-$CO_2H$;

$R_2$ is selected from the group consisting of $C_{1-10}$ alkyl substituted with $CONH_2$, $C_{1-10}$ alkyl substituted with $CO_2H$, and $C_{1-10}$ alkyl substituted with $CO_2R_4$;

$R_4$ is selected from the group consisting of $C_{1-10}$ alkyl and $C_{1-10}$ alkyl substituted with phenyl;

$R_3$ is selected independently from the group consisting of $R_5$, $CO_2H$, $CO_2R_5$, $CONHR_6$, $CONR_6R_7$, and $CO$-$AA_4$-T;

$R_5$ is selected independently from the group consisting of $C_{1-10}$ alkyl, $C_{1-10}$ alkyl with a phenyl group attached to the $C_{1-10}$ alkyl, $C_{1-10}$ alkyl with an attached phenyl group substituted with K, $C_{1-10}$ alkyl with a naphthyl group attached to the $C_{1-10}$ alkyl, and $C_{1-10}$ alkyl with an attached naphthyl group substituted with K.

$AA_4$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, and $NH_2$—$CH(CH_2$-cyclopropyl)-$CO_2H$;

$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, —NH—$CH_2CH_2$-(4-hydroxyphenyl), —NH—$CH_2CH_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl;

$R_8$ and $R_9$ are selected independently from the group consisting of H, $C_{1-10}$ alkyl, phenyl, nitrophenyl, and $C_{1-10}$ alkyl substituted with phenyl.

3. A compound according to claim 2 wherein

X is selected from the group consisting of H, $C_{1-10}$ alkyl, phenyl, naphthyl, $C_{1-10}$ alkyl with an attached phenyl group, $C_{1-10}$ alkyl with an attached naphthyl group, and $C_{1-10}$ alkyl substituted with $CO_2H$;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—$CH(CH_2$-1-naphthyl)-$CO_2H$, and $NH_2$—$CH(CH_2$-2-naphthyl)-$CO_2H$;

$R_5$ is selected independently from the group consisting of $C_{1-10}$ alkyl and $C_{1-10}$ alkyl with a phenyl group attached to the $C_{1-10}$ alkyl;

$AA_4$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, citrulline, homoarginine, sarcosine, $NH_2$—$CH(CH_2$-1-naphthyl)-$CO_2H$, and $NH_2$—$CH(CH_2$-2-naphthyl)-$CO_2H$;

$R_6$ and $R_7$ are selected independently from the group consisting of H, $C_{1-10}$ alkyl, $C_{1-10}$ alkyl with a phenyl group attached to the $C_{1-10}$ alkyl, $C_{1-10}$ alkyl with two phenyl groups attached to the $C_{1-10}$ alkyl, phenyl substituted with K, $C_{1-10}$ alkyl with an attached phenyl group substituted with K, $C_{1-10}$ alkyl with an attached phenyl group disubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, and $C_{1-5}$ alkyl with an attached phenyl and a hydroxyl attached to the $C_{1-5}$ alkyl.

4. A compound according to claim 1 wherein wherein, $R_1$ is selected from the group consisting of $M_2$-$AA_1$, $M_2$-$AA_2$-$AA_1$, and $M_2$-$AA_3$-$AA_2$-$AA_1$;

$M_2$ is selected from the group consisting of H, X—CO—, X—NH—CO—, Y—$SO_2$—, and Y—O—CO—;

X is selected from the group consisting of H, $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

Y is selected from the group consisting of $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

J is selected from the group consisting of $CO_2H$, OH, $NH_2$, $C_{1-10}$ alkoxy, $C_{1-10}$ alkylamino, and $C_{1-10}$ alkyl-O—CO—;

K is selected from the group consisting of $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, and $NH_2$—$CH(CH_2$-cyclopropyl)-$CO_2H$;

$R_2$ is selected from the group consisting of $C_{1-10}$ alkyl, $C_{1-10}$ alkyl substituted with Q, $C_{1-10}$ alkyl substituted with phenyl, $C_{1-10}$ alkyl with an attached phenyl substituted with K, $C_{1-10}$ alkyl substituted with naphthyl, $C_{1-10}$ alkyl with an attached naphthyl substituted with K, and phenyl;

$R_3$ is selected independently from the group consisting of $R_5$, $CO_2H$, $CO_2R_5$, $CONHR_6$, $CONR_6R_7$, and CO-$AA_4$-T;

$R_5$ is selected independently from the group consisting of $C_{1-10}$ alkyl, $C_{1-10}$ alkyl with a phenyl group attached to the $C_{1-10}$ alkyl, $C_{1-10}$ alkyl with an attached phenyl group substituted with K, $C_{1-10}$ alkyl with a naphthyl group attached to the $C_{1-10}$ alkyl, and $C_{1-10}$ alkyl with an attached naphthyl group substituted with K.

$AA_4$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, and $NH_2$—$CH(CH_2$-cyclopropyl)-$CO_2H$;

$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, —NH—$CH_2CH_2$-(4-hydroxyphenyl), —NH—$CH_2CH_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl;

$R_8$ and $R_9$ are selected independently from the group consisting of H, $C_{1-10}$ alkyl, phenyl, nitrophenyl, and $C_{1-10}$ alkyl substituted with phenyl.

5. A compound according to claim 4 wherein

X is selected from the group consisting of H, $C_{1-10}$ alkyl, phenyl, naphthyl, $C_{1-10}$ alkyl with an attached phenyl group, $C_{1-10}$ alkyl with an attached naphthyl group, and $C_{1-10}$ alkyl substituted with $CO_2H$;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—$CH(CH_2$-1-naphthyl)-$CO_2H$, and $NH_2$—$CH(CH_2$-2-naphthyl)-$CO_2H$;

$R_5$ is selected independently from the group consisting of $C_{1-10}$ alkyl and $C_{1-10}$ alkyl with a phenyl group attached to the $C_{1-10}$ alkyl;

$AA_4$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—$CH(CH_2$-1-naphthyl)-$CO_2H$, and $NH_2$—$CH(CH_2$-2-naphthyl)-$CO_2H$;

$R_6$ and $R_7$ are selected independently from the group consisting of H, $C_{1-10}$ alkyl, $C_{1-10}$ alkyl with a phenyl group attached to the $C_{1-10}$ alkyl, $C_{1-10}$ alkyl with two phenyl groups attached to the $C_{1-10}$ alkyl, phenyl substituted with K, $C_{1-10}$ alkyl with an attached phenyl group substituted with K, $C_{1-10}$ alkyl with an attached phenyl group disubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, and $C_{1-5}$ alkyl with an attached phenyl and a hydroxyl attached to the $C_{1-5}$ alkyl.

6. A compound according to claim 1 wherein
$R_1$ is selected from the group consisting of $M_2$-$AA_1$, $M_2$-$AA_2$-$AA_1$, and $M_2$-$AA_3$-$AA_2$-$AA_1$;
$M_2$ is selected from the group consisting of H, X—CO—, X—NH—CO—, Y—SO$_2$—, and Y—O—CO—;
X is selected from the group consisting of H, $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;
Y is selected from the group consisting of $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;
J is selected from the group consisting of $CO_2H$, OH, $NH_2$, $C_{1-10}$ alkoxy, $C_{1-10}$ alkylamino, and $C_{1-10}$ alkyl-O—CO—;
K is selected from the group consisting of $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino;
$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, $NH_2$—CH($CH_2$-1-naphthyl)-$CO_2H$, $NH_2$—CH($CH_2$-2-naphthyl)-$CO_2H$, $NH_2$—CH($CH_2$-cyclohexyl)-$CO_2H$, $NH_2$—CH($CH_2$-cyclopentyl)-$CO_2H$, $NH_2$—CH($CH_2$-cyclobutyl)-$CO_2H$, and $NH_2$—CH($CH_2$-cyclopropyl)-$CO_2H$;
$R_2$ is selected from the group consisting of $C_{1-10}$ alkyl substituted with G, $C_{1-10}$ alkyl with an attached phenyl substituted with G, $C_{1-10}$ alkyl with an attached naphthyl substituted with G, phenyl substituted with G, and naphthyl substituted with G;
G is selected independently from the group consisting of amidino (—C(=NH)$NH_2$), guanidino (—NHC(=NH)$NH_2$), isothiureido (—S—C(=NH)$NH_2$), amino, and $C_{1-6}$ alkylamino;
$R_3$ is selected independently from the group consisting of $R_5$, $CO_2H$, $CO_2R_5$, $CONHR_6$, and $CONR_6R_7$;
$R_5$ is selected independently from the group consisting of $C_{1-10}$ alkyl, $C_{1-10}$ alkyl with a phenyl group attached to the $C_{1-10}$ alkyl, $C_{1-10}$ alkyl with an attached phenyl group substituted with K, $C_{1-10}$ alkyl with a naphthyl group attached to the $C_{1-10}$ alkyl, and $C_{1-10}$ alkyl with an attached naphthyl group substituted with K;
$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, —NH—$CH_2CH_2$-(4-hydroxyphenyl), —NH—$CH_2CH_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl;
$R_8$ and $R_9$ are selected independently from the group consisting of H, $C_{1-10}$ alkyl, phenyl, nitrophenyl, and $C_{1-10}$ alkyl substituted with phenyl.

7. A compound according to claim 5 wherein
X is selected from the group consisting of H, $C_{1-10}$ alkyl, phenyl, naphthyl, $C_{1-10}$ alkyl with an attached phenyl group, $C_{1-10}$ alkyl with an attached naphthyl group, and $C_{1-10}$ alkyl substituted with $CO_2H$;
$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—CH($CH_2$-1-naphthyl)-$CO_2H$, and $NH_2$—CH($CH_2$-2-naphthyl)-$CO_2H$;
$R_5$ is selected independently from the group consisting of $C_{1-10}$ alkyl and $C_{1-10}$ alkyl with a phenyl group attached to the $C_{1-10}$ alkyl;
$AA_4$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—CH($CH_2$-1-naphthyl)-$CO_2H$, and $NH_2$—CH($CH_2$-2-naphthyl)-$CO_2H$;
$R_6$ and $R_7$ are selected independently from the group consisting of H, $C_{1-10}$ alkyl, $C_{1-10}$ alkyl with a phenyl group attached to the $C_{1-10}$ alkyl, $C_{1-10}$ alkyl with two phenyl groups attached to the $C_{1-10}$ alkyl, phenyl substituted with K, $C_{1-10}$ alkyl with an attached phenyl group substituted with K, $C_{1-10}$ alkyl with an attached phenyl group disubstituted with K, $C_{1-10}$ alkyl with two phenyl groups, attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the C$_{1-10}$ alkyl and disubstituted with K on the phenyl groups, C$_{3-20}$ cyclized alkyl with an attached phenyl group substituted with K, C$_{1-20}$ alkyl with an OH group attached to the alkyl, —CH$_2$CH$_2$CH$_2$OCH$_3$, and C$_{1-5}$ alkyl with an attached phenyl and a hydroxyl attached to the C$_{1-5}$ alkyl.

8. The compound of claim 1 wherein epoxide carbons 2 and 3 have stereochemistry selected from the group consisting of cis; trans; R,R; S,S; R,S; and S,R.

9. The composition of claim 1, wherein said composition is substantially optically pure.

10. The composition of claim 1, wherein said composition is racemic.

11. The composition of claim 9, wherein said composition substantially comprises a single optical isomer.

12. A compound selected from the group consisting of:
(a) APhe-(trans)-EP-COOEt,
(b) Cbz-APhe-(trans)-EP-COOEt,
(c) Cbz-APhe-(trans)-EP-CH$_2$CH$_2$Ph,
(d) Cbz-ALeu-(trans)-EP-COOEt,
(e) Cbz-AHph-(trans)-EP-COOEt,
(f) Ac-AHph-(trans)-EP-COOEt,
(g) Boc-Nva-AHph-(trans)-EP-COOEt,
(h) Boc-Nle-AHph-(trans)-EP-COOEt,
(i) Boc-Nle-AHph-(trans)-EP-CH$_2$CH$_2$Ph,
(j) Boc-Nva-AHph-(trans)-EP-CH$_2$CH$_2$Ph,
(k) Boc-Abu-AHph-(trans)-EP-CH$_2$CH$_2$Ph,
(l) Boc-Ala-AHph-(trans)-EP-CH$_2$CH$_2$Ph,
(m) Boc-Np2-ALeu-(trans)-EP-COOEt,
(n) Suc-Np2-ALeu-(trans)-EP-COOEt,
(o) Ac-Leu-ALeu-(trans)-EP-COOEt,
(p) Ac-Leu-AHph-(trans)-EP-COOEt,
(q) Nva-AHph-(trans)-EP-CH$_2$CH$_2$Ph.TFA,
(r) Nle-AHph-(trans)-EP-COOEt.TFA,
(s) Ala-AHph-(trans)-EP-CH$_2$CH$_2$Ph.TFA,
(t) Cbz-Leu-ALeu-(2S,3S)-EP-COOEt,
(u) Cbz-Leu-ALeu-(2R,3R)-EP-COOEt,
(v) Cbz-Leu-ALeu-(trans)-EP-COOEt,
(w) Cbz-Leu-ALeu-(cis)-EP-COOEt,
(x) Cbz-Phe-ALeu-(trans)-EP-COOEt,
(y) Cbz-Phe-ALeu-(trans)-EP-CH$_2$CH$_2$Ph,
(z) Cbz-Phe-APhe-(trans)-EP-CH$_2$CH$_2$Ph,
(aa) Cbz-Leu-AAbu-(trans)-EP-COOEt,
(bb) Cbz-Leu-AAbu-(trans)-EP-COOH,
(cc) Cbz-Leu-AHph-(cis)-EP-COOEt,
(dd) Cbz-Leu-AHph-(2S,3S)-EP-COOEt,
(ee) Cbz-Leu-AHph-(2R,3R)-EP-COOEt,
(ff) Cbz-Leu-AHph-(2S,3S)-EP-COOH,
(gg) Cbz-Leu-Leu-ALeu-(trans)-EP-COOEt,
(hh) Cbz-Leu-Leu-ALeu-(2S,3S)-EP-COOEt,
(ii) Cbz-Leu-Leu-ALeu-(2R,3R)-EP-COOEt,
(jj) Cbz-Leu-Leu-ALeu-(2S,3S)-EP-COOH,
(kk) Cbz-Leu-Phe-AGln-(2S,3S)-EP-COOEt,
(ll) Cbz-Leu-Phe-AGln-(2R,3R)-EP-COOEt,
(mm) Cbz-Leu-Phe-AGln-(trans)-EP-COOEt,
(nn) Cbz-Ala-Ala-AAsn-(trans)-EP-COOEt,
(oo) Cbz-Ala-Ala-AAsn-(2S,3S)-EP-COOEt,
(pp) Cbz-Ala-Ala-AAsn-(2R,3R)-EP-COOEt,
(qq) Cbz-Ala-Ala-AAsn-(cis)-EP-COOEt,
(rr) Cbz-Ala-Ala-AAsn-(trans)-EP-COOCH$_2$Ph,
(ss) Cbz-Ala-Ala-AAsn-(S,S)-EP-COOCH$_2$Ph,
(tt) Cbz-Ala-Ala-AAsn-(S,S)-EP-COOCH$_2$CH$_2$Ph,
(uu) Cbz-Ala-Ala-AAsn-(S,S)-EP-CONHCH$_2$Ph,
(vv) Cbz-Ala-Ala-AAsn-(S,S)-EP-CONHCH$_2$CH$_2$Ph,
(ww) Cbz-Ala-Ala-AAsn-(R,R)-EP-CO-Ala-NH-Bzl,
(xx) Cbz-Ala-Ala-AAsn-(S,S)-EP-CON(nBu)$_2$,
(yy) Cbz-Ala-Ala-AAsn-(S,S)-EP-CON(CH$_3$)CH$_2$Ph,
(zz) Cbz-Ala-Ala-AAsn-(trans)-EP-CH$_2$CH$_2$Ph,
(aaa) Cbz-Ala-Ala-AAsn-(trans)-EP-Ph-4-Cl,
(bbb) Cbz-Ala-Ala-NHN(CH$_2$COOEt)-(trans)-EP-COOEt,
(ccc) PhPr-Val-Ala-AAsp-(2R,3R)-EP-COOCH$_2$Ph,
(ddd) PhPr-Val-Ala-AAsp-(2S,3S)-EP-COOCH$_2$Ph,
(eee) PhPr-Val-Ala-AAsp-(trans)-EP-COOCH$_2$Ph,
(fff) PhPr-Val-Ala-AAsp-(trans)-EP-CH$_2$CH$_2$Ph,
(ggg) Cbz-Ile-Glu-Thr-AAsp-(2S,3S)-EP-COOEt,
(hhh) Cbz-Ile-Glu-Thr-AAsp-(2R,3R)-EP-COOEt,
(iii) Cbz-Leu-Glu-Thr-AAsp-(2S,3S)-EP-COOEt,
(jjj) Cbz-Leu-Glu-Thr-AAsp-(2R,3R)-EP-COOEt,
(kkk) Cbz-Asp-Glu-Val-AAsp-(2S,3S)-EP-COOEt,
(lll) Cbz-Asp-Glu-Val-AAsp-(2R,3R)-EP-COOEt,
(mmm) Cbz-Glu-Val-AAsp-(2S,3S)-EP-COOEt,
(nnn) PhPr-Val-Ala-AAsp-(2S,3S)-EP-CON(CH$_2$CH$_2$CH$_2$CH$_3$)$_2$,
(ooo) PhPr-Val-Ala-AAsp-(2S,3S)-EP-CON(CH$_2$Ph)$_2$,
(ppp) Cbz-Leu-Glu-Thr-AAsp-(2S,3S)-EP-CON(CH$_2$Ph)$_2$,
(qqq) Cbz-Ile-Glu-Thr-AAsp-(2S,3S)-EP-CON(CH$_2$Ph)$_2$,
(rrr) Cbz-Leu-Glu-Thr-AAsp-(2S,3S)-EP-CON(CH$_3$)CH$_2$Ph,
(sss) PhPr-Val-Ala-AAsp-(2S,3S)-EP-CON(CH$_3$)CH$_2$Ph,
(ttt) Cbz-Ile-Glu-Thr-AAsp-(2S,3S)-EP-CON(CH$_3$)CH$_2$Ph,
(uuu) PhPr-Leu-ALys-(2S,3S)-EP-CO$_2$Et,
(vvv) PhPr-Leu-Arn-(2S,3S)-EP-CO$_2$Et,
(www) Cbz-Val-AAsp-(S,S)-EP-COOEt,
(xxx) Cbz-Val-AAsp-(S,S)-EP-COOH,
(yyy) Cbz-Val-AAsp-(trans)-EP-CH$_2$CH$_2$Ph,
(zzz) Cbz-Val-AAsp-(trans)-EP-Ph-4-Cl,
(aaaa) PhPr-Val-Ala-AAsp-(S,S)-EP-COOEt,
(bbbb) PhPr-Val-Ala-AAsp-(R,R)-EP-COOEt,
(cccc) PhPr-Val-Ala-AAsp-(S,S)-EP-COOCH$_2$CH$_2$Ph,
(dddd) PhPr-Val-Ala-AAsp-(S,S)-EP-CONHCH$_2$CH$_3$,
(eeee) PhPr-Val-Ala-AAsp-(S,S)-EP-CONHCH$_2$Ph,
(ffff) PhPr-Val-Ala-AAsp-(R,R)-EP-CONHCH$_2$Ph,
(gggg) PhPr-Val-Ala-AAsp-(S,S)-EP-CONHCH$_2$CH$_2$Ph,
(hhhh) PhPr-Val-Ala-AAsp-(R,R)-EP-CONHCH$_2$CH$_2$Ph,
(iiii) PhPr-Val-Ala-AAsp-(S,S)-EP-CONHCH$_2$CH(OH)Ph,
(jjjj) PhPr-Val-Ala-AAsp-(R,R)-EP-CONHCH$_2$CH(OH)Ph,
(kkkk) PhPr-Val-Ala-AAsp-(S,S)-EP-CO-Ala-NHCH$_2$Ph,
(llll) PhPr-Val-Ala-AAsp-(R,R)-EP-CO-Ala-NHCH$_2$Ph,
(mmmm) PhPr-Val-Ala-AAsp-(S,S)-EP-CO-Leu-NH$_2$,
(nnnn) PhPr-Val-Ala-AAsp-(R,R)-EP-CO-Leu-NH$_2$,
(oooo) PhPr-Val-Ala-AAsp-(S,S)-EP-CO-Phe-NH$_2$,
(pppp) PhPr-Val-Ala-AAsp-(R,R)-EP-CO-Phe-NH$_2$,
(qqqq) PhPr-Val-Ala-AAsp-(S,S)-EP-CO-Tyr-NH$_2$,
(rrrr) Cbz-Glu-Val-AAsp-(R,R)-EP-CO-Phe-NH$_2$,
(ssss) Cbz-Glu-Val-AAsp-(S,S)-EP-CONHCH$_2$CH$_2$Ph,
(tttt) Cbz-Asp-Glu-Val-AAsp-(S,S)-EP-CO-Phe-NH$_2$,
(uuuu) Cbz-Asp-Glu-Val-AAsp-(S,S)-EP-CONHCH$_2$Ph,
(vvvv) Cbz-Asp-Glu-Val-AAsp-(S,S)-EP-COOCH$_2$Ph,
(wwww) Cbz-Leu-Glu-Thr-AAsp-(S,S)-EP-CONHCH$_2$CH$_2$Ph,
(xxxx) Cbz-Leu-Glu-Thr-AAsp-(S,S)-EP-CO-Ala-NHCH$_2$Ph,
(yyyy) Cbz-Ile-Glu-Thr-AAsp-(S,S)-EP-CO-Ala-NHCH$_2$Ph,

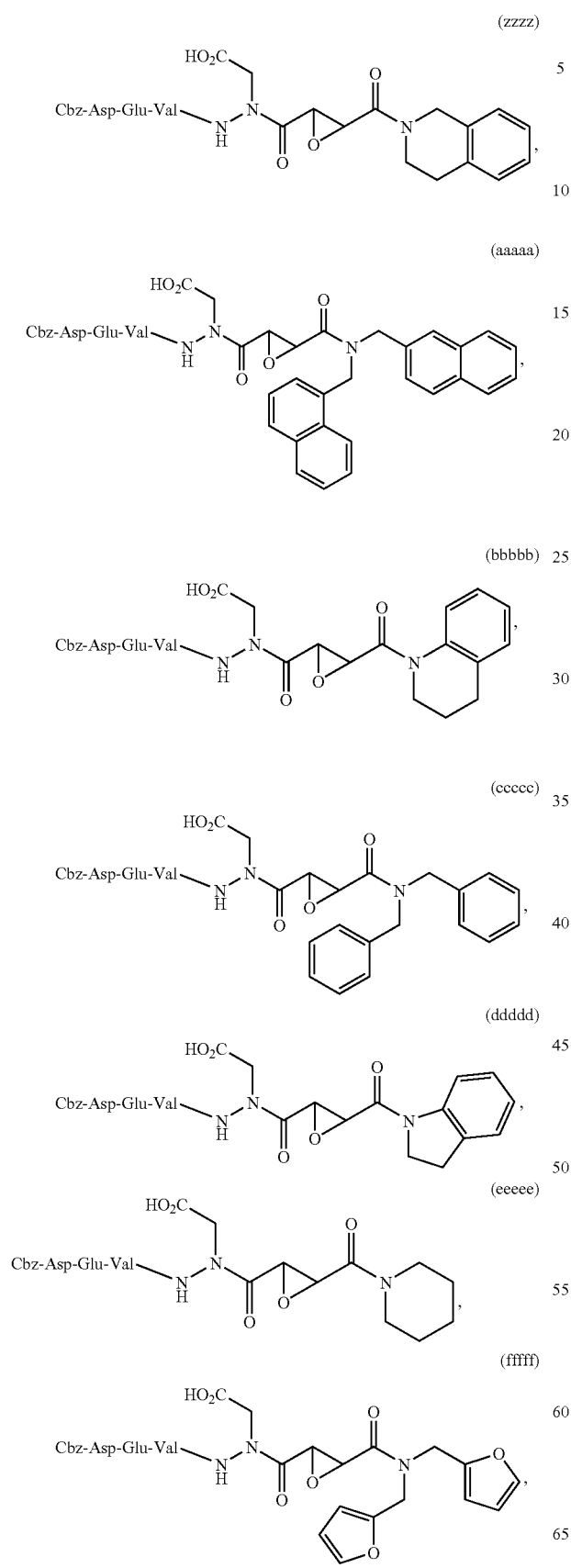
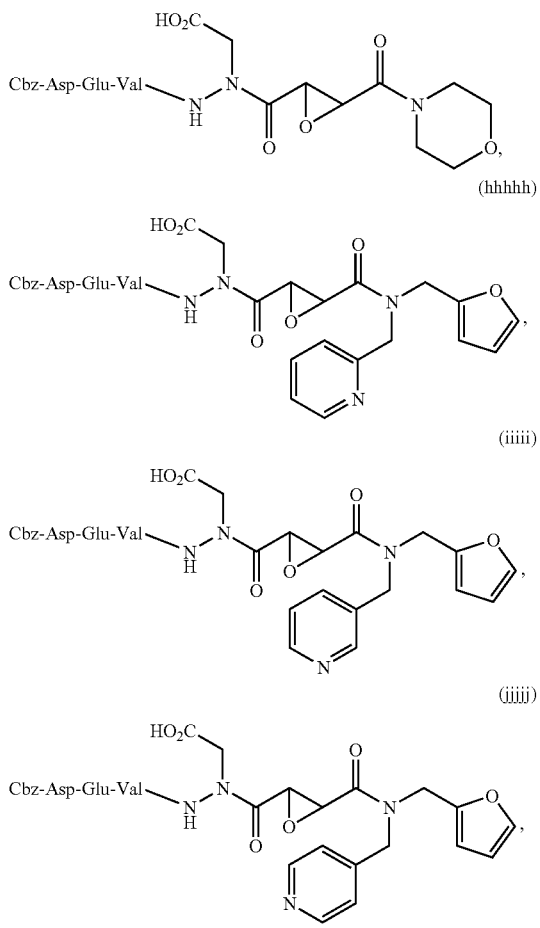

(kkkkk) Cbz-Leu-Glu-Thr-AAsp-(S,S)-EP-COOCH$_2$Ph,
(lllll) Cbz-Ile-Glu-Thr-AAsp-(S,S)-EP-COOCH$_2$Ph,
(mmmmm) Cbz-Ile-Glu-Thr-AAsp-(R,R)-EP-COOCH$_2$Ph,
(nnnnn) Cbz-Ile-Glu-Thr-AAsp-(R,R)-EP-CONHCH$_2$Ph,
and a pharmaceutically acceptable salt, pharmaceutically acceptable derivative, or combination thereof.

13. A compound having the chemical formula of Cbz-Asp-Glu-Val-AAsp-EP-COOCH$_2$C$_6$H$_5$.

14. A compound according having the chemical formula Cbz-Ala-Ala-AAsn-EP-COOEt.

15. A pharmaceutical composition, comprising an effective amount of a compound of claim 1 and a pharmaceutically acceptable carrier.

16. A method of inhibiting a cysteine protease comprising the step of contacting said cysteine protease with a compound according to claim 1.

17. The method of claim 16 wherein said contacting occurs in vivo.

18. The method of claim 16 wherein said contacting occurs in vitro.

19. The method according to claim 16 wherein said cysteine protease comprises a caspase.

20. The method according to claim 16 wherein said cysteine protease comprises legumain.

21. The method according to claim 16 wherein said cysteine protease comprises a member of the clan CD of cysteine proteases.

22. The method according to claim 16 wherein said cysteine protease comprises a member of the clan CA of cysteine proteases.

23. A method of preparing a compound comprising of the step of coupling an epoxide with a substituted hydrazide.

24. The method of claim 23 wherein said epoxide is an epoxysuccinate.

25. The method of claim 23 wherein said epoxide is an oxirane carboxylic acid.

26. The method of claim 23 wherein said coupling comprises the step of reacting the epoxide, substituted hydrazide, EDC, and HOBt.

27. The method of claim 23 wherein said coupling comprises the step of: reacting the epoxide, substituted hydrazide, NMM, and IBCF.

28. A compound comprising an aza-amino acid and an epoxide, wherein said aza-amino acid does not have the formula:

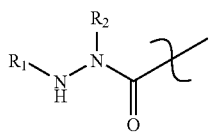

wherein, R1 is a quinolinyl and R2 is H.

29. A compound comprising an aza-amino acid and an epoxide, wherein the compound comprises P1 and P2 residues.

30. The compound of claim 29, wherein the P1 or P2 residue comprises an aza-amino acid residue.

31. The compound of claim 29, wherein the P1 residue comprises an aza-amino acid residue having a basic functional group.

32. The compound of claim 29, wherein the P2 residue comprises an amino acid residue having a hydrophobic functional group.

33. The compound of claim 29, wherein the P2 residue comprises an amino acid residue having a hydrophobic alkyl functional group.

34. A compound comprising an aza-amino acid and an epoxide, wherein said epoxide is coupled to said aza-amino acid.

35. The compound of claim 29 containing an anionic side chain at said P1 site.

36. The compound of claim 29 containing an aza-aspartic acid at the P1 site.

37. The compound of claim 29 containing an aza-asparagine at said P1 site.

38. A compound comprising an aza-amino acid and an epoxide, wherein said compound specifically inhibits cysteine proteases selected from the group consisting of clan CD and clan CA cysteine proteases.

39. The compound of claim 38, wherein said compound inhibits clan CD and clan CA cysteine proteases.

40. A neuroprotective composition comprising an aza-peptide epoxide.

41. A method of treating a neurodegenerative disorder comprising:
administering an effective amount of an aza-peptide epoxide to a patient having symptoms of a neurodegenerative disorder.

42. The method of claim 41, wherein said aza-peptide epoxide inhibits a protease.

43. The method of claim 42, wherein said protease comprises a cysteine protease.

44. The method of claim 41, wherein said neurodegenerative disorder is selected from the group consisting of stroke, Alzheimer's disease, Parkinson's disease, multiple sclerosis, neuropathies, Huntington's disease, dentatorubropallidoluysian atrophy, spinocerebellar atrophy type 3, spinal bulbar muscular atrophy, and myotrophic lateral sclerosis.

45. A method of modulating a host's immune system comprising administering to said host a composition comprising an aza-peptide epoxide in an amount sufficient to inhibit cleavage of an antigen in the host and reduce antigen peptides displayed on cell surfaces.

46. The method of claim 45, wherein said host is a mammal.

47. A method for treating inflammatory disease in a host comprising:
administering to said host a composition comprising an aza-peptide epoxide in an amount sufficient to inhibit a cysteine protease.

48. The compound of claim 28, wherein the compound comprises P1, P2 and P3 residues.

49. The compound of claim 28, wherein the compound comprises P1, P2, P3, and P4 residues.

50. The compound of claim 28, wherein the compound comprises P1, P2, P3, P4, and P1' residues.

* * * * *